US010961329B2

(12) United States Patent
Tang et al.

(10) Patent No.: US 10,961,329 B2
(45) Date of Patent: Mar. 30, 2021

(54) POLYOLEFIN CATALYST AND USE THEREOF

(71) Applicant: SHANGHAI CHEMRUN CO. LTD., Shanghai (CN)

(72) Inventors: Yong Tang, Shanghai (CN); Jiashuai Liu, Shanghai (CN); Wenjie Tao, Shanghai (CN); Xiuli Sun, Shanghai (CN); Junfang Li, Shanghai (CN)

(73) Assignee: SHANGHAI CHEMRUN CO. LTD., Shanghai (CN)

( * ) Notice: Subject to any disclaimer, the term of this patent is extended or adjusted under 35 U.S.C. 154(b) by 0 days.

(21) Appl. No.: 15/519,679

(22) PCT Filed: Oct. 19, 2015

(86) PCT No.: PCT/CN2015/092201
§ 371 (c)(1),
(2) Date: Jul. 6, 2017

(87) PCT Pub. No.: WO2016/058559
PCT Pub. Date: Apr. 21, 2016

(65) Prior Publication Data
US 2017/0349675 A1 Dec. 7, 2017

(30) Foreign Application Priority Data
Oct. 17, 2014 (CN) .......................... 2014 1 0555078

(51) Int. Cl.
| C08F 4/70 | (2006.01) |
| C08F 8/04 | (2006.01) |
| C07D 277/00 | (2006.01) |
| C07D 263/00 | (2006.01) |
| C08F 10/00 | (2006.01) |
| C07F 15/04 | (2006.01) |
| C07F 15/00 | (2006.01) |
| C08F 4/26 | (2006.01) |
| C08F 4/80 | (2006.01) |
| C10G 50/00 | (2006.01) |
| C10G 69/12 | (2006.01) |
| C10M 105/04 | (2006.01) |
| C10N 20/02 | (2006.01) |
| C10N 20/04 | (2006.01) |
| C10N 30/02 | (2006.01) |

(52) U.S. Cl.
CPC .......... *C08F 4/7098* (2013.01); *C07D 263/00* (2013.01); *C07D 277/00* (2013.01); *C07F 15/0066* (2013.01); *C07F 15/04* (2013.01); *C07F 15/045* (2013.01); *C08F 4/26* (2013.01); *C08F 4/70* (2013.01); *C08F 4/7034* (2013.01); *C08F 4/80* (2013.01); *C08F 8/04* (2013.01); *C08F 10/00* (2013.01); *C10G 50/00* (2013.01); *C10G 69/126* (2013.01); *C10M 105/04* (2013.01); *C10G 2300/302* (2013.01); *C10G 2400/10* (2013.01); *C10M 2203/022* (2013.01);

*C10N 2020/02* (2013.01); *C10N 2020/04* (2013.01); *C10N 2030/02* (2013.01)

(58) Field of Classification Search
None
See application file for complete search history.

(56) References Cited

U.S. PATENT DOCUMENTS

| 6,136,748 A | 10/2000 | Smith | |
| 2001/0025007 A1* | 9/2001 | Ponasik, Jr. ............ | C08F 10/00 502/167 |
| 2005/0240025 A1 | 10/2005 | Glorius | |
| 2014/0088319 A1 | 3/2014 | Tan et al. | |

FOREIGN PATENT DOCUMENTS

| CN | 1580084 A | 2/2005 |
| CN | 102786435 A | 11/2012 |
| CN | 103360517 A | 10/2013 |
| JP | S52-066531 A | 6/1977 |
| JP | S57-130973 A | 8/1982 |
| JP | S60-142929 A | 7/1985 |
| JP | H10-324710 A | 12/1998 |
| JP | 2003-301121 A | 10/2003 |
| JP | 2005-538071 A | 12/2005 |
| WO | 98/40420 A2 | 9/1998 |
| WO | 99/47572 A1 | 9/1999 |
| WO | 01/40325 A1 | 6/2001 |

(Continued)

OTHER PUBLICATIONS

Ellis et al. JOC, 2011, 76, 7180-7185 (Year: 2011).*
Steiner et al. Eur. J. Inorg. Chem., 2827-2836 (Year: 2004).*
Abakunnov et al. RSC Advances, 2014, 4, 14495 (Year: 2014).*
English language translation International Search Report dated Jan. 22, 2016 corresponding to International Patent Application No. PCT/CN2015/092201,filed Oct. 19, 2015, 2 pages.
Ans d. Chem. Institut d. University of Würzburg, "In Berichte der Deutschen Chemischen Gesellschaft B," [In Reports of the German Chemical Society B] *Siegfried Skraup und Mrie Moser: Über Benzoxazol-Derivata* (Mar. 15, 1922); vol. 55B, pp. 1080-1101. See, Concise Statement.

(Continued)

*Primary Examiner* — Yun Qian
(74) *Attorney, Agent, or Firm* — Mintz Levin Cohn Ferris Glovsky and Popeo PC

(57) ABSTRACT

Disclosed is a new polyolefin catalyst and preparation therefor. Specifically, disclosed is a catalytic system comprising a new complex of iron, cobalt, nickel, palladium, and platinum. In the presence of the catalytic system, oily polyethylene can be efficiently obtained from simple olefins such as ethylene under mild conditions, highly branched oily alkane mixture is then obtained after hydrogenation. The alkane mixture can be used as a processing aid and a high-performance lubricant base oil. The present invention also provides a method for preparing the catalyst, a method for preparing the highly branched oily alkane mixture and a method for preparing functional polyolefin oil.

10 Claims, 5 Drawing Sheets

(56) References Cited

FOREIGN PATENT DOCUMENTS

| WO | 2006/036748 A2 | 4/2006 | | |
|---|---|---|---|---|
| WO | 2007/062790 A2 | 6/2007 | | |
| WO | WO-2007062790 A2 * | 6/2007 | ........... | C07D 231/56 |
| WO | 2012/109343 A2 | 8/2012 | | |
| WO | 2013/045516 A1 | 4/2013 | | |

OTHER PUBLICATIONS

Extended European Search Report dated Jul. 17, 2018 corresponding to European Patent Application No. 15850627.9 filed Oct. 19, 2015 (int'l filing date); 9 pages.

First Office Action dated Jul. 12, 2018 corresponding to Japanese Patent Application No. 2017-520904; 6 pages; See, English language machine translation.

First Office Action dated Feb. 14, 2019 corresponding to Chinese Patent Application No. 201410555078X; 9 pages; See, English translation.

Anderson, James C. et al., "Steroselective Symthesis of Densely Functionalized Pyrrolidin-2-ones by a Conjugate Addition/Nitro-Mannich/Lactamization Reaction," *Journal of Organic Chemistry* (Jun. 18, 2012); 77(14):6186-6198.

Cloete, Jezreel et al., "Functionalized pyridinyl-imine complexes of palladium as catalyst precursors for ethylene polymerization," *Journal of Molecular Catalysis A: Chemical* (2006; Available online Sep. 26, 2005); 243:221-225.

Du, Jianlong et al., "Ni(II) complexes bearing 2-aryliminobenzimidazole: synthesis, structure and ethylene oligomerization study," *Inorganic Chemistry Communications* (2005; Accepted Dec. 23, 2004); 8:246-248.

Johnson, James A. et al., "Total Synthesis of (−)-Rhazinilam: Asymmetric C—H Bond Activation via the Use of a Chiracl Auxiliary," *J. Am. Chem. Soc.* (May 23, 2002); 124:6900-6903.

Knempfen, H. X., "Synthesis of Some Binaphthoxazoles," *Journal of Heterocyclic Chemistry* (Apr. 1972); 9(2):303-307.

Laine, Timo V. et al., "Pyridinylimine-based nickel(II) and palladium(II) complexes: preparation, structural characterization and use as alkene polymerization catalysts," *Journal of Organometallic Chemistry* (Received in revised form Apr. 3, 2000); 606:112-124.

Perl, Nicholas R. et al., "Enantioselective Imidazole-Directed Allylation of Aldimines and Ketimines," *Organic Letters* (Received Jul. 19, 2007); 9(18):3699-3701.

Rogness, Donald C., et al., "Synthesis of Pyrido{1,2-α]indole Malonates and Amines through Aryne Annulation," *The Journal of Organic Chemistry* (Feb. 22, 2012); 77:2743-2755.

Shue, C. F. et al., "Mössbauer and Magnetic Studies of Copper(II)-Phthalocyanine Effect on the Spin States of Bis(N-o-Tolyl-2-Imidazolaldimine)Iron(II) Dithiocyanate," *Polyhedron* (Accepted Mar. 7, 1994); 13(15/16):2259-2264.

Tauer, Erich et al., "The Condensation Product of 2-Aminophenol and Glyoxal. Structure and Photochemistry," *Chemische Berichte* (1986); (Received Jun. 25, 1986); 119(11):3316-3325.

Tauer, Erich et al., "Photochemical Dehydrogenation, Ring Contraction, and Ring Expansion of Hydrogenated Derivatives of Benzoxazino-benzoxazine, Quinoxalino-quinoxaline, and Bibenzothiazole," *Chemische Berichte* (1990; Received Nov. 13, 1989); 123(5):1149-1154.

Vedejs, Edwin et al., "Oxazolium-Derived Azomethine Ylides. External Oxazole Activation and Internal Dipole Trapping in the Synthesis of an Aziridinomitosene," *J. Org. Chem.* (Published on Web Aug. 9, 2000); 65(18):5498-5505.

* cited by examiner

POLYOLEFIN CATALYST AND USE THEREOF

FIELD OF THE INVENTION

The present invention relates to the preparation of base oil for lubricant, and specifically, the present invention relates to a new polyolefin catalysts and preparation methods thereof, as well as methods to achieve direct preparation of oily hyperbranched polymers from simple olefins, such as ethylene, propylene, butylene and polar olefins containing functional groups in the presence of the catalyst.

BACKGROUND OF THE INVENTION

The base oil for industrial lubricants is obtained by oil cracking or α-olefin oligomerization. Among them, as very important lubricating base oil with excellent performance, poly-α-olefin (PAO) is obtained by α-olefin oligomerization, and main raw materials are expensive α-olefins such as α-octene, α-decene, α-dodecene, etc.

Therefore, currently, the premise for obtaining high-quality base oil PAO is to catalyze the ethylene oligomerization of α-olefins firstly, especially α-decene, and the selective production technology of C6 or higher α-olefin is not yet mature, thus resulting in its high price. Direct production of high performance base oils from cheap olefins such as ethylene, propylene and butene has the advantages of being economical and efficient. However, due to the lack of efficient catalytic systems, there has been no significant progress in this field yet.

Prior to 1995, nickel complexes were considered to act only as catalysts for catalyzing olefin oligomerization. For example, well-known SHOP catalysts could catalyze the high activity of ethylene to obtain a series of α-olefins in accordance with Flory distribution. On 1995, Brookhart et al. (*J. Am. Chem. Soc.* 1995, 117, 6414.) for the first time proved that ethylene polymerization can be achieved by nickel complex catalytic through changing the ligand structure to control the nature of the active center by using α-diimine nickel complexes, thereby obtaining branched high molecular weight polyethylene, wherein the melting point of the polymer (Tm) is 39-132° C. Du Pont Company has filed several patent applications for this technology (WO96/23010, WO98/03521, WO 98/40374, WO99/05189, WO99/62968, WO00/06620, U.S. Pat. Nos. 6,103,658, 6,660,677) in order to protect this type of polymerized products. The oily polyethylene can be obtained from the corresponding cationic palladium system, and the polyolefin has a high branching degree, but the catalyst is difficult to prepare, expensive and of low catalytic activity.

The morphology and performance of polyethylene closely relates to its branching degree, and the catalyst structure is the core of controlling polyethylene structure. The polyethylene prepared by Brookhart et al. from nickel catalyst possesses certain branching degree, but still can not meet the requirements in which the product is solid state at room temperature. In 2011, the applicant has filed application CN201110126431.9, where the use of novel α-diimine nickel complexes has achieved high activity in catalyzing simple olefin polymerization such as ethylene to obtain highly branched oily polyesters and other oily polymers.

In general, although polyolefin oil has a huge potential application value, there are few catalyst technologies being able to achieve low-cost manufacture of the product. In particular, it is desirable in the practical application that the polyolefin structure contains certain polar groups to organically complex with other materials. Therefore, there is an urgent need in the art for the development of new and efficient catalytic systems for the preparation of low cost high performance oily polymers.

SUMMARY OF THE INVENTION

The object of the present invention to provide a novel catalytic system and a process for the preparation of key catalysts therein. Through the control of the catalyst structure, the catalytic system can achieve direct preparation of high branching degree oily polymers from cheap olefins such as ethylene, propylene or butene.

Another object of the present invention is to provide a novel catalytic system for using in the synthesis of highly branched alkanes.

Another object of the present invention to provide a class of highly branched alkanes which can be used in advanced lubricating base oils.

In the first aspect of the present invention, a compound of formula I is provided,

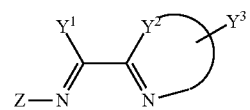

I

Wherein, $Y^1$ is hydrogen, C1-C8 alkyl or C1-C8 haloalkyl, unsubstituted or substituted phenyl;

$Y^2$ is $CR_4R_5$, $NR_6$, O or S, $R_4$, $R_5$, $R_6$ are independently H, C1-C4 alkyl or haloalkyl;

Or $Y^1$ and $Y^2$, and the C—C bond attached to both of them together forms unsubstituted or substituted 5-12 member ring (e.g., together forms compounds such as

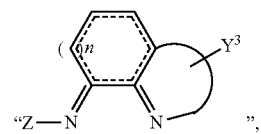

wherein the dotted lines mean chemical bond or none);

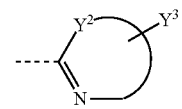

is unsubstituted or substituted 5-7 member monocyclic formed together with $Y^2$, or bicyclic or tricyclic group containing aforementioned 5-7 member monocyclic ring, wherein the 5-7 member monocyclic ring contains 1-3 N, O or S atoms, and contains at least one N;

$Y^3$ is one or more substituents optionally on the aforementioned 5-7 member monocyclic ring, or bicyclic or tricyclic group containing aforementioned 5-7 member monocyclic ring, each $Y^3$ is independently hydrogen, C1-C8 alkyl or C1-C8 haloalkyl, unsubstituted or substituted phenyl, unsubstituted or substituted benzyl;

Z is C1-C8 alkyl, C1-C8 haloalkyl, unsubstituted or substituted phenyl;

wherein, unless otherwise indicated, the "substituted" in the above definitions means that the group possesses 1-5 substituents selected from the following group: C1-C4 alkyl and C1-C4 haloalkyl, halogen, nitro, cyano, $CF_3$, $-O-R_1$, $-N(R_2)_2$, $-Si(R_3)_3$, $-CH_2-O-R_8$, $-SR_9$ or $-CH_2-S-R_{10}$, wherein $R_1$, $R_2$ and $R_3$ are independently C1-C4 alkyl or haloalkyl; while $R_8$, $R_9$ and $R_{10}$ are independently C1-C8 alkyl or phenyl.

In another preferred embodiment,

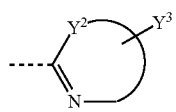

is optically active or racemic.

In another preferred embodiment, in

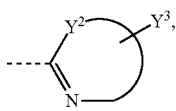

the ortho-position of N is C atom, and the C atom has one or more non-hydrogen substituents.

In another preferred embodiment, the non-hydrogen substituent is selected from the following groups: C3-C8 alkyl (preferably branched alkyl) or C3-C8 haloalkyl (preferably branched haloalkyl), unsubstituted or substituted phenyl, unsubstituted or substituted benzyl.

In another preferred embodiment, the "form together with $Y^2$" comprises to form together with the whole $Y^2$, or form with a moiety of $Y^2$.

In another preferred embodiment,

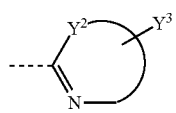

is selected from the following groups:

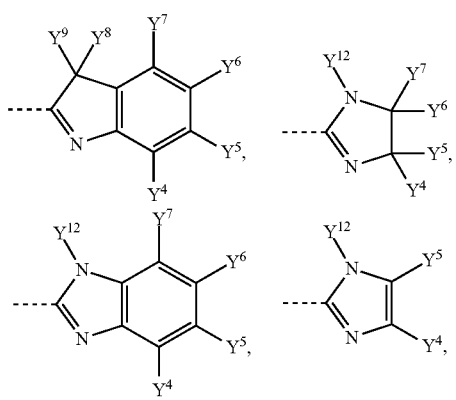

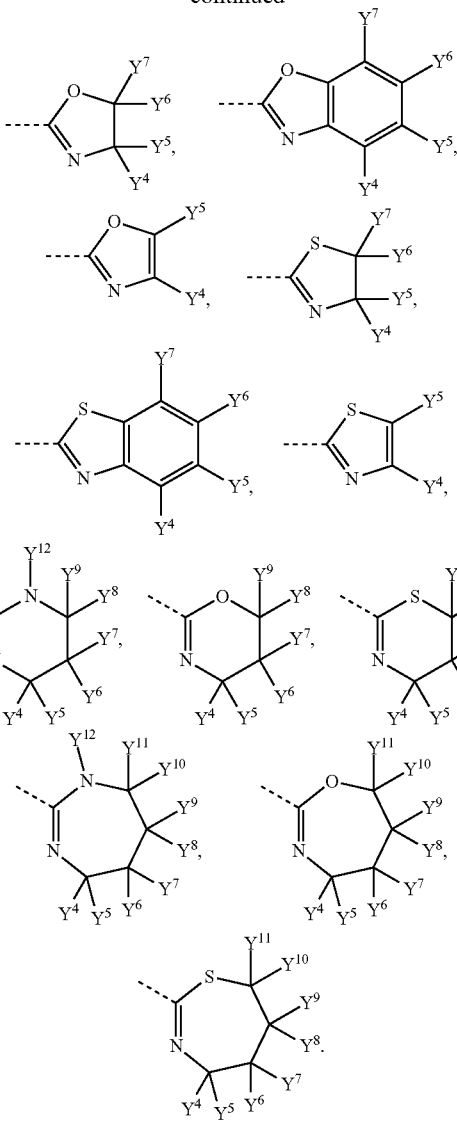

$Y^4$, $Y^5$, $Y^6$, $Y^7$, $Y^8$, $Y^9$, $Y^{10}$ and $Y^{11}$ are independently H, halogen, C1-C8 alkyl, C1-C8 haloalkyl, unsubstituted or substituted phenyl, unsubstituted or substituted benzyl, $-O-R_7$, $-CH_2-O-R_8$, $-SR_9$ or $-CH_2-S-R_{10}$, wherein $R_7$, $R_8$, $R_9$ and $R_{10}$ are independently C1-C8 alkyl, unsubstituted or substituted phenyl; $Y^{12}$ is H, C1-C8 alkyl, C1-C8 haloalkyl, unsubstituted or substituted phenyl, unsubstituted or substituted benzyl.

In another preferred embodiment,

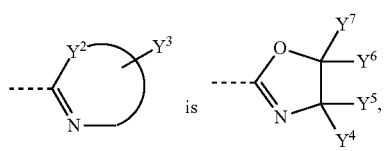

wherein 1-3 substituents of $Y^4$, $Y^5$, $Y^6$ and $Y^7$ is H, C1-C8 alkyl, C1-C8 haloalkyl, unsubstituted or substituted phenyl, and 1-3 substituents are H, halogen, C1-C4 alkyl and C1-C4 haloalkyl.

In another preferred embodiment,

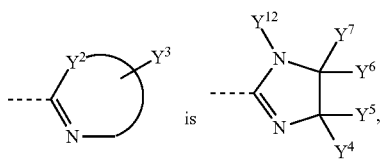 is 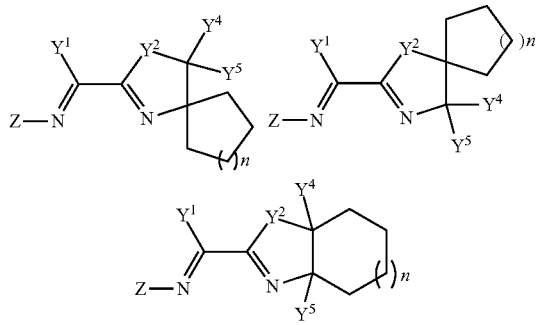

wherein 1-3 substituents of $Y^4$, $Y^5$, $Y^6$, $Y^7$ and $Y^{12}$ is H, C1-C8 alkyl, C1-C8 haloalkyl, unsubstituted or substituted phenyl, and 1-3 substituents are H, halogen, C1-C4 alkyl and C1-C4 haloalkyl.

In another preferred embodiment, $Y^{12}$ is not halogen.

In another preferred embodiment, $Y^1$ and $Y^2$ can form unsubstituted or substituted C6-C8 ring together with the C—C bond attached with both of them, wherein the "substituted" is defined as abovementioned.

In another preferred embodiment, the compound has the following structure:

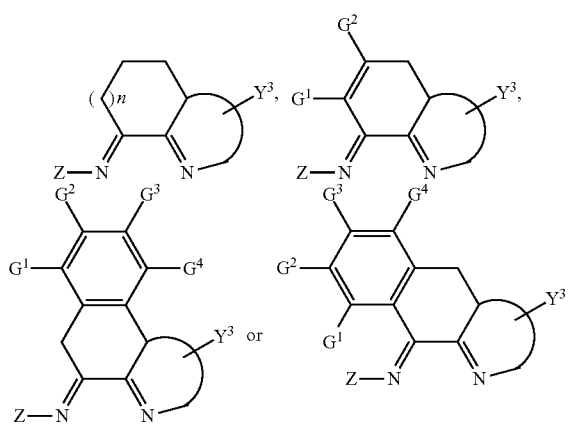

wherein:
$Y^3$ or Z are defined as in claim 1;
n is 0, 1, 2, or 3;

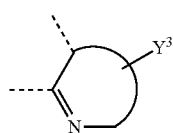

is unsubstituted or substituted 5-7 member monocyclic, or bicyclic or tricyclic group containing said 5-7 member monocyclic ring;

$G^1$, $G^2$, $G^3$ and $G^4$ are independently H, halogen, C1-C8 alkyl, C1-C8 haloalkyl, silicon group, unsubstituted or substituted phenyl, unsubstituted or substituted benzyl, —O—$R_7$, —$CH_2$—O—$R_8$, —$SR_9$ or —$CH_2$—S—$R_{10}$, wherein $R_7$, $R_8$, $R_9$ and $R_{10}$ are independently C1-C8 alkyl, unsubstituted or substituted phenyl; wherein the "substituted" is defined as above.

In another preferred embodiment, the bicyclic ring containing the 5- to 7-membered monocyclic ring is a spiro or fused ring, and preferably the compound has any of the following structures:

wherein,
each n is independently 1, 2, 3, or 4;
$Y^1$, $Y^2$ and Z are defined as in claim 1;
$Y^4$ and $Y^5$ are independently H, halogen, C1-C8 alkyl, C1-C8 haloalkyl, unsubstituted or substituted phenyl, unsubstituted or substituted benzyl, —O—$R_7$, —$CH_2$—O—$R_8$, —$SR_9$ or —$CH_2$—S—$R_{10}$, wherein $R_7$, $R_8$, $R_9$ and $R_{10}$ are independently C1-C8 alkyl, unsubstituted or substituted phenyl; wherein $Y^4$ and $Y^5$ cannot be halogen, —O—$R_7$ or —$SR_9$ simultaneously.

In another preferred embodiment, each chiral center (preferably carbon atom) in the compound of formula I is R configuration and/or S configuration.

In another preferred embodiment, the carbon atom of the 5-7 monocyclic ring attaches to $Y^4$ and/or $Y^5$ is R configuration and/or S configuration.

In another preferred embodiment, the Z is unsubstituted or substituted phenyl, or unsubstituted or substituted naphthyl, wherein "substituted" in the above definitions means that the group possesses 1-5 substitutents selected from the group consisting of: C1-C4 alkyl, C1-C4 haloalkyl, halogen, nitro, cyano, $CF_3$, —O—$R_1$, —$N(R_2)_2$, —$Si(R_3)_3$, —$CH_2$—O—$R_8$, —$SR_9$, —$CH_2$—S—$R_{10}$, —CH—$(R_{10})_2$, or phenyl which is unsubstituted or substituted by 1-5 substituents selected from the following group: C1-C4 alkyl, C1-C4 haloalkyl, wherein $R_1$, $R_2$, $R_3$ are independently C1-C4 alkyl or haloalkyl; while $R_8$, $R_9$ and $R_{10}$ are independently C1-C8 alkyl or phenyl;

And the substituted phenyl group can have at most one nitro or cyano group.

More preferably, Z is one of the following groups:

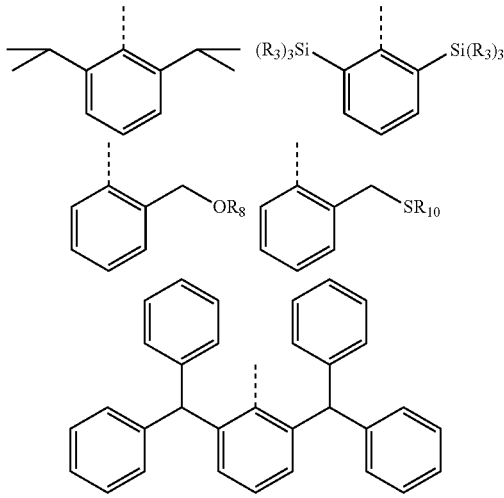

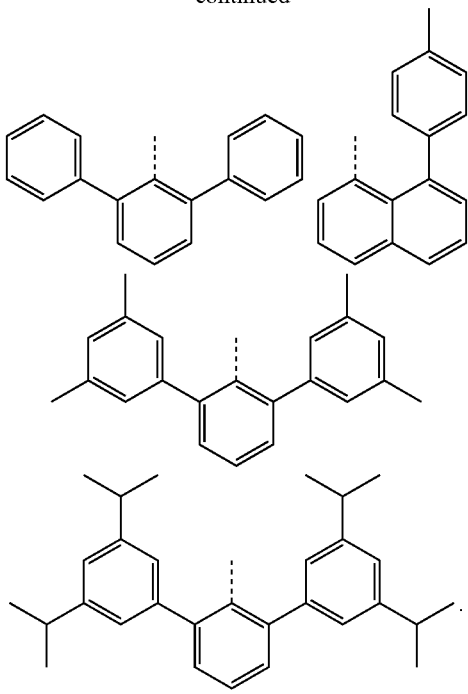

In another preferred embodiment, any of $Y^1$, $Y^2$, $Y^3$, $Y^4$, $Y^5$, $Y^6$, $Y^7$, $Y^8$, $Y^9$, $Y^{10}$, $Y^{11}$, $Y^{12}$, Z, $R_1$, $R_2$, $R_3$, $R_4$, $R_5$, $R_6$, $R_7$, $R_8$, $R_9$ and $R_{10}$ is the corresponding group of the specific compounds in the present invention.

In the second aspect of the present invention, a complex is provided, wherein the complex is formed by the compound of the first aspect of the present invention and a divalent or trivalent metal salt.

Preferably, the metal salt contains metal selected from the group consisting of iron, cobalt, nickel, palladium, platinum, or combinations thereof.

In another preferred embodiment, the metal salt is a divalent metal salt and the complex has the structure represented by the following formula II:

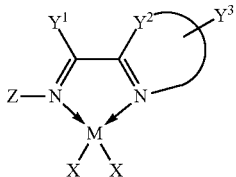

wherein, $Y^1$, $Y^2$, $Y^3$ and Z are defined as in claim 1;

M is iron, cobalt, nickel, palladium, platinum, or combinations thereof;

X is independently halogen, C1-C4 alkyl, C2-C6 alkenyl, allyl (⤳), ⁻OAc, ⁻OTf, or benzyl.

In another preferred embodiment, the halogen is F, Cl, Br or I, preferably Cl or Br.

In the third aspect of the present invention, the preparation method of complex of the second aspect of the present invention is provided, wherein comprising the following steps: In an inert solvent, reacting the compound of the first aspect of the present invention to react with a divalent or trivalent metal salt so as to provide the complex of the second aspect of the present invention.

In another preferred embodiment, the metal salt is selected from the following group: $NiCl_2$, $NiBr_2$, $NiI_2$, $(DME)NiBr_2$, $PdCl_2$, $PdBr_2$, $Pd(OTf)_2$, $Pd(OAc)_2$, (COD)PdMeCl, or combinations thereof.

In another preferred embodiment, the reaction is carried out under almost anhydrous conditions (e.g., water content ≤0.1%).

In another preferred embodiment, the reaction is carried out in an inert atmosphere (such as nitrogen).

In the forth aspect of the present invention, a method for the preparation of compound of formula I is provided, wherein comprising the following steps:

(a) under basic conditions, a heterocyclic compound of formula A is oxidized to form a compound of formula B;

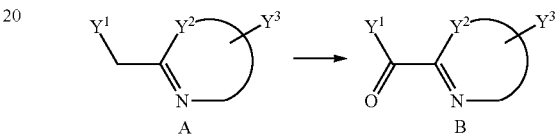

(b) the compound of formula B reacts with a compound of formula C to form a compound of formula I;

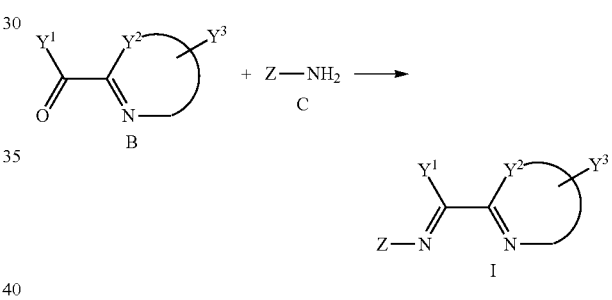

In each of the above formula, $Y^1$, $Y^2$, $Y^3$, Z and

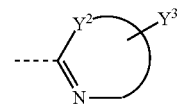

are defined as in claim 1.

In another preferred embodiment, the step (a) is carried out with a base to abstract the hydrogen in an inert organic solvent, wherein the base is preferably n-butyllithium, t-butyllithium, lithium diisopropylamide (LDA) or lithium hexamethyldisilazide (LHMDS); and then oxidized by oxygen, air or other oxidizing agents for 3-48 hours.

In another preferred embodiment, the inert organic solvent means a solvent which does not react with any of the chemical agents used in the present reaction.

In another preferred embodiment, in step (b), 0.001-100% corresponding catalysts which can promote this condensation reaction is added, preferably formic acid, acetic acid, p-toluenesulfonic acid, $TiCl_4$, or orthosilicate ester.

In another preferred embodiment, in step (b), the ratio of compound B to C is (0.7-1.2):1.

In another preferred embodiment, in step (a), the inert organic solvent comprises diethyl ether or tetrahydrofuran.

In another preferred embodiment, in step (b), the inert organic solvent is dichloromethane, methanol, ethanol or toluene.

In the fifth aspect of the present invention, a preparation method of oily olefin polymers is provided, which comprises the following steps:

(a) the olefins polymerization catalyzed by the complex provided in the second aspect of the present invention, in the presence of alkylaluminum compound as cocatalyst, to form oily polyolefins.

In another preferred embodiment, the alkyl aluminum compound comprises trialkylaluminum, dialkylaluminum chloride, alkylaluminum dichloride, alkylaluminoxane; the polymerization is carried out in an organic solvent, preferably aromatic hydrocarbons, alkanes and halogenated alkanes; more preferably toluene, C4-C10 alkanes or C1-C6 haloalkanes; more preferably toluene, C5-C7 alkanes, C1-C3 haloalkanes; most preferably toluene, C5-C7 alkanes, dichloromethane, 1,2-dichloroethane or 1,1,2,2-tetrachloroethane.

In another preferred embodiment, in step (a), the complex is in situ prepared or prepared in advance.

In another preferred embodiment, the method further comprises the following steps:

(b) hydrogenating the oily polyolefin obtained in step (a) to obtain hydrogenated oily alkane mixtures.

In another preferred embodiment, the olefin is ethylene, propylene or C4-C20 α-olefins, internal olefins, dienes, or the mixtures thereof.

In another preferred embodiment, the olefin further comprises polar monomers,

Preferably, the polar monomer is a C3-C50 olefin which comprises (a) polar group (s), wherein the polar group is selected from the following group: carbonyl, hydroxyl, —COOH, ester group —COOR$_{11}$, alkoxy —OR$_{12}$, amido —NR$_{13}$R$_{14}$, acylamino —CONR$_{15}$R$_{16}$, thioether —SR$_{17}$, selenide —SeR$_{18}$, —PR$_{19}$R$_{20}$, —P(═O)R$_{19}$R$_{20}$ or combinations thereof; wherein R$_{11}$ and R$_{12}$ are independently C1-C10 alkyl or C6-C20 aryl; R$_{13}$, R$_{14}$, R$_{15}$, R$_{16}$, R$_{17}$ or R$_{18}$ are independently hydrogen, C1-C10 alkyl, or C6-C20 aryl; R$_{19}$ or R$_{20}$ are independently C1-C10 alkyl or C6-C20 aryl.

In another preferred embodiment, the polar monomer is selected from the following groups:

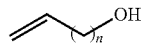

M1: n=1
M2: n=3
M3: n=8

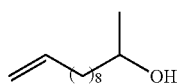

M4

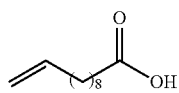

M5

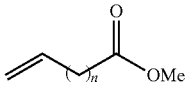

M6: n=0
M7: n=8

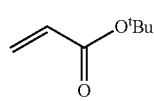

M8

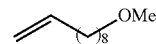

M9

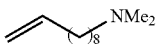

M10

M11

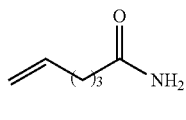

M12

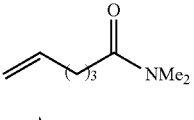

M13

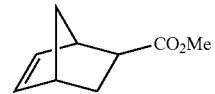

M14

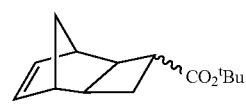

M15

M16

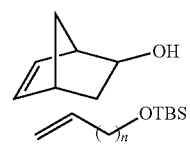

M17

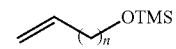

M18: n=1
M19: n=3
M20: n=8

M21: n=1
M22: n=3
M23: n=8

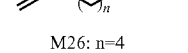

M24: n=4
M25: n=9

M26: n=4
M27: n=9

In another preferred embodiment, the method further comprises the following steps before step (a):

Mixing the polar monomer and cocatalyst to form a mixture, and using the mixture in step (a);

Or pretreating the polar monomer with protecting reagent and using the protected polar monomer in step (a).

In another preferred embodiment, the functional group protecting reagent is selected from the group consisting of: TBS, TES, TBDPS, TMS, AlEt$_3$, Al$^i$Bu$_3$, methyl aluminoxane, ethyl aluminoxane, butyl alumoinxane, MMAO, and combinations thereof.

In another preferred embodiment, the cocatalyst is selected from the group consisting of: alkyl aluminum compounds, alkyl aluminoxane, weakly coordinating anion, and combinations thereof.

In another preferred embodiment, the alkyl aluminum compounds is selected from the group consisting of: $AlEt_3$, $AlMe_3$, $Al^iBu_3$, or $AlEt_2Cl$.

In another preferred embodiment, the alkyl aluminoxane is selected from the following group: MMAO or MAO.

In another preferred embodiment, the weakly coordinating anion is selected from the following group: $[B(3,5\text{-}(CF_3)_2\ C_6H_3)_4]^-$ or $^-OSO_2CF_3$.

In another preferred embodiment, the "MMAO" refers to modified methyl aluminoxane (from Akzo Chemical Company).

In another preferred embodiment, the olefin is polar monomers, non-polar monomers, or combinations thereof.

In another preferred embodiment, the non-polar monomer comprises ethylene, propylene, butene, or combinations thereof.

In another preferred embodiment, the olefins are any combination of ethylene, propylene and/or butene with other C5-C20 olefins.

In another preferred embodiment, the oily olefin polymer is highly branched; more preferably, the highly branched means that the number of methyl in the polymer per 1000 methylene is 100-500.

In another preferred embodiment, the cocatalyst is used in step (a).

More preferably, the cocatalyst is selected from the following group or combinations thereof: alkyl aluminum reagents (such as alkyl aluminoxanes, diethylaluminum chloride and ethylaluminum dichloride).

In another preferred embodiment, the reaction temperature of step (a) is 0-100° C.

In another preferred embodiment, the reaction conditions of step (a) are: pressure (gauge pressure) 0.1-10 MPa, the cocatalyst is alkyl aluminoxane or diethyl aluminum chloride, wherein the molar ratio of aluminum of cocatalyst to catalyst is 10-5000.

In another preferred embodiment, step (a) is carried out in the following polymerization solvents: toluene, n-hexane, dichloromethane, 1,2-dichloroethane, chlorobenzene, tetrahydrofuran, or combinations thereof.

In another preferred embodiment, step (a) may be carried out in oily polyethylene or oily alkane mixture.

In another preferred embodiment, the method further comprises the following steps:

(b) hydrogenating the oily polyolefin obtained in step (a) to obtain a hydrogenated oily alkane mixture.

In another preferred embodiment, the bromine value of the oily alkane mixture is less than 0.5 g/100 g.

In another preferred embodiment, between step (a) and step (b) further comprises a step of oily polyolefin separation.

In another preferred embodiment, in step (a), hydrogenation reaction is situ conducted.

In another preferred embodiment, step (b) may be carried out in an inert solvent or directly be carried out in the oily polyolefin as solvent.

In another preferred embodiment, the oily alkane mixture is the hydrogenated product of the oily polyolefin of the invention.

In another preferred embodiment, the oily alkane mixture is the hydrogenated product of the oily polyethylene of the invention.

In another preferred embodiment, the oily olefin polymer or the hydrogenated product thereof possesses one or more of the following characteristics:

(i) the number of the methyl in the polymer is 100-500 methyl per 1000 methylene;

(ii) the molecular weight is 300-500,000 g/mol;

(iii) the density is 0.75-0.91 g/mol.

In another preferred embodiment, the number of methyl in the oily olefin polymer or the hydrogenated products thereof per 1000 methylene is 100-300, and preferably 150-300.

In another preferred embodiment, the number of branched chain in the oily olefin polymer or the hydrogenated products thereof per 1000 methylene is 100-300, and preferably 150-300. Wherein the branched chain comprises methyl, ethyl, n-propyl, n-butyl, sec-butyl and other branched chain with four or more carbons.

In another preferred embodiment, there are 40-70 branched alkyl chains per 1000 carbons.

In another preferred embodiment, the polymer has a branch of the following structure: straight or branched C3-C8 alkyl.

In another preferred embodiment, the branched alkyl chains is sec-butyl, and the number of sec-butyl per 1000 carbon is 15-30.

In another preferred embodiment, the 'oily' means that the olefin polymer is oily within all or part of the temperature range over −50° C. (preferably −40° C. to 50° C., more preferably −40° C. to 35° C.).

In another preferred embodiment, the 100° C. kinematic viscosity of the oily olefin polymer or the hydrogenated products thereof obtained in the present invention is 4-50 $mm^2/s$, viscosity index (VI) is 160-300, and the surface tension is over 20 mM/m. The test method of kinematic viscosity is as GB/T 265-1988 (2004), The test method of viscosity index (VI value) is as GB/T 1995-1998 (2004).

In another preferred embodiment, the molecular weight of the oily alkane mixture is 500-50,000 g/mol.

In another preferred embodiment, the hydrogenated product of the oily olefin polymer obtained in the present invention possesses excellent oxidative stability. Oxidation stability is tested according to SH/T 0193-2008 (rotating bomb oxidation).

In the sixth aspect of the present invention, an oily olefin polymer or the hydrogenated product thereof is provided, possessing one or more of the following characteristics:

(i) the number of polar group in the polymer chain: 0.1-1000 polar group per 1000 methylene, preferably 5-200, more preferably 5-50;

(ii) the number of the methyl in the polymer is 100-500 methyl per 1000 methylene;

(iii) the molecular weight is 300-500,000 g/mol;

(iv) the density is 0.75-0.91 g/mol.

In another preferred embodiment, 'oily' means that the olefin polymer is an oil within all or part of the temperature range over −50° C. (preferably over −40° C.).

In another preferred embodiment, the pour point of the oily alkane mixture is −60° C. to −20° C.

In another preferred embodiment, the oily olefin polymer or the hydrogenated product thereof comprises polar group, wherein the polar group is selected from the following group: carbonyl, hydroxyl, —COOH, ester group —$COOR_{11}$, alkoxy —$OR_{12}$, amido —$NR_{13}R_{14}$, acylamino —$CONR_{15}R_{16}$, thioether —$SR_{17}$, selenide —$SeR_{18}$, —$PR_{19}R_{20}$, —$P(=O)R_{19}R_{20}$ or combinations thereof; wherein $R_{11}$ and $R_{12}$ are independently C1-C10 alkyl or C6-C20 aryl; $R_{13}$, $R_{14}$, $R_{15}$, $R_{16}$, $R_{17}$ or $R_{18}$ are independently hydrogen, or C1-C10 alkyl, or C6-C20 aryl; $R_{19}$ or $R_{20}$ are independently C1-C10 alkyl or C6-C20 aryl.

In the seventh aspect of the present invention, usage of the oily olefin polymer or the hydrogenated product of the sixth aspect of the invention is provided, wherein as lubricant base oil, a lubricant additive(s), a plasticizer(s) or a processing aid(s) of resin.

In the eighth aspect of the present invention, an oily alkane mixture is provided, wherein there are 20-100 branched alkyl chains with multiple ends per 1000 carbons in the oily alkane mixture.

In another preferred embodiment, the oily alkane mixture is prepared by method of the fifth aspect of the invention.

In another preferred embodiment, the oily alkane mixture is prepared by method of the fifth aspect of the invention using ethylene as polymerization monomer.

In another preferred embodiment, in the oily alkane mixture, the number of methyl ($CH_3$) per 1000 methylene is 100-300.

In another preferred embodiment, there are 40-70 branched alkyl chains with multiple ends per 1000 carbons.

In another preferred embodiment, there are 15-30 sec-butyl per 1000 carbon in the polymer.

In another preferred embodiment, the polymer has a branch of the following structure: straight or branched C1-C8 alkyl.

In another preferred embodiment, the polymer has a branch of the following structure: straight or branched C3-C8 alkyl.

In another preferred embodiment, the pour point of the oily alkane mixture is −40 to −20° C., preferably −60° C. to −20° C.

In another preferred embodiment, the polymer is colorless transparent oily product.

In another preferred embodiment, the molecular weight of the oily alkane mixture is 500-50,000 g/mol, preferably 500-10,000 g/mol.

In another preferred embodiment, in the oily alkane mixture, the number of methyl ($CH_3$) per 1000 methylene is 100-300.

In another preferred embodiment, the kinematic viscosity of the oily alkane mixture at 100° C. is 4-50 $mm^2/s$.

In another preferred embodiment, the viscosity index (VI value) of the oily alkane mixture is 160-300.

In another preferred embodiment, the surface tension of the oily alkane mixture is greater than 20 mM/m.

In another preferred embodiment, the surface tension of the oily alkane mixture is 20 mM/m-40 mM/m.

In another preferred embodiment, the density of the oily alkane mixture is 0.75-0.91 g/mol.

In another preferred embodiment, the oxidative stability of the hydrogenated oily alkane mixture is greater than 50 min, preferably greater than 70 min, more preferably greater than 90 min.

In another preferred embodiment, the oily alkane mixture is colorless transparent oily product within temperature range from −50° C. to 200° C.; preferably colorless transparent oily product within temperature range from −40° C. to 50° C.

In the ninth aspect of the present invention, a lubricating oil containing the oily olefin polymer of the sixth aspect of the present invention and/or hydrogenated product thereof (i.e., oily alkane mixture), or the oily alkane mixture of the eighth aspect of the present invention is provided.

In another preferred embodiment, the viscosity index (VI value) of the lubricating oil is 130-200.

In another preferred embodiment, the lubricating oil contains 0.1 to 100 wt % (preferably 1 to 90 wt %) of oily alkane mixture.

In the ninth aspect of the present invention, a use of complex of the second aspect of the present invention as the catalyst of olefin polymerization is provided.

In another preferred embodiment, the olefin polymerization is carried out under homogeneous conditions.

In another preferred embodiment, the catalyst is supported on inorganic carrier or an organic carrier.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Figure 1:
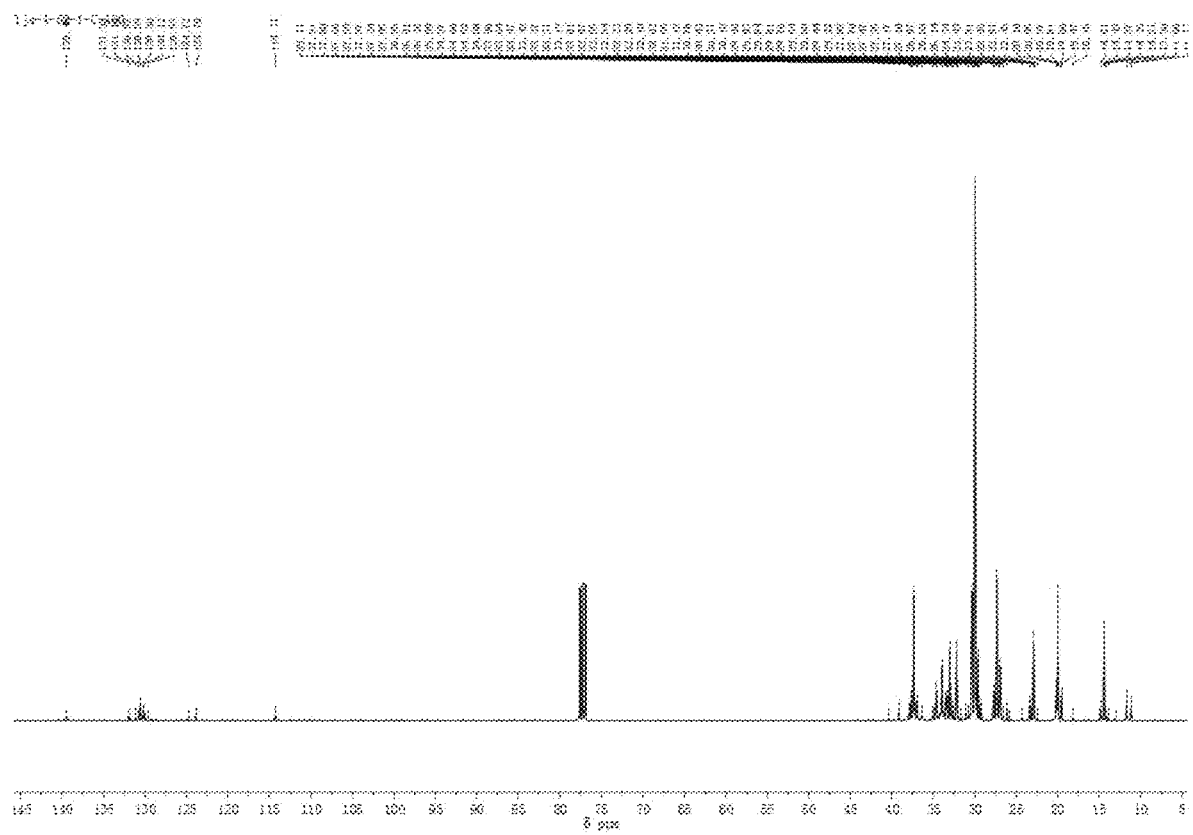
FIG. 1 shows the $^{13}C$ NMR spectrum of the polymer prepared in Example 125 of the present invention.
Figure 2:
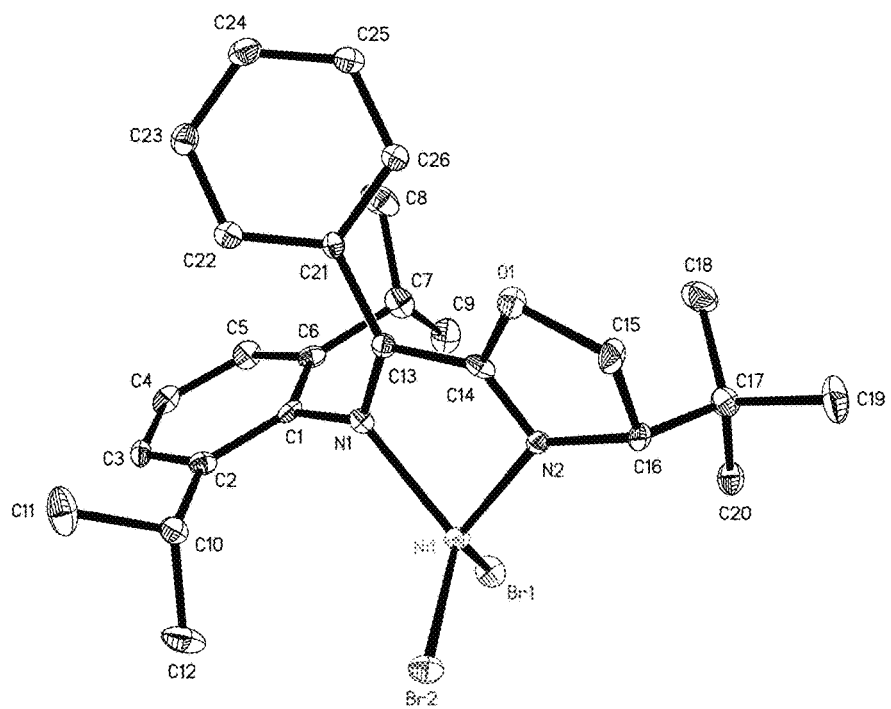
FIG. 2 shows the molecular structure of the complexes 2-9 of Example 57 of the present invention.

After extensive and deeply studies, the present inventors have prepared a novel ligand compound, a complex and a catalytic system, thus directly polymerizing non-polar and/or polar olefin monomer comprising functional group to obtain highly branched oily polymer. The catalyst technology of the present invention enables the preparation of a series of clean oily olefin polymers with different viscosities, including polar functional group-containing polyolefin oils, which can significantly reduces the cost of high quality lubricating oils. The inventor has completed the present invention on this basis.

Terms

Unless otherwise indicated, all the chiral centers in each compound of the present invention can be any structure, such as R configuration, S configuration, or racemism.

"Alkyl" means saturated aliphatic hydrocarbon group, including straight chain and branched chain groups containing 1 to 10 carbon atoms, preferably median size alkyl groups having 1 to 6 carbon atoms, such as methyl, ethyl, propyl, 2-propyl, n-butyl, i-butyl, t-butyl, pentyl, and the like, more preferably lower alkyl groups having 1 to 4 carbon atoms, such as methyl, ethyl, propyl, 2-propyl, n-butyl, i-butyl, t-butyl, and the like.

"Alkenyl" means unsaturated aliphatic hydrocarbon group having carbon-carbon double bond (C═C), including straight chain and branched chain groups containing 2-10 (preferably 2-6) carbon atoms.

"Alkynyl" means unsaturated aliphatic hydrocarbon group having carbon-carbon triple bond, including straight chain and branched chain groups containing 2-10 (preferably 2-6) carbon atoms.

"Cycloalkyl" refers to a 3-8 member percarbon monocyclic ring, percarbon 5 member/6 member or 6 member/6 member fused ring or fused ring group in which one or more rings may contain one or multiple double bonds, but none of the rings have fully conjugated n-electron system. Examples of cycloalkyl groups are cyclopropyl, cyclobutyl, cyclopentyl, cyclohexyl, cyclohexadienyl, adamantyl, cycloheptyl, cycloheptatrienyl and the like.

"Carbocycle" means saturated or unsaturated rings of which the ring skeleton are all carbon atoms, wherein one or more rings may contain one or more double bonds.

"Heterocycle" means saturated or unsaturated rings which comprises at least one hetero atom selected from the following group: N, S, O or P, wherein one or more rings may contain one or more double bonds.

"5-7 member monocyclic" refers to a 5-membered to 7-membered monocyclic (only one ring structure) ring which may be a saturated or unsaturated ring, such as cycloalkyl, cycloalkenyl, aromatic ring.

"Bicyclic or tricyclic group" means groups containing two or three ring structures, such as fused, spiro, or bridged ring structures, such as indolyl, quinolyl, and the like. In the present invention, preferred bicyclic or tricyclic groups are 8 to 20 member rings. "Bicyclic or tricyclic group comprising monocycle A" means that one or more rings in bicyclic or tricyclic group is (are) monocyclic ring A.

"Aromatic ring" means aromatic rings having a conjugated n-electron system, including carbocyclic aryl group and heteroaryl group.

"Heteroaryl" means aryl group which comprises one hetero atom as ring atom, and the remaining ring atoms are carbon, wherein the hetero atom comprises the following: oxygen, sulfur, nitrogen. The ring may be 5, 6 or 7 member rings. Examples of heteroaryl groups include, but are not limited to, furyl, thienyl, benzofuranyl, benzothienyl, pyridyl, pyrrolyl, N-alkylpyrrolyl.

"Alkoxy" refers to —O— (alkyl). Representative examples include methoxy, ethoxy, propoxy, butoxy, and the like.

The term "halogen" refers to F, Cl, Br and I.

The ligand compounds of the present invention may contain one or more chiral centers and thus appear in the form of racemates, racemic mixtures, single enantiomers, diastereomeric compounds and single diastereomers. The existence of chiral centers depends on the nature of the various substituents on the molecule. Each chiral center will independently produce two optical isomers, and all possible optical isomers and diastereomeric mixtures and pure or partially pure compounds are included within the scope of the present invention. The present invention encompasses all such isomeric forms of ligand compounds. Some of the ligand compounds of the present invention may exist in tautomeric form with different hydrogen linkages accompanied with one or more double bond shifts.

As used herein, the term "inert solvent" means solvents that do not chemically react with other components with which are to be mixed.

Specifically, in the present invention, structures such as

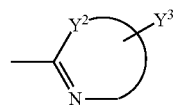

means that $Y^3$ is optional substituent (s) (of which the position and number are not limited), and the position and number of the substituent (s) can be any that conforms to the definition of the present invention and the rule of substitution in the common knowledge in the field.

In the present invention, the "DME" is glycol dimethyl ether; the "⁻OTf" is trifluoromethanesulfonate negative ion; the "⁻OAc" is acetate anion; the "COD" is cyclooctadiene.

Unless otherwise indicated, a hydrogen atom on a "substituted" group is substituted by a substitutent selected from the following groups: C1-C4 alkyl and C1-C4 haloalkyl, halogen, nitro, cyano, $CF_3$, —O—$R_1$, —N($R_2$)$_2$, —Si($R_3$)$_3$, —$CH_2$—O—$R_8$, —$SR_9$ or —$CH_2$—S—$R_{10}$, wherein $R_1$, $R_2$ and $R_3$ are independently C1-C4 alkyl or haloalkyl; while $R_8$, $R_9$ and $R_{10}$ are independently C1-C8 alkyl or phenyl.

As used herein, the term "alkane with multiple ends" means alkyl groups possessing one or more methyl groups, such as t-butyl, i-propyl, and the like.

Ligand Compound

The present invention has provided a ligand compound of formula I.

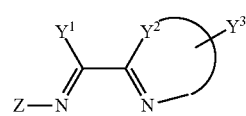

I wherein the remaining groups are defined as above.

Preferably, $Y^1$ is selected from the following group: hydrogen, methyl, trifluoromethyl, n-butyl, n-hexyl, phenyl, C1-C4 alkyl-phenyl; wherein the phenyl may be substituted by alkyl, halogen, alkoxy, C1-C4 amino, nitro, cyano, trimethylsilyl substituted phenyl; aforesaid halogen comprises fluorine, chlorine, bromine and iodine; the alkoxy is preferably methoxy, ethoxy, isopropyl; the alkyl group is preferably C1-C6 alkyl group, more preferably C1-C4 alkyl group, most preferably methyl, ethyl, isopropyl and butyl, and the substituent may on any position of the phenyl which can be replaced.

Preferably, Z is selected from the following group: i-propyl, t-butyl, phenyl, C1-C4 alkyl-phenyl; wherein the phenyl may be substituted by alkyl, halogen, alkoxy, or alkoxyalkyl substituted phenyl; aforesaid halogen comprises fluorine, chlorine, bromine and iodine; the alkoxy is preferably methoxy, ethoxy, isopropyl; the alkyl group is preferably C1-C6 alkyl group, more preferably C1-C4 alkyl group, most preferably methyl, ethyl, isopropyl and butyl, and the substituent may be on any probable position of the phenyl.

Preferably,

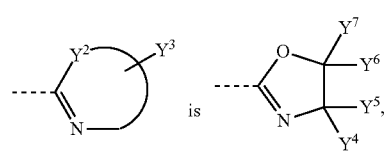

wherein Y⁴, Y⁵, Y⁶, Y⁷ the substituent is C1-C4 alkyl, C1-C4 alkoxy-alkyl, phenyl, C1-C4 alkyl-phenyl, or phenyl substituted by C1-C6 alkyl, halogen, alkoxy; the halogen comprises fluorine, chlorine, bromine and iodine; the alkoxy is preferably methoxy, ethoxy, isopropyl; the alkyl group is preferably C1-C6 alkyl group, more preferably C1-C4 alkyl group, most preferably methyl, ethyl, isopropyl and butyl, and the substituent may be on any probable position of the phenyl.

Or one of Y⁴, Y⁵ forms substituted or unsubstituted phenyl with one of Y⁶ and Y⁷.

Preferably, Y⁴ and Y⁵ together with the adjacent carbon atom can form unsubstituted or substituted C5-C8 saturated carbon ring.

Preferably, Y⁶ and Y⁷ together with the adjacent carbon atom can form unsubstituted or substituted C5-C8 saturated carbon ring.

Preferably,

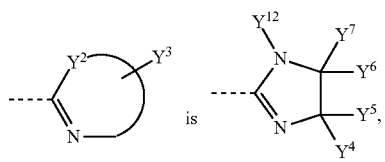

wherein Y⁴, Y⁵, Y⁶, Y⁷ the substituent is isopropyl, tertbutyl, phenyl, or phenyl substituted by C1-C6 alkyl, halogen, alkoxy; the halogen comprises fluorine, chlorine, bromine and iodine; the alkoxy is preferably methoxy, ethoxy, isopropyl; the alkyl group is preferably C1-C6 alkyl group, more preferably C1-C4 alkyl group, most preferably methyl, ethyl, isopropyl and butyl, and the substituent may on any probable position of the phenyl; Y¹² is H, C1-C8 alkyl, C1-C8 haloalkyl, unsubstituted or substituted phenyl, unsubstituted or substituted benzyl. Or one of Y⁴, Y⁵ forms substituted or unsubstituted phenyl with one of Y⁶ and Y⁷.

Preferably, Y⁴ and Y⁵ together with the adjacent carbon atom can form unsubstituted or substituted C5-C8 saturated carbon ring.

Preferably, Y⁶ and Y⁷ together with the adjacent carbon atom can form unsubstituted or substituted C5-C8 saturated carbon ring.

In another preferred embodiment, the compound of formula I has the following structure:

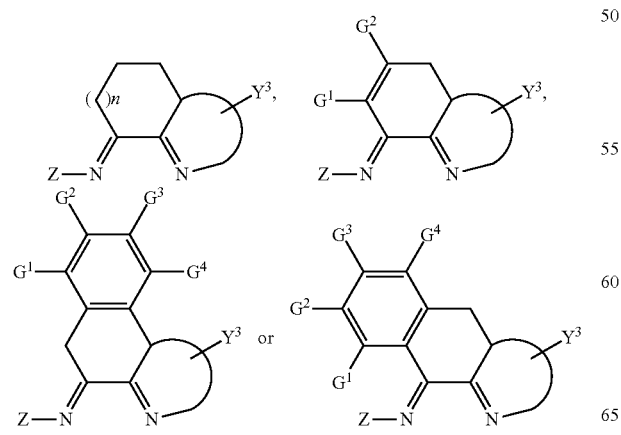

wherein:

Y³, Z, G¹, G², G³ and G⁴ are defined as above;

n is 0, 1, 2, or 3.

The alkyl group may be substituted alkyl group, and preferred substituents are halogen, alkoxy, phenoxy; the halogen includes fluorine, chlorine, bromine or iodine; aforesaid alkoxy is preferably methoxy, ethoxy, isopropoxy, more preferably methoxy.

A particularly preferred ligand includes ligand L1-1 to L1-48 shown in Examples 1 to 48.

In the present invention, the most preferred ligand structure comprises:

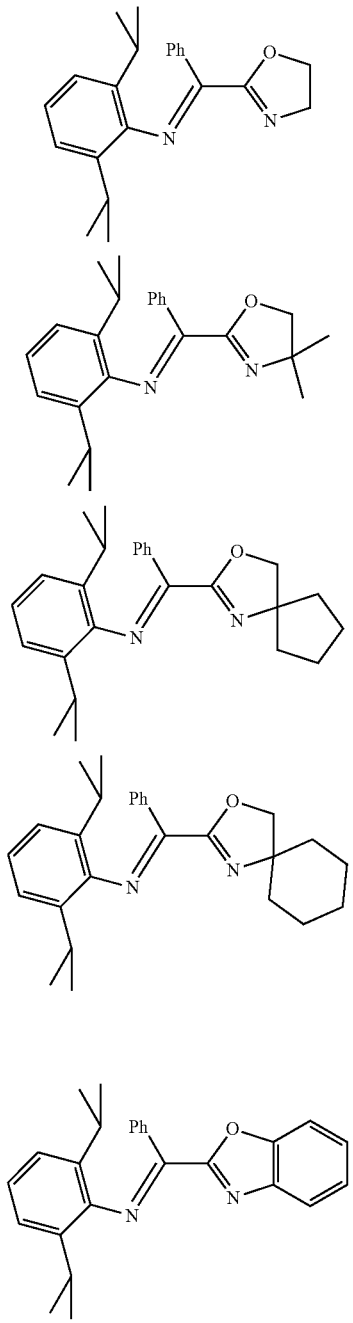

-continued

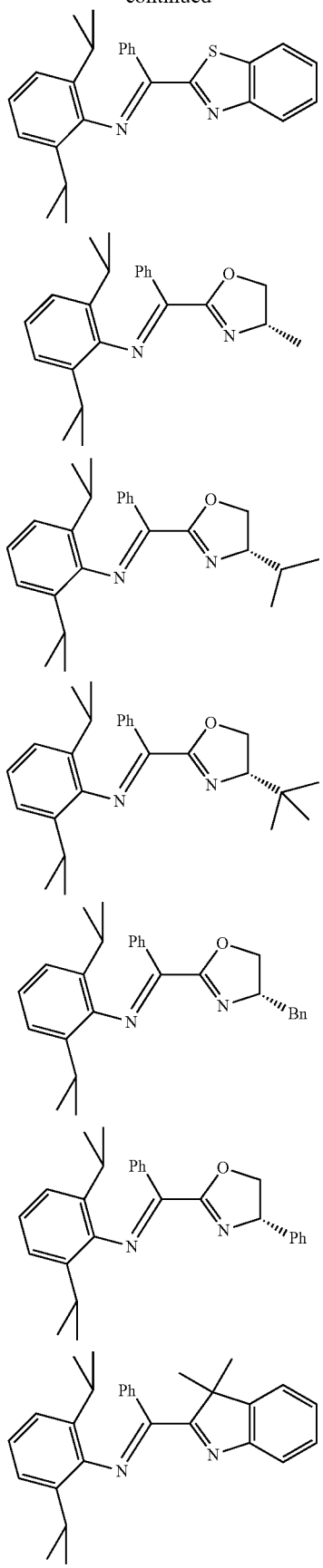

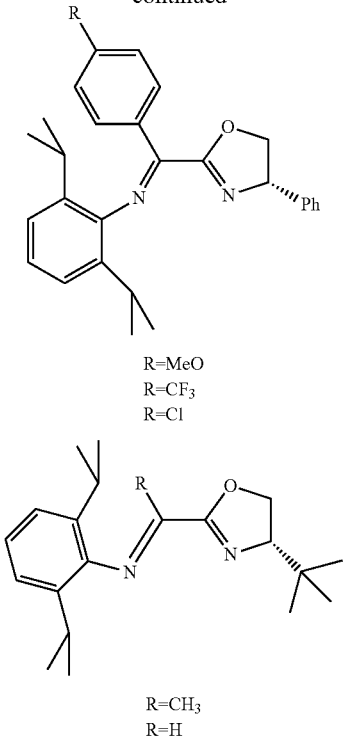

R=MeO
R=CF₃
R=Cl

R=CH₃
R=H

Complex

In the present invention, compounds of formula I could react with divalent nickel or palladium salts to form the corresponding nickel or palladium complex.

In the present invention, the complex of formula II is preferred:

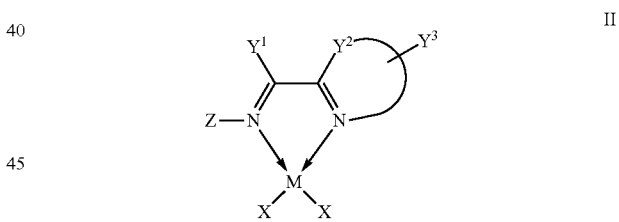

II wherein each group is defined as above.

X may be halogen, C1-C4 alkyl, C2-C6 alkenyl, allyl ( ), benzyl; wherein the C1-C4 alkyl is preferably methyl; the halogen is preferably bromine, chlorine or iodine.

In another preferred embodiment, X is chlorine, bromine, iodine, methyl, allyl ( ) or benzyl.

In another preferred embodiment, X is chlorine, bromine or iodine.

In the present invention, the ligand compound of the present invention could react with a divalent metal precursor, thereby forming the corresponding complex.

In the present invention, the divalent metal precursor include: $NiCl_2$, $NiBr_2$, $NiI_2$, $(DME)NiBr_2$, $(DME)NiCl_2$, $(DME)NiI_2$, $PdCl_2$, $PdBr_2$, $Pd(OTf)_2$ and $Pd(OAc)_2$.

The metal catalyst of the present invention can catalyze the polymerization of ethylene, propylene, butylene, and C4-C20 α-olefins, inner olefins, diolefins or mixtures thereof under the action of co-catalyst to obtain oily polymer; it can also catalyze the co-polymerization of the above olefins such as monoolefins, dienes and the like with polar monomers comprising polar functional group so as to obtain functional polyolefin oil.

Preparation of Ligand Compound and Complex

The present invention also provides the synthesis of the ligand compounds of formula I, comprising the following steps:

(a) oxidization of heterocyclic compound A to give compound B.

(b) treating compound B with amine compound C to give ligand I.

The compound A, B, and C are shown as below:

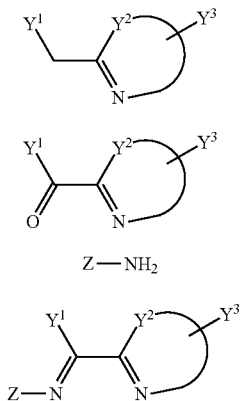

In particular, abstract hydrogen of the heterocyclic compound A by a base in an inert organic solvent, and then oxidization of the resulting anion to form compound B by oxygen, air, or other oxidizing agents. In an inert solvent, compound B condensed with compound C in the presence of a catalyst that promotes the condensation reaction. The inert solvent comprises alcohol, aromatic hydrocarbon, aliphatic hydrocarbon, halogenated hydrocarbon, ether, and ester, preferably aromatic hydrocarbon such as toluene, xylene, trimethylbenzene, and the like. The catalyst for promoting condensation reaction comprises formic acid, acetic acid, p-toluenesulfonic acid, $TiCl_4$, orthosilicate.

Step (a) is preferably carried out in an inert solvent for 3 to 48 hours, respectively.

Preferably, in step (b), 0.001-100% corresponding catalyst (the molar ratio to the reactant) for promoting condensation reaction is added, preferably acetic acid, p-toluenesulfonic acid, $TiCl_4$, or orthosilicate.

In step (b), the ratio of compound B to C is preferably (0.7-1.2):1.

The preferred inert solvent in step (a) is diethyl ether or tetrahydrofuran.

The preferred inert solvent in step (b) is alcohols, aromatic hydrocarbons, aliphatic hydrocarbons, halogenated hydrocarbons, ethers and ester.

Step (b) is directly carried out after the resulting B is separated with or without purification.

The invention also provides a method for preparing complexes. For example, nickel complexes could be synthesized by compound I and metal salts, comprising $NiCl_2$, $NiBr_2$, $NiI_2$ (DME)$NiBr_2$, (DME)$NiCl_2$, or (DME)$NiI_2$ under an anhydrous and anaerobic condition and in inert solvent. The inert solvent used may be any conventional solvent which does not affect the reaction, including alcohols, aromatic hydrocarbons, aliphatic hydrocarbons, halogenated hydrocarbons, ethers, esters, and nitriles, preferably halogenated hydrocarbons. Better results could be obtained in solvent of halogenated hydrocarbon and esters, and preferred examples are methylene chloride, 1,2-dichloroethane, ethyl acetate, tetrahydrofuran.

Wherein, $Y^1$-$Y^{12}$, Z, X are defined as abovementioned. DME refers to ethylene glycol dimethyl ether; when X is a hydrocarbon group, for example methyl or benzyl, the complex usually could be prepared from the corresponding chloride or bromide II with methyl Grignard reagent or benzyl Grignard reagent under the conventional conditions of the similar reaction. No matter what is X (X is halogen, hydrocarbon group or any other group that can coordination with nickel, such as nitrogen-containing compound, oxygen-containing compound), as long as Ni—C bond or Ni—H bond could be formed in the presence of alkyl aluminum, that is, namely the catalysis can be achieved. These compounds have the same active site in catalyzing ethylene polymerization, and thus exhibit the same or similar properties.

Catalytic Systems and Applications

The present invention provides a catalytic system for olefin polymerization to obtain highly branched alkane mixture, and the catalytic system comprises 1) the complexes formed by nickel or palladium metal salt with ligand of formula I; 2) hydrogenation system.

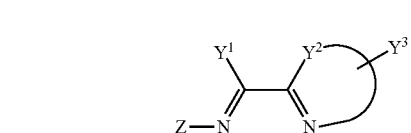

wherein each group is defined as above.

Highly branched alkanes could be prepared directly from ethylene in the presence of both the above polymerization catalytic system and hydrogenation catalyst. The highly branched alkanes mean aliphatic hydrocarbons having the following characteristic: there is 100-500 methyl per 1000 methylene in the polymer chain, and the bromine number is less than 0.5 g/100 g. Typically, the method includes the following two steps:

1) in the presence of the above-mentioned metal complexes and cocatalyst, preparing highly branched oily polyolefin directly from olefin.

2) Hydrogenating the oily polyolefin obtained in step (1) to obtain the hydrogenated oily alkane mixture.

The metal complex is a complex formed by the reaction of compounds of formula I and divalent nickel or palladium, preferably, the metal complex is nickel complexes of formula II.

The co-catalyst is reagents that can promote the polymerization, and may be alkyl aluminum compounds or organic boron reagents.

The alkyl aluminum compound comprises any carbon-aluminum bond-containing compounds, including methylaluminoxane (MAO), modified methylaluminoxane (MMAO), triethylaluminum, triisobutylaluminum, diethylaluminum chloride, ethylaluminum dichloride and so on. Wherein the ratio of aluminum in co-catalyst to nickel or palladium in catalyst is 10 to 5000; methyl aluminoxane or alkyl aluminum reagents herein is co-catalyst to help nickel or palladium complex in catalyzing olefin polymerization to obtain oily polyolefin, and the structure of methyl aluminoxane or alkyl aluminum reagents would not affect the co-catalysis effect, except that the branching degree and the molecular weight of the obtained polymer would be influenced, wherein methylaluminoxane, diethylaluminum chloride, and ethylaluminum dichloride could obtain the best results. In another case, desired results could be obtained with the co-catalysis by $AlCl_3$ alone or together with alkyl aluminum compounds.

In step (1), the metal complex can be preprepared previously, or prepared in situ. That is to say, the metal complex is used in the polymerization system, or the ligand and metal precursor for the preparation of metal complex are used directly so as to form the metal complex in situ during the reaction procedure.

The highly branched polyethylene of the present invention can be hydrogenated to form highly branched alkanes.

The structure of the highly branched polyolefin (such as polyethylene) is determined by $^{13}C$ NMR and comparison of molecular weight measured by HT-GPC and the actual molecular weight measured by laser light scattering. The highly branched alkane is clear and transparent oil with molecular weight of 500-500,000 g/mol.

Depending on the specific requirements, in step (1), the contacting time of ethylene and nickel or palladium complexes and alkyl aluminum compounds in inert solvent can be 0.5 to 72 hours, the reacting temperature range is 0-100° C., and the pressure (gauge pressure) range is 0.1-3 MPa (1-30 atm).

In step (2), the highly branched oily polyethylene obtained in step (1) is treated with reductant, or the oily polyolefin was contacted with hydrogen in the presence of one or more reduction catalyst, to obtain highly branched oily alkane mixture with the bromine number less than 0.5 g/100 g. The reduction catalyst can be any catalyst for promoting the hydrogenation process, preferably, hydrogenation catalysts selected from Pd/C, $Pd(OH)_2$, $PtO_2$, rhodium, nickel, ruthenium and so on. The reduction reagents can be any agent that can reduce a double bond, mainly are borane compound, triethyl silane and so on.

In another preferred embodiment, between step (1) and step (2) further comprised is a step of separating oily polyethylene.

In another preferred embodiment, in step (1), hydrogenation reaction is simultaneously conducted.

In another preferred embodiment, the step (2) may be carried out in an inert solvent or directly be carried out in the oily olefin polymer; the step (1) may be carried out in inert solvent or be carried out in oily olefin polymers (such as oily polyethylene).

Particularly, step (2) can also be completed by the following ways of: a) in step (1), hydrogen is introduced simultaneously to obtain highly branched oily alkane; b) after step (1), the polymerizing system, without processing, is purged with hydrogen, thereby obtaining highly branched oily alkane; c) after step (1), the polymerizing system, without processing, is added with one or more reducing catalyst for hydrogenation, thereby giving highly branched oily alkane; d) after step (1), separating the oily polyethylene and conducting the hydrogenation reaction.

The above reaction can be conducted in an inert solvent, preferably alcohols, alkanes, aromatic hydrocarbons and halogenated hydrocarbons. Of them, in step (1), saturated C5-C12 hydrocarbon is preferred, such as hexane, heptane; halogenated hydrocarbons such as dichloromethane, 1,2-dichloroethane, 1,1,2,2-tetrachloroethane; aromatic hydrocarbons such as toluene, xylene. In step (2), saturated C5-C12 hydrocarbon is preferred, such as hexane, heptane; halogenated hydrocarbons such as dichloromethane, 1,2-dichloroethane, 1,1,2,2-tetrachloroethane; aromatic hydrocarbons such as toluene, xylene.

In addition to non-polar monomer, by modifying the structure of catalysts' substituents, the catalytic system can efficiently catalyze polymerization of polar monomer, or catalyze any combination of polar monomer or non-polar monomer so as to obtain functional oily polymer.

The olefin polymer of the present invention has high branching degree, preferably being dendrimer, or spherical, spherical-like polymer, and the polymer can also be used to obtain highly branched alkane by hydrogenation step (2).

In another preferred embodiment, step (1) further comprises hydrogenation simultaneously; In another preferred embodiment, step (2) may be carried out in an inert solvent or directly be carried out in the oily polyolefin as a solvent; step (1) may be carried out in inert solvent or be carried out in oily polyolefin as a solvent.

In addition to ethylene, the other olefin used in the present invention may be α-olefins or inner olefins, which would not affect the catalytic effect. The inner olefins mean the double bond is at any position other than the end. In the application, the inner olefin can be a mixture of various isomers or a single inner olefin. For example, as for butene, it can be 1-C4, 2-C4, and 2-C4 can be cis-isomer and trans-isomer. When used, it is not limited to 1-C4 or cis-2-C4 or trans-2-C4, and it also can be a mixture of one or more isomer(s), which would not affect the polymerization process.

Oily Polyolefin and Oily Alkane Mixture

Catalysts disclosed in the present invention can be applied to the industrially current-used ethylene, propylene and butane polymerization process, and common reduction process equipment. Both of homogeneous conditions and heterogeneous conditions wherein catalyst loaded on organic or inorganic carriers can be used.

The present invention also provided an oily olefin polymer and the preparation method thereof. The oily polyethylene of the present invention is highly branched; while the highly branched means that the number of methyl in the polyethylene is 100-500 per 1000 methylene.

In the present invention, representative preparation method comprises the following steps (taking ethylene as an example):

(a) under 0-100° C., 0.1 to 3 Mpa (1 to 30 atm), using the complex provided in the present invention to catalyze ethylene polymerization so as to form oily polyethylene.

Preferably, there is cocatalyst in the step; more preferably, the cocatalyst is selected from the following group: alkyl aluminum reagents (such as alkyl aluminoxanes, diethylaluminum chloride and ethylaluminum dichloride); wherein the molar ratio of aluminum in the cocatalyst to nickel in the catalyst is 10-5000.

In another preferred embodiment, step (a) is carried out in the following polymerization solvents: toluene, n-hexane, dichloromethane, 1,2-dichloroethane, chlorobenzene, tetrahydrofuran, or combinations thereof.

In a preferred embodiment, the cocatalyst may be MAO or MMAO, alkyl aluminum or organoboron reagent, wherein the molar ratio of cocatalyst to nickel or palladium in the catalyst is from 10 to 5000.

Since nickel, palladium complex II has the following characteristics in the polymerization process: 1) β-H elimination can be rapidly performed to form polyolefin containing double bond and active species containing Ni (Pd)—H; 2) α-olefin re-coordinate and insertion into Ni (Pd)—H so as to form Ni (Pd)—C bond; (3) the resulted Ni(Pd)—C bond could catalyze ethylene polymerization once more; and (4) finally the catalytic cycle is terminated through P3-H elimination. Therefore, the resulting polymer contains a large number of branches, and the total number of branches can be quantitatively analyzed through $^{13}C$ NMR by estimating the signal of $CH_2$ and $CH_3$ (integral area). And because the termination way of the catalytic cycle is β-H elimination, the polymer contains double bonds.

In the present invention, in step (a) in the representative method, at 0-100° C., at 0.1 to 3 MPa (1 to 30 atm), the complex provided in the present invention can catalyze the polymerization of propylene, butene, or any combination of ethylene, propylene, butene, C4-C20 α-olefin, inner olefin, diene or a mixture thereof, and polar monomer so as to form oily polyolefin with or without functional groups, suitable monomer and catalyst are used to prepare different structures products according to the usage of the oil. The polar group is selected from the following group: carbonyl, hydroxyl, —COOH, ester group —$COOR_{11}$, alkoxy —$OR_{12}$, amido —$NR_{13}R_{14}$, acylamino —$CONR_{15}R_{16}$, thioether —$SR_{17}$, selenide —$SeR_{18}$, —$PR_{19}R_{20}$, —$P(=O)R_{19}R_{20}$ or combinations thereof; wherein $R_{11}$ and $R_{12}$ are independently C1-C10 alkyl or C6-C20 aryl; $R_{13}$, $R_{14}$, $R_{15}$, $R_{16}$, $R_{17}$ or $R_{18}$ are independently hydrogen, C1-C10 alkyl, or C6-C20 aryl; $R_{19}$ or $R_{20}$ are independently C1-C10 alkyl or C6-C20 aryl.

In another preferred embodiment, the polar monomer is selected from the following group:

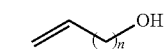

M1: n=1
M2: n=3
M3: n=8

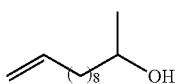

M4

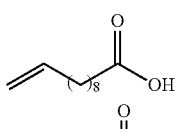

M5

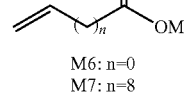

M6: n=0
M7: n=8

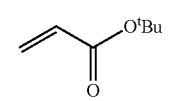

M8

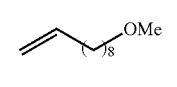

M9

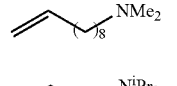

M10

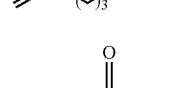

M11

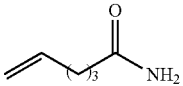

M12

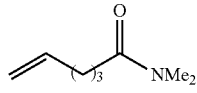

M13

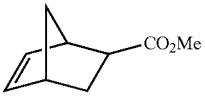

M14

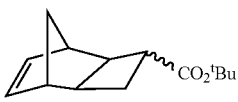

M15

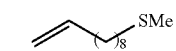

M16

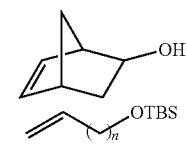

M17

M18: n=1
M19: n=3
M20: n=8

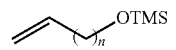

M21: n=1
M22: n=3
M23: n=8

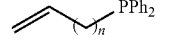

M24: n=4
M25: n=9

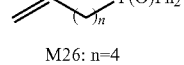

M26: n=4
M27: n=9

Moreover, the method further comprises the following step before step (a): mixing the polar olefin monomer comprising functional group and cocatalyst and using the resulting mixture in step (a);

Or reacting the polar olefin monomer with functional group protecting reagent to form a polar monomer with protected functional groups and then use it in step (a).

In another preferred embodiment, the functional group protecting reagent is selected from the group consisting of: TBS, TES, TBDPS, TMS, $AlEt_3$, $Al^iBu_3$, methylaluminoxane, ethylaluminoxane, butylalumoinxane, MMAO, and combinations thereof.

In another preferred embodiment, the cocatalyst is selected from the group consisting of: alkyl aluminum reagent, alkyl aluminoxane reagent, weakly coordinating anion, and combinations thereof.

In another preferred embodiment, the alkyl aluminum reagent is selected from the group consisting of: $AlMe_3$, $AlEt_3$, $Al^iBu_3$, or $AlEt_2Cl$.

In another preferred embodiment, the alkyl aluminoxane reagent is selected from the following group: MMAO or MAO.

In another preferred embodiment, the weakly coordinating anion is selected from the following group: $[B(3,5-(CF_3)_2C_6H_3)_4]^-$ or $^-OSO_2CF_3$.

In another preferred embodiment, the "MMAO" refers to modified methyl aluminoxane (from Akzo Chemical Company).

In another preferred embodiment, the olefin is polar olefin monomers which comprise functional groups, non-polar monomers, or combinations thereof.

In another preferred embodiment, the non-polar monomer comprises: ethylene, propylene, butene, or combinations thereof.

In another preferred embodiment, the olefins are any combination of ethylene, propylene and/or butene with other C5-C20 olefins.

In another preferred embodiment, the oily olefin polymer is highly branched; more preferably, the highly branched means that the number of methyl in the polymer corresponding to 1000 $CH_2$ is 100-500.

In another preferred embodiment, the cocatalyst is used in step (a).

More preferably, the cocatalyst is selected from the following group or combinations thereof: alkyl aluminum compound: alkyl aluminum reagents (such as alkyl aluminoxanes, diethylaluminum chloride and ethylaluminum dichloride).

In another preferred embodiment, the reaction temperature of step (a) is 0-100° C.

In another preferred embodiment, the reaction conditions of step (a) are: pressure (gauge pressure) 0.1-3 MPa, the cocatalyst is alkyl aluminoxane or diethylaluminum chloride, wherein the molar ratio of aluminum of cocatalyst to catalyst is 10-5000.

In another preferred embodiment, step (a) is carried in the following solvents: toluene, n-hexane, dichloromethane, 1,2-dichloroethane, chlorobenzene, tetrahydrofuran, or combinations thereof.

In another preferred embodiment, step (a) may be carried out in oily polyethylene or oily alkane mixture.

In another preferred embodiment, the method further comprises the following steps:

(b) hydrogenating the oily polyolefin obtained in step (a) to obtain a hydrogenated oily alkane mixture.

In another preferred embodiment, the bromine value of the oily alkane mixture is less than 0.5 g/100 g.

In another preferred embodiment, between step (a) and step (b) further comprised is a step of separating oily polyolefin.

In another preferred embodiment, in step (a), hydrogenation reaction is simultaneously conducted.

In another preferred embodiment, the step (b) may be carried out in an inert solvent or directly be carried out in the oily polyolefin.

In another preferred embodiment, the oily alkane mixture is the hydrogenation product of the oily polyolefin of the invention.

In another preferred embodiment, the oily alkane mixture is the hydrogenation product of the oily polyethylene of the invention.

In another preferred embodiment, the oily olefin polymer or a hydrogenated product thereof possesses one or more of the following characteristics:

(i) the number of polar group in the polymer chain: 0.1-1000 polar groups per 1000 carbon, preferably 5-200, more preferably 5-50;

(ii) the number of methyl in the polymer is 100-500 methyl per 1000 methylene;

(iii) the molecular weight is 300-500,000 g/mol;

(iv) the density is 0.75-0.91 g/mol.

In another preferred embodiment, the oily means that the olefin polymer is a colorless transparent oil with good mobility within all or part of the temperature range −50° C. to 70° C. (preferably over −40° C. to 50° C., more preferably −40° C. to 35° C.).

The present invention also provides a class of highly branched oily alkane mixtures which are hydrogenated products of the oily polyolefins of the present invention, wherein the oily polyolefin comprises oily polyethylene, oily polypropylene, oily polybutene or oily copolymer obtained by the reaction of the olefins mixture of the above in the presence of a catalyst. The molecular weight of the oily alkane mixture is 500-500,000 g/mol, and the number of methyl ($CH_3$) per 1000 methylene ($CH_2$) is 100-500. In another preferred embodiment, the molecular weight of the oily alkane mixture is 500-50,000 g/mol, more preferably, the molecular weight of the oily alkane mixture is 500-10,000 g/mol, and the number of methyl ($CH_3$) per 1000 methylene ($CH_2$) is 100-300, and the pour point is below −20° C.

In another preferred embodiment, the oily olefin polymer or a hydrogenated product thereof possesses one or more of the following characteristics:

(i) the number of the methyl in the polymer is 100-500 methyl per 1000 methylene;

(ii) the molecular weight is 300-500,000 g/mol;

(iii) the density is 0.75-0.91 g/mol.

In another preferred embodiment, the number of methyl in the oily olefin polymer or a hydrogenated product thereof per 1000 methylene is 100-300, and preferably 150-300.

In another preferred embodiment, the number of branched chain in the oily olefin polymer or a hydrogenated product thereof per 1000 methylene is 100-300, and preferably 150-300. Wherein the branched chain comprises methyl, ethyl, n-propyl, n-butyl, sec-butyl and other branched chain with four or more (preferably 4-8) carbons.

In another preferred embodiment, there are 40-70 branched alkyl chains with multiple ends per 1000 carbons.

In another preferred embodiment, the polymer has a branch of the following structure: straight or branched C3-C8 alkyl.

In another preferred embodiment, the branched alkyl chains with multiple ends of the polymer is sec-butyl, and the number of sec-butyl corresponding to 1000 carbon is 15-30.

In another preferred embodiment, 'oily' means that the olefin polymer is oily within all or part of the temperature range over −50° C. (preferably −40° C. to 50° C., more preferably −40° C. to 35° C.).

In another preferred embodiment, the 100° C. kinematic viscosity of the oily olefin polymer or hydrogenated products thereof obtained in the present invention is 4-50 $mm^2/s$, viscosity index (VI) is 160-300, and the surface tension is over 20 mM/m. The test method of the kinematic viscosity is as GB/T 265-1988 (2004), and the test method of viscosity index (VI value) is as GB/T 1995-1998 (2004).

In another preferred embodiment, the hydrogenated product of the oily olefin polymer obtained by the present invention possesses excellent oxidative stability (over 50 min). Oxidation stability is tested according to SH/T 0193-2008 (rotating bomb method).

In preferred embodiments of the present invention, the resulting oily olefin mixture is a colorless and transparent liquid at temperatures over pour point. In an inert atmosphere, it may be stable at high temperature, preferably higher than 300° C. (no oxidation reactions or the like may occur).

In order to improve corresponding physical properties of highly branched saturated alkanes, such highly branched saturated alkanes may be mixed with various additives or reinforcing agents during use, such as antifreeze, alkylnaphthalene, and the like. In addition, such highly branched saturated alkanes can also be used as additives to improve the process ability of the resin, for example as a plasticizer in the process of polymer processing. In another preferred embodiment, the lubricating oil contains 0.1 to 100 wt % (preferably 1 to 90 wt %) of oily alkane mixture.

During the polymerization, the metal complex can be prepared in situ. That is, (i) the desired ligand and metal salt are added into the organic solvent successively; (ii) after the reaction solution is stirred for 0-72 h, all or part of the solution is contacted with the olefin alone or together with the cocatalyst to catalyze the polymerization of the olefin to obtain oily polymer; or when the partial or total olefin monomer contains polar functional groups, the method further comprises the following before the step (i): Mixing aforesaid polar olefin monomer and cocatalyst to form a mixture, and then applying aforesaid mixture to step (i); or aforesaid polar olefin monomer to react with a functional group protecting agent to form functional group protected polar olefin monomer, and then using the protected polar olefin monomer in step (i).

Whether the metal complex is prepared in situ or the metal complex is prepared and separated before the polymerization, the polymerization effect will not be affected. The same product can be obtained under the same polymerization process and polymerization conditions.

Main Advantages of the Present Invention are:

(a) New catalyst system can be used to achieve the direct preparation of oily alkane of high branching degree from simple olefin monomer, such as ethylene, and the cost is significantly reduced.

(b) The catalyst system of the present invention can catalyze the polymerization of the polar olefin monomer containing functional groups, thus the obtained olefin polymer comprising various polar groups, which can be used in different applications.

(c) The highly branched alkane mixture disclosed in the present invention has low bromine value and high viscosity index, which can be used as base oil or a processing aid for use in advanced lubricating oils.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are weight parts and weight percentage.

The kinetic test showed that the catalyst is stable and the activity almost kept unattenuated at least 3 hours.

It can be seen from the $^{13}C$ spectrum that there are various types of branches, and the analysis of specific branches can refer to reference: Galland, G. B.; de Souza, R. F.; Mauler, R. S.; Nunes, F. F. *Macromolecules* 1999, 32, 1620. and Wiedemann, T.; Voit, G.; Tchernook, A.; Roesle, P.; Gottker-Schnetmann, I.; Mecking, S. *J. Am. Chem. Soc.* 2014, 136, 2078.

Preparation of Ligand

Example 1

Synthesis of Ligand L1-1

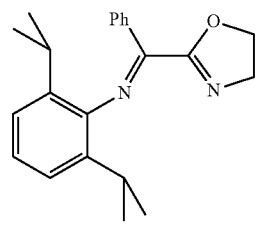 [SMILES: CC(C)c1cccc(C(C)C)c1/N=C(/C1=NCCO1)c1ccccc1]

(1) phenylacetic acid (2.72 g, 20 mmol), ethanolamine (1.22 g, 20 mmol), xylenes (50 mL) were added into a 100 mL egg-shaped flask, and refluxed to remove water at 170° C. The reaction was tracked by NMR-monitoring, then concentrated by rotary evaporation and distilled under reduced pressure to obtain 2-benzyl-4,5-dihydrooxazole as a pale yellow liquid, yield 63%. $^1H$ NMR (300 MHz, $CDCl_3$): δ=7.31-7.24 (5H, m), 4.22 (2H, t), 3.82 (2H, t), 3.60 (2H, s).

(2) 100 mL dried reaction flask was added with dried tetrahydrofuran (50 mL) and diisopropylamine (1.70 mL, 12 mmol), and 2.4 M of n-butyllithium (5 mL, 12 mmol) was added dropwise in an ice-bath, and reacted at room temperature for 2 hours after completion of the addition. Then 2-benzyl-4,5-dihydro-oxazole (1.61 g, 10.0 mmol) in tetrahydrofuran was added dropwise by syringe pump into a prepared LDA solution in a dry ice-acetone bath, and reacted in dry ice-acetone bath for 3 hours after the addition was finished, finally replenished with oxygen in the dry ice-acetone bath for 3 hours, and TLC tracked until the reaction was completed. The reaction was quenched by adding saturated sodium thiosulfate solution, extracted with ether, dried over anhydrous sodium sulfate, filtered and concentrated by rotary evaporation. The reaction mixture was purified by silica gel column chromatography (triethylamine embellished, ethyl acetate/petroleum ether=1/20) to give 2-benzoyl-4,5-dihydrooxazole, and the product was a yellow liquid, yield 71%. $^1H$ NMR (400 MHz, $CDCl_3$): δ=8.31 (2H, dd), 7.63 (1H, m), 7.49 (2H, m), 4.49 (1H, dd), 4.20 (1H, dd), 3.74 (2H, m).

(3) 2-benzoyl-4,5-dihydrooxazole (0.88 g, 5.0 mmol), dichloromethane (25 mL), titanium tetrachloride (0.6 mL, 5.5 mmol) and 2,6-diisopropyl aniline (0.94 mL, 5.0 mmol) were added into 50 mL of the reaction tube, and triethylamine (1.05 mL, 7.5 mmol) was added, TLC tracked until the reaction was completed. The reaction was quenched by adding saturated sodium bicarbonate solution, filtered through diatomaceous earth, extracted with dichloromethane, dried over anhydrous sodium sulfate, suction filtered, concentrated by rotation, and purified through neutral alumina column chromatography (ethyl acetate/petroleum ether=1/30) to give the crude product, and ligand L1-1 was obtained by recrystallization with methanol, which is a yellow solid, yield 38%. $^1H$ NMR (400 MHz, $CDCl_3$): δ=8.01 (2H, dd), 7.50 (3H, m), 7.05 (3H, m), 4.56 (0.5H, t), 4.18 (0.5H, t), 4.01 (1.5H, t), 3.82 (1.5H, t), 2.86 (2H, m), 1.19 (4.5H, d), 1.14 (1.5H, d), 1.11 (4.5H, d), 0.86 (1.5H, d).

In examples 2-48, different racemic or optically pure raw materials were used to replace the corresponding raw material in example 1 so as to prepare ligand L1-2 to L1-48, and the results are shown in table 1.

TABLE 1

| Example No. | | The structure of the ligand: | Structural characterization (H NMR spectroscopy or elemental analysis) |
|---|---|---|---|
| 2 | L1-2 | | ¹H NMR (400 MHz, CDCl₃): δ = 8.00 (2 H, d), 7.50(3 H, m), 7.05 (3 H, m), 3.68 (2 H, s), 2.89 (2 H, m), 1.21 (6 H, d), 1.09 (12 H, d). |
| 3 | L1-3 | | ¹H NMR (400 MHz, CDCl₃): δ = 7.98 (2 H, d), 7.52(3 H, m), 7.05 (3 H, m), 3.83 (2 H, s), 2.87 (2 H, m), 1.34 (4 H, q), 1.21 (6 H, d), 1.09 (6 H, d), 0.90 (6 H, t). |
| 4 | L1-4 | | ¹H NMR (400 MHz, CDCl₃): δ = 8.00 (2 H, d), 7.50(3 H, m), 7.05 (3 H, m), 3.68 (2 H, s), 2.89 (2 H, m), 1.21 (6 H, d), 1.09 (12 H, d). |
| 5 | L1-5 | | ¹H NMR (400 MHz, CDCl₃): δ = 8.00 (2 H, d), 7.49(3 H, m), 7.05 (3 H, m), 3.71 (2 H, s), 2.89 (2 H, m), 1.64-1.08 (22 H, m). |
| 6 | L1-6 | | ¹H NMR (400 MHz, CDCl₃): δ = 7.91 (2 H, d), 7.50(1 H, t), 7.43(2 H, t), 7.20 (6 H, m), 7.10 (3 H, m), 6.95 (4 H, dd), 4.60 (2 H, s), 2.93 (2 H, dt), 1.10 (12 H, dd). |
| 7 | L1-7 | | ¹H NMR (400 MHz, CDCl₃): δ = 8.01 (2 H, dd), 7.51(3 H, m), 7.05 (3 H, m), 4.15(2 H, ddd), 3.51 (2 H, dd), 2.89 (2 H, m), 1.21 (6H, dd), 1.10 (6 H, dd), 0.97. (3H, d). |
| 8 | L1-8 | | ¹H NMR (400 MHz, CDCl₃): δ = 7.99 (2 H, dd), 7.48(3 H, m), 7.03 (3 H, m), 4.13(1 H, t), 3.90 (1 H, dd), 3.71 (1 H, t), 2.89 (2 H, m), 1.42 (1H, m), 1.15 (12 H, ddd), 0.67 (6H, m). |

TABLE 1-continued

| Example No. | | The structure of the ligand: | Structural characterization (H NMR spectroscopy or elemental analysis) |
|---|---|---|---|
| 9 | L1-9 | | $^1$H NMR (400 MHz, CDCl$_3$): δ = 7.97 (2 H, d), 7.49(3 H, m), 7.02 (3 H, m), 4.13 (1 H, dd), 3.87 (2 H, dt), 2.89 (2 H, m), 1.15 (12 H, ddd), 0.60 (9 H, s). |
| 10 | L1-10 | | $^1$H NMR (400 MHz, CDCl$_3$): δ = 8.05 (2 H, d), 7.52(3 H, m), 7.15(6 H, m), 6.59 (2 H, d), 5.21 (1 H, t), 4.54 (1 H, t), 3.85 (1 H, t), 2.92 (2 H, dq), 1.12 (12 H, m). |
| 11 | L1-11 | | $^1$H NMR (400 MHz, CDCl$_3$): δ = 7.96 (2 H, dd), 7.48(3 H, m), 7.12 (3 H, m), 7.06 (6 H, m), 4.34(1 H, dd), 3.99 (1 H, t), 3.72 (1 H, t), 2.85 (3 H, m), 2.10 (1 H, dd), 1.21 (6 H, dd), 1.11 (6 H, dd). |
| 12 | L1-12 | | Anal. Calcd. For C$_{20}$H$_{30}$N$_2$O: C, 76.39; H, 9.62; N, 8.91. Found: C, 76.02; H, 9.60; N, 8.64. |
| 13 | L1-13 | | Anal. Calcd. For C$_{21}$H$_{32}$N$_2$O: C, 76.78; H, 9.82; N, 8.53. Found: C, 76.37; H, 9.59; N, 8.38. |
| 14 | L1-14 | | Anal. Calcd. For C$_{24}$H$_{38}$N$_2$O: C, 77.79; H, 9.62; N, 7.56. Found: C, 77.82; H, 10.60; N, 7.64. |

TABLE 1-continued

| Example No. | The structure of the ligand: | Structural characterization (H NMR spectroscopy or elemental analysis) |
|---|---|---|
| 15 | L1-15 | Anal. Calcd. For $C_{27}H_{36}N_2O$: C, 80.15; H, 8.97; N, 6.92. Found: C, 79.89; H, 9.10; N, 6.75. |
| 16 | L1-16 | Anal. Calcd. For $C_{27}H_{36}N_2O_2$: C, 77.10; H, 8.63; N, 6.66. Found: C, 77.01; H, 8.42; N, 6.49. |
| 17 | L1-17 | Anal. Calcd. For $C_{28}H_{39}N_3O$: C, 77.55; H, 9.07; N, 9.69. Found: C, 77.23; H, 8.94; N, 9.47. |
| 18 | L1-18 | Anal. Calcd. For $C_{26}H_{33}ClN_2O$: C, 73.48; H, 7.83; N, 6.59. Found: C, 73.09; H, 7.60; N, 6.57. |

TABLE 1-continued

| Example No. | The structure of the ligand: | Structural characterization (H NMR spectroscopy or elemental analysis) |
|---|---|---|
| 19 | L1-19 | Anal. Calcd. For $C_{26}H_{33}N_3O_3$: C, 71.70; H, 7.64; N, 9.65. Found: C, 71.51; H, 7.42; N, 9.45. |
| 20 | L1-20 | Anal. Calcd. For $C_{27}H_{33}F_3N_2O$: C, 70.72; H, 7.25; N, 6.11. Found: C, 70.54; H, 7.02; N, 6.05. |
| 21 | L1-21 | Anal. Calcd. For $C_{27}H_{33}N_3O$: C, 78.03; H, 8.00; N, 10.11. Found: C, 77.93; H, 8.04; N, 9.97. |
| 22 | L1-22 | Anal. Calcd. For $C_{29}H_{42}N_2OSi$: C, 75.27; H, 9.07; N, 6.05. Found: C, 75.23; H, 8.87; N, 5.95. |
| 23 | L1-23 | Anal. Calcd. For $C_{20}H_{22}N_2O$: C, 78.40; H, 7.24; N, 9.14. Found: C, 78.21; H, 6.98; N, 9.03. |

TABLE 1-continued

| Example No. | The structure of the ligand: | Structural characterization (H NMR spectroscopy or elemental analysis) |
|---|---|---|
| 24 | L1-24 | Anal. Calcd. For $C_{22}H_{26}N_2O$: C, 79.00; H, 7.84; N, 8.38. Found: C, 78.76; H, 7.91; N, 8.28. |
| 25 | L1-25 | Anal. Calcd. For $C_{20}H_{20}F_2N_2O$: C, 70.16; H, 5.89; N, 8.18. Found: C, 70.21; H, 6.04; N, 8.15. |
| 26 | L1-26 | Anal. Calcd. For $C_{20}H_{20}Cl_2N_2O$: C, 64.01; H, 5.37; N, 7.46. Found: C, 63.91; H, 5.04; N, 7.21. |
| 27 | L1-27 | Anal. Calcd. For $C_{20}H_{20}Br_2N_2O$: C, 51.75; H, 4.34; N, 6.03. Found: C, 51.21; H, 4.15; N, 6.00. |
| 28 | L1-28 | Anal. Calcd. For $C_{27}H_{36}N_2O$: C, 80.15; H, 8.97; N, 6.92. Found: C, 79.92; H, 8.78; N, 6.40. |
| 29 | L1-29 | Anal. Calcd. For $C_{18}H_{26}N_2O$: C, 75.48; H, 9.15; N, 9.78. Found: C, 75.21; H, 8.98; N, 9.32. |
| 30 | L1-30 | Anal. Calcd. For $C_{26}H_{26}N_2O$: C, 81.64; H, 6.85; N, 7.32. Found: C, 81.21; H, 6.57; N, 7.08. |

TABLE 1-continued

| Example No. | | The structure of the ligand: | Structural characterization (H NMR spectroscopy or elemental analysis) |
|---|---|---|---|
| 31 | L1-31 | (structure) | Anal. Calcd. For $C_{28}H_{28}N_2O$: C, 82.32; H, 6.91; N, 6.86. Found: C, 82.15; H, 6.59; N, 6.35. |
| 32 | L1-32 | (structure) | Anal. Calcd. For $C_{29}H_{32}N_2$: C, 85.25; H, 7.89; N, 6.86. Found: C, 84.89; H, 7.42; N, 6.43. |
| 33 | L1-33 | (structure) | Anal. Calcd. For $C_{24}H_{31}N_3$: C, 79.73; H, 8.64; N, 11.62. Found: C, 79.38; H, 8.28; N, 11.53. |
| 34 | L1-34 | (structure) | Anal. Calcd. For $C_{27}H_{29}N_3$: C, 81.99; H, 7.39; N, 10.62. Found: C, 81.86; H, 7.17; N, 10.30. |
| 35 | L1-35 | (structure) | Anal. Calcd. For $C_{34}H_{33}N_3$: C, 84.43; H, 6.88; N, 8.69. Found: C, 84.14; H, 6.56; N, 8.14. |
| 36 | L1-36 | (structure) | Anal. Calcd. For $C_{26}H_{34}N_2S$: C, 76.80; H, 8.43; N, 6.89. Found: C, 76.42; H, 8.35; N, 6.51. |

TABLE 1-continued
| Example No. | The structure of the ligand: | Structural characterization (H NMR spectroscopy or elemental analysis) |
|---|---|---|
| 37 | L1-37 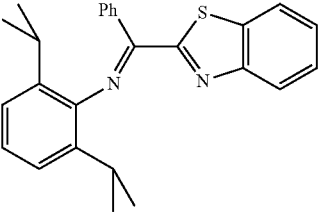 [SMILES: CC(C)c1cccc(C(C)C)c1/N=C(\c1ccccc1)c1nc2ccccc2s1] | Anal.Calcd. For $C_{26}H_{26}N_2S$: C, 78.35; H, 6.88; N, 7.03. Found: C, 78.04; H, 6.27; N, 6.96. |
| 38 | L1-38 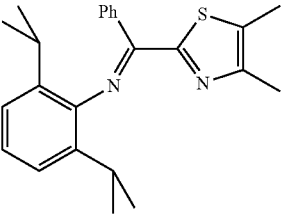 [SMILES: Cc1nc(/C(=N/c2c(C(C)C)cccc2C(C)C)c2ccccc2)sc1C] | Anal. Calcd. For $C_{24}H_{28}N_2S$: C, 76.55; H, 7.49; N, 7.44. Found: C, 76.42; H, 7.37; N, 7.25. |
| 39 | L1-39 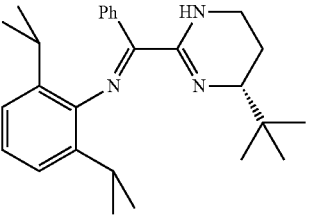 | Anal. Calcd. For $C_{27}H_{37}N_3$: C, 80.35; H, 9.24; N, 10.41. Found: C, 80.14; H, 9.05; N, 10.12. |
| 40 | L1-40 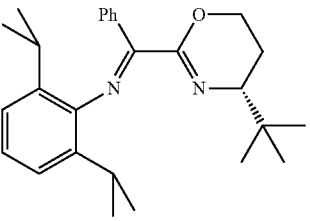 | Anal. Calcd. For $C_{27}H_{36}N_2O$: C, 80.15; H, 8.97; N, 6.92. Found: C, 79.91; H, 8.56; N, 6.64. |
| 41 | L1-41 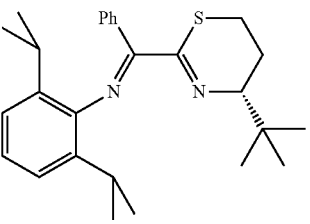 [SMILES: CC(C)c1cccc(C(C)C)c1/N=C(/C1=N[C@@H](C(C)(C)C)CCS1)c1ccccc1] | Anal. Calcd. For $C_{27}H_{36}N_2S$: C, 77.09; H, 8.63; N, 6.66. Found: C, 76.87; H, 8.56; N, 6.37. |
| 42 | L1-42 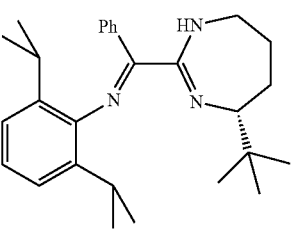 [SMILES: CC(C)c1cccc(C(C)C)c1/N=C(/C1=N[C@@H](C(C)(C)C)CCCN1)c1ccccc1] | Anal. Calcd. For $C_{28}H_{39}N_3$: C, 80.53; H, 9.41; N, 10.06. Found: C, 80.24; H, 9.09; N, 10.01. |

TABLE 1-continued

| Example No. | | The structure of the ligand: | Structural characterization (H NMR spectroscopy or elemental analysis) |
|---|---|---|---|
| 43 | L1-43 | | Anal. Calcd. For $C_{28}H_{38}N_2O$: C, 80.34; H, 9.15; N, 6.69. Found: C, 79.95; H, 8.86; N, 6.54. |
| 44 | L1-44 | | Anal. Calcd. For $C_{28}H_{38}N_2S$: C, 77.37; H, 8.81; N, 6.44. Found: C, 76.93; H, 8.56; N, 6.02. |
| 45 | L1-45 | | Anal. Calcd. For $C_{23}H_{35}N_3$: C, 78.14; H, 9.98; N, 11.89. Found: C, 77.94; H, 9.69; N, 11.56. |
| 46 | L1-46 | | Anal. Calcd. For $C_{23}H_{33}N_3$: C, 78.58; H, 9.46; N, 11.95. Found: C, 78.31; H, 9.08; N, 11.50. |
| 47 | L1-47 | | Anal. Calcd. For $C_{22}H_{26}N_2O_2$: C, 75.40; H, 7.48; N, 7.99. Found: C, 75.05; H, 7.12; N, 7.54. |
| 48 | L1-48 | | Anal. Calcd. For $C_{24}H_{30}N_2O_2$: C, 76.16; H, 7.99; N, 7.40. Found: C, 75.83; H, 7.48; N, 7.03. |

Preparation of Complex

Example 49

Synthesis of Complex 2-1

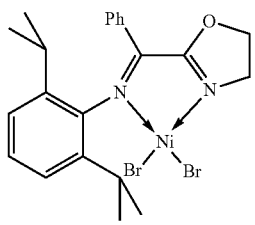

NiBr$_2$ (DME) 1 mmol and 1.05 mmol L1-1 were mixed and the reaction system was replaced by nitrogen for three times, and 20 mL of anhydrous dichloromethane was added and stirred overnight. The reaction solution was filtered, the solvent of filtrate was removed under reduced pressure, and the solid was washed for 2-3 times with solvent mixture of dichloromethane/n-hexane (2 mL/20 mL). After filtration, the remaining solid was dried under vacuum. The product is a red solid, yield 87%. Anal. Calcd. For $C_{22}H_{26}Br_2N_2NiO$: C, 47.79; H, 4.74; N, 5.07. Found: C, 48.04; H, 4.65; N, 4.95.

In examples 50-103, different ligand or metal precursor were used to replace the corresponding ligand or metal precursor in example 49 so as to prepare complex 2-2 to 2-55, and the results are shown in table 2.

TABLE 2

| Example | No. | Structure | elemental analysis |
|---|---|---|---|
| 50 | 2-2 | 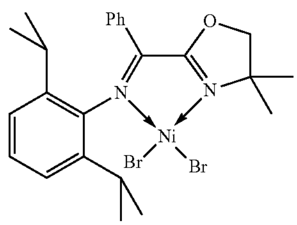 | Anal. Calcd. For $C_{24}H_{30}Br_2N_2NiO$: C, 49.61; H, 5.20; N, 4.82. Found: C, 50.01; H, 5.60; N, 4.64. |
| 51 | 2-3 | 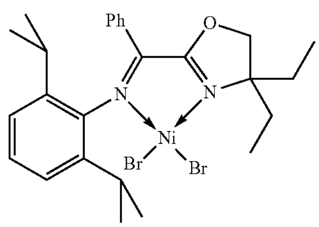 | Anal. Calcd. For $C_{26}H_{34}Br_2N_2NiO$: C, 51.27; H, 5.63; N, 4.60. Found: C, 51.06; H, 5.32; N, 4.45. |
| 52 | 2-4 | 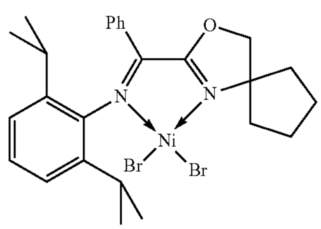 | Anal. Calcd. For $C_{26}H_{32}Br_2N_2NiO$: C, 51.44; H, 5.31; N, 4.61. Found: C, 51.13; H, 5.07; N, 4.35. |
| 53 | 2-5 | 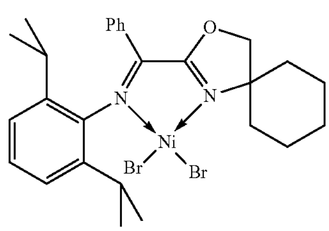 | Anal. Calcd. For $C_{27}H_{34}Br_2N_2NiO$: C, 52.21; H, 5.52; N, 4.51. Found: C, 51.95; H, 5.22; N, 4.28. |
| 54 | 2-6 | 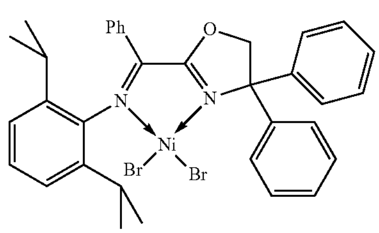 | Anal. Calcd. For $C_{34}H_{34}Br_2N_2NiO$: C, 57.91; H, 4.86; N, 3.97. Found: C, 57.49; H, 4.32; N, 3.45. |

TABLE 2-continued

| Example | No. | Structure | elemental analysis |
|---|---|---|---|
| 55 | 2-7 | 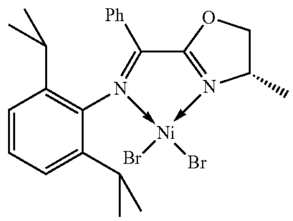 | Anal. Calcd. For $C_{23}H_{28}Br_2N_2NiO$: C, 48.72; H, 4.98; N, 4.94. Found: C, 48.36; H, 4.62; N, 4.58. |
| 56 | 2-8 | 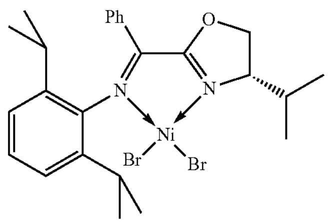 | Anal. Calcd. For $C_{25}H_{32}Br_2N_2NiO$: C, 50.46; H, 5.42; N, 4.71. Found: C, 50.23; H, 5.22; N, 4.32. |
| 57 | 2-9 | 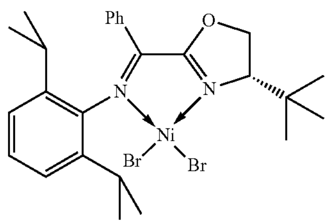 | Anal. Calcd. For $C_{26}H_{34}Br_2N_2NiO$: C, 51.27; H, 5.63; N, 4.60. Found: C, 50.86; H, 5.37; N, 4.40. |
| 58 | 2-10 | 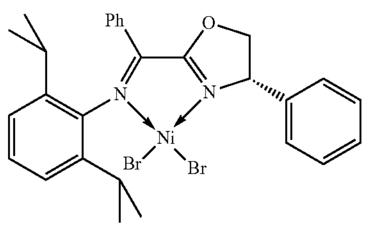 | Anal. Calcd. For $C_{28}H_{30}Br_2N_2NiO$: C, 53.46; H, 4.81; N, 4.45. Found: C, 53.02; H, 4.42; N, 4.13. |
| 59 | 2-11 | 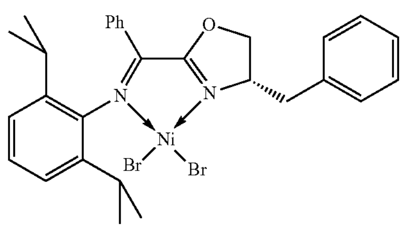 | Anal. Calcd. For $C_{29}H_{32}Br_2N_2NiO$: C, 54.16; H, 5.02; N, 4.36. Found: C, 53.85; H, 4.62; N, 4.10. |
| 60 | 2-12 | 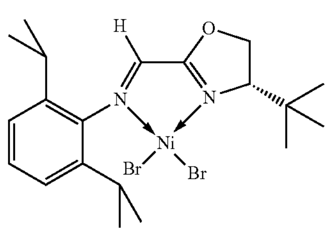 | Anal. Calcd. For $C_{20}H_{30}Br_2N_2NiO$: C, 45.07; H, 5.67; N, 5.26. Found: C, 43.79; H, 5.42; N, 5.06. |
| 61 | 2-13 | 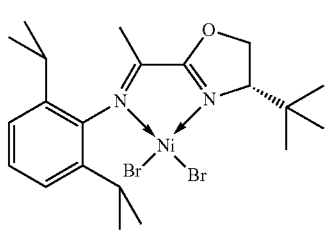 | Anal. Calcd. For $C_{21}H_{32}Br_2N_2NiO$: C, 46.11; H, 5.90; N, 5.12. Found: C, 45.83; H, 5.48; N, 4.96. |

TABLE 2-continued

| Example No. | No. | Structure | elemental analysis |
|---|---|---|---|
| 62 | 2-14 | 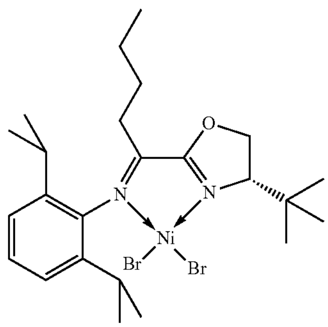 | Anal. Calcd. For C$_{24}$H$_{38}$Br$_2$N$_2$NiO: C, 48.93; H, 6.50; N, 4.76. Found: C, 48.47; H, 6.62; N, 5.00. |
| 63 | 2-15 | 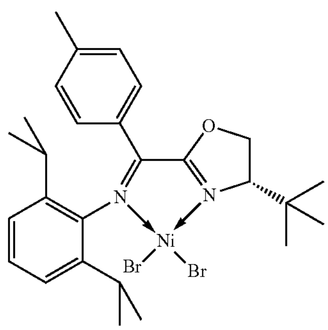 | Anal. Calcd. For C$_{27}$H$_{36}$Br$_2$N$_2$NiO: C, 52.05; H, 5.82; N, 4.50. Found: C, 51.78; H, 5.45; N, 4.76. |
| 64 | 2-16 | 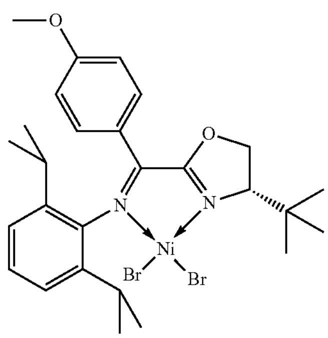 | Anal. Calcd. For C$_{27}$H$_{36}$Br$_2$N$_2$NiO$_2$: C, 50.74; H, 5.68; N, 4.38. Found: C, 51.01; H, 5.59; N, 4.31. |
| 65 | 2-17 | 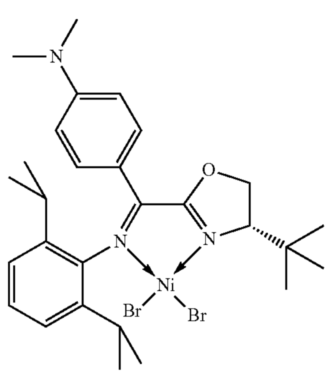 | Anal. Calcd. For C$_{28}$H$_{39}$Br$_2$N$_3$NiO: C, 51.57; H, 6.03; N, 6.44. Found: C, 51.23; H, 5.75; N, 6.36. |

TABLE 2-continued
| Example No. | No. | Structure | elemental analysis |
|---|---|---|---|
| 66 | 2-18 | 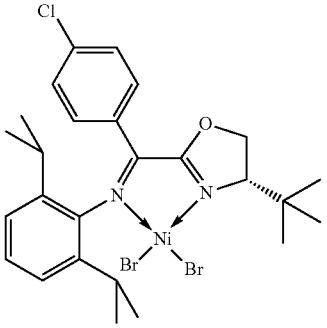 | Anal. Calcd. For $C_{26}H_{33}Br_2ClN_2NiO$: C, 48.53; H, 5.17; N, 4.35. Found: C, 48.20; H, 5.03; N, 4.19. |
| 67 | 2-19 | 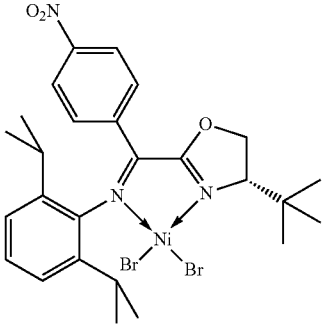 | Anal. Calcd. For $C_{26}H_{33}Br_2N_3NiO_3$: C, 47.74; H, 5.09; N, 6.42. Found: C, 47.39; H, 5.02; N, 6.31. |
| 68 | 2-20 | 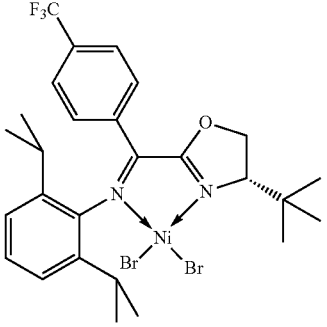 | Anal. Calcd. For $C_{27}H_{33}Br_2F_3N_2NiO$: C, 47.90; H, 4.91; N, 4.14. Found: C, 47.81; H, 4.59; N, 3.94. |
| 69 | 2-21 | 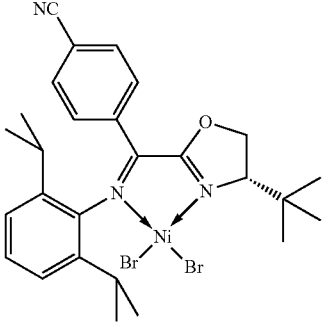 | Anal. Calcd. For $C_{27}H_{33}Br_2N_3NiO$: C, 51.14; H, 5.25; N, 6.63. Found: C, 51.21; H, 5.08; N, 6.43. |

TABLE 2-continued

| Example No. | No. | Structure | elemental analysis |
|---|---|---|---|
| 70 | 2-22 | 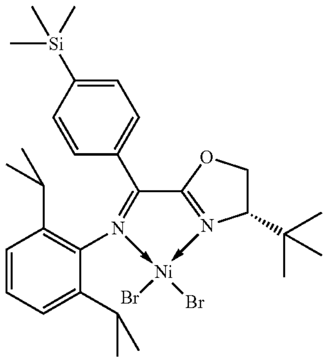 | Anal. Calcd. For C$_{29}$H$_{42}$Br$_2$N$_2$NiOSi: C, 51.13; H, 6.21; N, 4.11. Found: C, 50.86; H, 6.79; N, 3.85. |
| 71 | 2-23 | 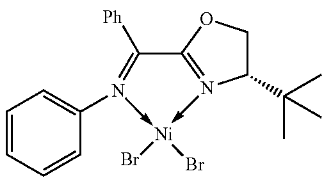 | Anal. Calcd. For C$_{20}$H$_{22}$Br$_2$N$_2$NiO: C, 45.76; H, 4.22; N, 5.34. Found: C, 45.42; H, 4.21; N, 5.29. |
| 72 | 2-24 | 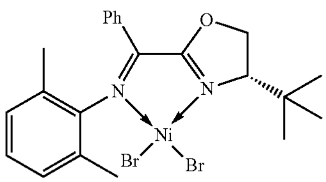 | Anal. Calcd. For C$_{22}$H$_{26}$Br$_2$N$_2$NiO: C, 47.79; H, 4.74; N, 5.07. Found: C, 47.45; H, 4.38; N, 5.01. |
| 73 | 2-25 | 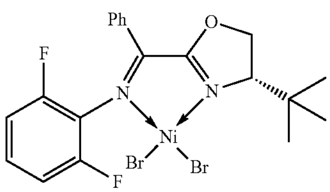 | Anal. Calcd. For C$_{20}$H$_{20}$Br$_2$F$_2$N$_2$NiO: C, 42.83; H, 3.59; N, 4.99. Found: C, 42.45; H, 3.38; N, 4.76. |
| 74 | 2-26 | 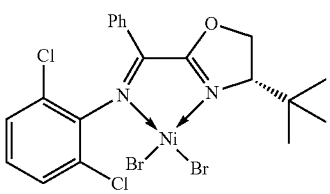 | Anal. Calcd. For C$_{20}$H$_{20}$Br$_2$Cl$_2$N$_2$NiO: C, 40.45; H, 3.39; N, 4.72. Found: C, 40.21; H, 3.28; N, 4.49. |
| 75 | 2-27 | 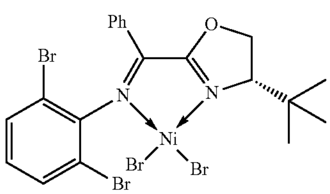 | Anal. Calcd. For C$_{20}$H$_{20}$Br$_4$N$_2$NiO: C, 35.19; H, 2.95; N, 4.10. Found: C, 35.03; H, 3.02; N, 3.95. |
| 76 | 2-28 | 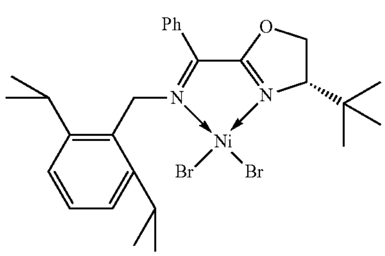 | Anal. Calcd. For C$_{27}$H$_{36}$Br$_2$N$_2$NiO: C, 52.05; H, 5.82; N, 4.50. Found: C, 51.87; H, 5.38; N, 4.28. |

TABLE 2-continued

| Example | No. | Structure | elemental analysis |
|---|---|---|---|
| 77 | 2-29 | 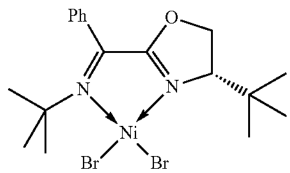 | Anal. Calcd. For $C_{18}H_{26}Br_2N_2NiO$: C, 42.82; H, 5.19; N, 5.55. Found: C, 42.48; H, 5.28; N, 5.37. |
| 78 | 2-30 | 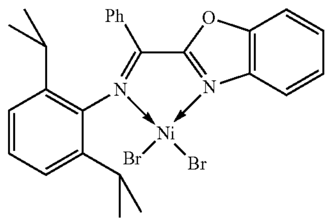 | Anal. Calcd. For $C_{26}H_{26}Br_2N_2NiO$: C, 51.96; H, 4.36; N, 4.66. Found: C, 51.78; H, 4.27; N, 4.41. |
| 79 | 2-31 | 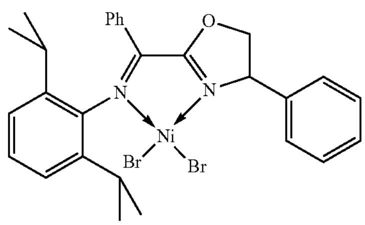 | Anal. Calcd. For $C_{28}H_{28}Br_2N_2NiO$: C, 53.63; H, 4.50; N, 4.47. Found: C, 53.46; H, 4.39; N, 4.38. |
| 80 | 2-32 | 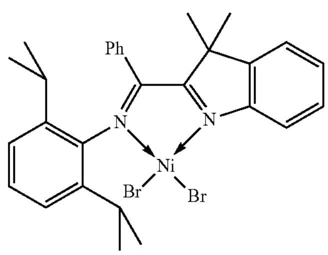 | Anal. Calcd. For $C_{29}H_{32}Br_2N_2Ni$: C, 55.54; H, 5.14; N, 4.47. Found: C, 55.37; H, 5.02; N, 4.32. |
| 81 | 2-33 | 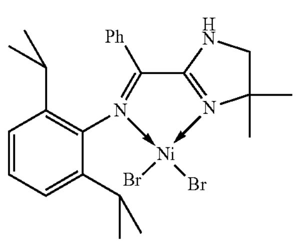 | Anal. Calcd. For $C_{24}H_{31}Br_2N_3Ni$: C, 49.70; H, 5.39; N, 7.24. Found: C, 50.03; H, 5.26; N, 7.29. |
| 82 | 2-34 | 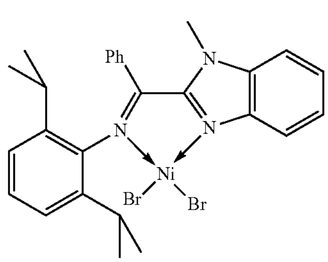 | Anal. Calcd. For $C_{27}H_{29}Br_2N_3Ni$: C, 52.81; H, 4.76; N, 6.84. Found: C, 52.75; H, 4.58; N, 6.72. |

TABLE 2-continued

| Example | No. | Structure | elemental analysis |
|---|---|---|---|
| 83 | 2-35 | 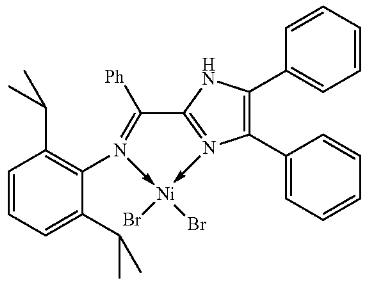 | Anal. Calcd. For $C_{34}H_{33}Br_2N_3Ni$: C, 58.16; H, 4.74; N, 5.98. Found: C, 58.04; H, 4.36; N, 5.37. |
| 84 | 2-36 | 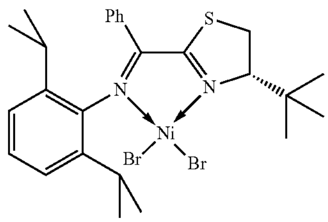 | Anal. Calcd. For $C_{26}H_{34}Br_2N_2NiS$: C, 49.95; H, 5.48; N, 4.48. Found: C, 49.65; H, 5.27; N, 4.32. |
| 85 | 2-37 | 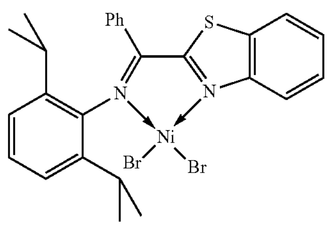 | Anal. Calcd. For $C_{26}H_{26}Br_2N_2NiS$: C, 50.61; H, 4.25; N, 4.54. Found: C, 50.32; H, 4.22; N, 4.39. |
| 86 | 2-38 | 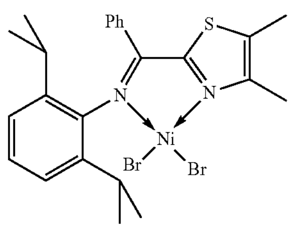 | Anal. Calcd. For $C_{24}H_{28}Br_2N_2NiS$: C, 48.44; H, 4.74; N, 4.71. Found: C, 48.03; H, 4.21; N, 4.39. |
| 87 | 2-39 | 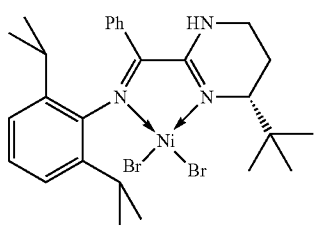 | Anal. Calcd. For $C_{27}H_{37}Br_2N_3Ni$: C, 52.13; H, 5.99; N, 6.75. Found: C, 52.01; H, 5.60; N, 6.62. |
| 88 | 2-40 | 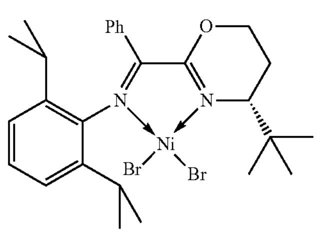 | Anal. Calcd. For $C_{27}H_{36}Br_2N_2NiO$: C, 52.05; H, 5.82; N, 4.50. Found: C, 51.76; H, 5.64; N, 4.32. |

TABLE 2-continued

| Example | No. | Structure | elemental analysis |
| --- | --- | --- | --- |
| 89 | 2-41 | 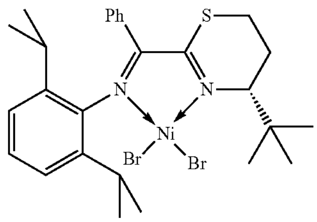 | Anal. Calcd. For $C_{27}H_{36}Br_2N_2NiS$: C, 50.74; H, 5.68; N, 4.38. Found: C, 50.38; H, 5.22; N, 4.15. |
| 90 | 2-42 | 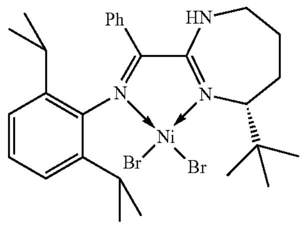 | Anal. Calcd. For $C_{28}H_{39}Br_2N_3Ni$: C, 52.87; H, 6.18; N, 6.61. Found: C, 52.52; H, 6.60; N, 6.45. |
| 91 | 2-43 | 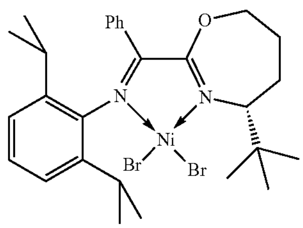 | Anal. Calcd. For $C_{28}H_{38}Br_2N_2NiO$: C, 52.78; H, 6.01; N, 4.40. Found: C, 52.41; H, 5.83; N, 4.29. |
| 92 | 2-44 | 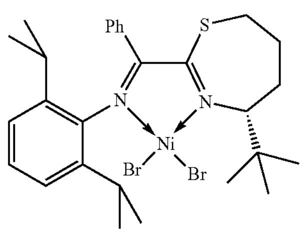 | Anal. Calcd. For $C_{28}H_{38}Br_2N_2NiS$: C, 51.49; H, 5.86; N, 4.29. Found: C, 51.35; H, 5.32; N, 4.15. |
| 93 | 2-45 | 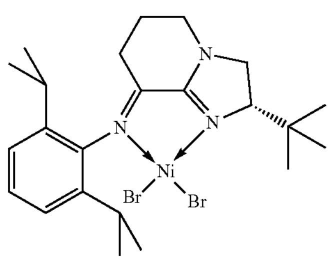 | Anal. Calcd. For $C_{23}H_{35}Br_2N_3Ni$: C, 48.29; H, 6.17; N, 7.35. Found: C, 48.01; H, 5.95; N, 7.24. |
| 94 | 2-46 | 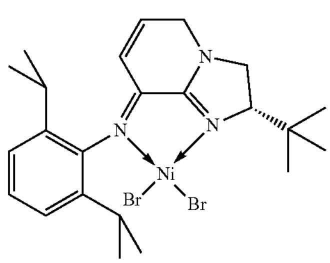 | Anal. Calcd. For $C_{23}H_{33}Br_2N_3Ni$: C, 48.46; H, 5.84; N, 7.37. Found: C, 48.15; H, 5.47; N, 7.08. |

TABLE 2-continued

| Example | No. | Structure | elemental analysis |
|---|---|---|---|
| 95 | 2-47 | 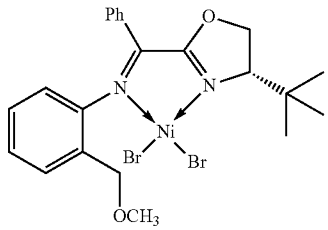 | Anal. Calcd. For $C_{22}H_{26}Br_2N_2NiO_2$: C, 46.44; H, 4.61; N, 4.92. Found: C, 46.06; H, 4.60; N, 4.59. |
| 96 | 2-48 | 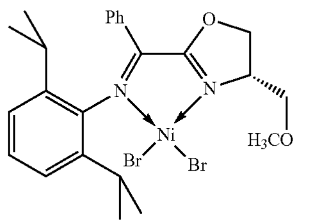 | Anal. Calcd. For $C_{24}H_{30}Br_2N_2NiO_2$: C, 48.28; H, 5.06; N, 4.69. Found: C, 48.03; H, 4.97; N, 4.64. |
| 97 | 2-49 | 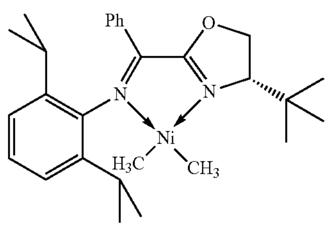 | Anal. Calcd. For $C_{28}H_{40}N_2NiO$: C, 70.16; H, 8.41; N, 5.84. Found: C, 70.01; H, 8.35; N, 5.62. |
| 98 | 2-50 | 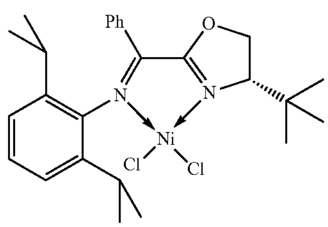 | Anal. Calcd. For $C_{26}H_{34}Cl_2N_2NiO$: C, 60.03; H, 6.59; N, 5.39. Found: C, 59.85; H, 6.60; N, 5.58. |
| 99 | 2-51 | 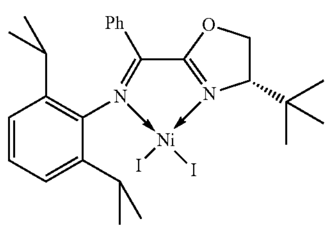 | Anal. Calcd. For $C_{26}H_{34}I_2N_2NiO$: C, 44.42; H, 4.87; N, 3.98. Found: C, 44.08; H, 4.60; N, 3.67. |
| 100 | 2-52 | 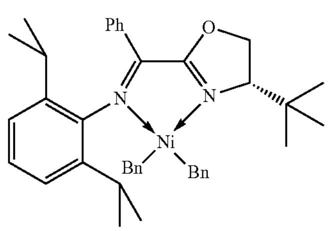 | Anal. Calcd. For $C_{40}H_{48}N_2NiO$: C, 76.08; H, 7.66; N, 4.44. Found: C, 75.84; H, 7.59; N, 4.32. |
| 101 | 2-53 | 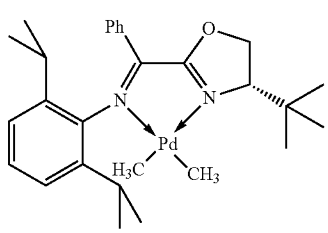 | Anal. Calcd. For $C_{28}H_{40}N_2OPd$: C, 63.81; H, 7.65; N, 5.32. Found: C, 63.55; H, 7.43; N, 5.20. |

TABLE 2-continued

| Example No. | Structure | elemental analysis |
|---|---|---|
| 102 2-54 | | Anal. Calcd. For $C_{26}H_{34}Cl_2N_2OPd$: C, 54.99; H, 6.03; N, 4.93. Found: C, 54.64; H, 5.90; N, 4.69. |
| 103 2-55 | | Anal. Calcd. For $C_{26}H_{34}Br_2N_2OPd$: C, 47.55; H, 5.22; N, 4.27. Found: C, 47.09; H, 5.03; N, 4.14. |

Preparation of Highly Branched Oily Polyolefins

Example 104

250 mL of the polymerization flask was replaced by nitrogen for three times, and then replaced by ethylene. 40 mL of toluene was added under ethylene atmosphere, and 1.10 mL (0.9 mol/L) diethylaluminum chloride in toluene was added. Under 30° C., and 1 atm of ethylene, complex 2-9 (2.0 umol) was added to promote the polymerization for 30 min, then the ethylene was cut off and 1.0 mL of methanol was added to quench the reaction. The solvent was removed to obtain oily polyethylene, the activity was 6.6× $10^6$ g/mol·h·atm, and the methyl number per 1000 methylene of the oily polyethylene was 120.

Example 105

The complex was prepared in situ, 60 μmol of ligand L1-9 and (DME)NiBr$_2$ weighed in glovebox, were dissolved in 30 mL dichloromethane, and reacted at under room temperature for 2 h, and then the solution was diluted into 2 μmol/mL solution for further use.

250 mL of the polymerization flask was replaced by nitrogen for three times, and then replaced by ethylene. 40 mL of toluene was added under ethylene atmosphere, and 1.10 mL (0.9 mol/L) diethylaluminum chloride in toluene was added. At 30° C. and, 1 atm of ethylene, the above in-situ prepared complex (2.0 umol) was added to promote the polymerizatione for 30 min, then the ethylene was cut off and 1.0 mL of methanol was added to quench the reaction. The solvent of reaction solution was removed to obtain oily polyethylene, the activity was 6.7×$10^6$ g/mol·h·atm, and the methyl number per 1000 methylene of the oily polyethylene was 126.

Example 106

The example 104 was repeated except that the propylene was used instead of ethylene.
Results: oily polymer 8.7 g was obtained. The activity was 8.7×$10^6$ g/mol·h·atm, and the methyl number per 1000 methylene of the oily polyethylene was 276.

Example 107

The example 104 was repeated except that the mixture of cis/trans-2-butene was used to instead of ethylene.
Results: oily polymer 10.8 g was obtained. The activity was 10.8×$10^6$ g/mol·h·atm, and the methyl number per 1000 methylene of the oily polyethylene was 279.

Example 108

The example 104 was repeated except that the 1-hexene was used instead of ethylene.
Results: oily polymer 8.3 g was obtained. The activity was 8.3×$10^6$ g/mol·h·atm, and the methyl number per 1000 methylene of the oily polyethylene was 235.

Example 109

The example 104 was repeated except that the 1-decene was used to instead of ethylene.
Results: oily polymer 9.1 g was obtained. The activity was 9.1×$10^6$ g/mol·h·atm, and the methyl number per 1000 methylene of the oily polyethylene was 208.

Example 110

The example 104 was repeated except that the cyclohexene was used to instead of ethylene.
Results: oily polymer 3.5 g was obtained. The activity was 3.5×$10^6$ g/mol·h·atm.

Example 111

The example 104 was repeated except that the n-hexane was used instead of toluene.
Results: oily polyethylene 5.3 g was obtained. The activity was 5.3×$10^6$ g/mol·h·atm, and the methyl number per 1000 methylene of the oily polyethylene was 134.

Example 112

The example 104 was repeated except that the DCE was used instead of toluene.
Results: oily polyethylene 5.8 g was obtained. The activity was 5.8×$10^6$ g/mol·h·atm, and the methyl number per 1000 methylene of the oily polyethylene was 140.

Example 113

The example 104 was repeated except that the MMAO was used instead of diethylaluminum chloride.

Results: oily polyethylene 6.0 g was obtained. The activity was 6.0×10$^6$ g/mol·h·atm, and the methyl number per 1000 methylene of the oily polyethylene was 132.

Example 114

The example 104 was repeated except that the MAO was used instead of diethylaluminum chloride.

Results: oily polyethylene 5.5 g was obtained. The activity was 5.5×10$^6$ g/mol·h·atm, and the methyl number per 1000 methylene of the oily polyethylene was 138.

Example 115

The example 104 was repeated except that polymerization temperature 40° C.

Results: oily polyethylene 5.2 g was obtained. The activity was 5.2×10$^6$ g/mol·h·atm, and the methyl number per 1000 methylene of the oily polyethylene was 156.

Example 116

The example 104 was repeated except that polymerization temperature 50° C.

Results: oily polyethylene 4.6 g was obtained. The activity was 4.6×10$^6$ g/mol·h·atm, and the methyl number per 1000 methylene of the oily polyethylene was 175.

Example 117

The example 104 was repeated except that polymerization temperature 70° C.

Results: oily polyethylene 2.3 g was obtained. The activity was 2.3×10$^6$ g/mol·h·atm, and the methyl number per 1000 methylene of the oily polyethylene was 214.

Example 118

300 mL autoclave was dried under vacuum at 120° C. overnight in advance, and the autoclave was rechanged with nitrogen under 30° C. for 3 times, 100 mL of toluene was added, and cocatalyst diethylaluminium chloride 1.10 mL (0.9 mol/L) was added, and stirred for 10 min., after complex 2-9 (5 umol) was added, the ethylene pressure was improved up to 3 atm and the polymerization was proceeded for 1 h, and then the ethylene was cut off. Oily polyethylene was obtained after removing the solvent. The activity was 7.0×10$^6$ g/mol·h·atm, and the methyl number per 1000 methylene of the oily polyethylene was 94.

Example 119

The example 118 was repeated while the pressure of ethylene was changed to 5 atm.

Results: The activity was 4.3×10$^6$ g/mol·h·atm, and the methyl number per 1000 methylene of the oily polyethylene was 85.

In examples 120-149, different complexes were used to replace the corresponding complex 2-9 in example 104 so as to obtain different oily polymers in examples 120-149, and the polymerization results are shown in table 3.

TABLE 3

| Example | Complex | Polymerization activity (10$^6$ g/mol · h · atm) | The methyl number per 1000 methylene |
|---|---|---|---|
| 120 | 2-2 | 4.2 | 167 |
| 121 | 2-3 | 4.8 | 156 |
| 122 | 2-5 | 3.2 | 145 |
| 123 | 2-6 | 3.8 | 133 |
| 124 | 2-8 | 6.5 | 127 |
| 125 | 2-10 | 7.3 | 102 |
| 126 | 2-12 | 8.1 | 94 |
| 127 | 2-13 | 7.8 | 123 |
| 128 | 2-14 | 7.4 | 164 |
| 129 | 2-16 | 3.6 | 109 |
| 130 | 2-18 | 6.8 | 123 |
| 131 | 2-20 | 8.6 | 142 |
| 132 | 2-22 | 4.2 | 133 |
| 133 | 2-24 | 3.5 | 203 |
| 134 | 2-27 | 6.2 | 154 |
| 135 | 2-29 | 2.1 | 219 |
| 136 | 2-31 | 5.5 | 156 |
| 137 | 2-32 | 1.9 | 134 |
| 138 | 2-35 | 4.3 | 147 |
| 139 | 2-36 | 3.7 | 126 |
| 140 | 2-40 | 5.7 | 118 |
| 141 | 2-43 | 6.0 | 173 |
| 142 | 2-45 | 6.9 | 148 |
| 143 | 2-47 | 3.2 | 109 |
| 144 | 2-48 | 6.8 | 174 |
| 145 | 2-49 | 9.0 | 122 |
| 146 | 2-50 | 4.1 | 165 |
| 147 | 2-52 | 2.5 | 120 |
| 148 | 2-53 | 0.5 | 212 |
| 149 | 2-55 | 1.2 | 229 |

The Copolymerization of Ethylene and Polar Monomer (Note: All the numbers of the following polar monomer refer to the numbering of polar monomers in the "embodiments for carrying out the invention" section)

Example 150

250 mL of the polymerization flask was replaced by nitrogen for three times, and then replaced by ethylene. 40 mL of solvent toluene was added under ethylene atmosphere, and 4.40 mL (0.9 mol/L) of diethylaluminum chloride in toluene was added. At 30° C., and 1 atm ethylene, 2 mmol of polar monomer M3 was added, and complex 2-9 (2.0 umol) was added after 5 minutes, polymerized for 30 min, then the ethylene stream was cut off and 1.0 mL of methanol was added to quench the reaction. The solvent was removed to obtain oily polyethylene, the activity was 3.8× 10$^5$ g/mol·h·atm, and the polar group number per 1000 methylene of the oily polymer was 59.

Example 151

Al$^i$Bu$_3$ (60 mmol) and 20 mL toluene were added into reaction flask which was dried in vacuo at high temperature and replaced with nitrogen, and the polar monomer M3 (50 mmol) in toluene was added dropwise into the above solution at −78° C. After 2 h, the reaction was warmed to room temperature and stirred for 12 h, and certain amount of toluene was added so as to prepare polar monomer solution in toluene (1.0 mol/L) for further use.

250 mL of the polymerization flask was replaced by nitrogen for three times, and then replaced by ethylene. 40 mL of toluene was added under ethylene atmosphere, and 1.10 mL (0.9 mol/L) of diethylaluminum chloride in toluene was added. At 30° C., 1 atm ethylene, 5 mmol of polar monomer M3 was added, and complex 2-9 (2.0 umol) was added after 5 minutes, the polymerization proceed for 30 min, then the ethylene stream was cut off and 1.0 mL of methanol was added to quench the reaction. The solvent was removed to obtain oily polyethylene, the activity was 4.6× $10^5$ g/mol·h·atm, and the polar group number per 1000 methylene of the oily polymer was 64.

In examples 152-166, different polar monomers were used instead of the corresponding polar monomer M3 in example 150 so as to obtain different oily polymers in examples 152-166, and the polymerization results are shown in table 4.

TABLE 4

| Example | Complex | AlEt$_2$Cl/ Ni | polar monomer | the amount of the monomer (mmol) | polymerization activity ($10^5$ g/mol · h · atm) | Polar monomer insertion rate (the number of polar group per 1000 methylene) |
|---|---|---|---|---|---|---|
| 152 | 2-9 | 500 | M3 | 2 | 1.7 | 13 |
| 153 | 2-9 | 1000 | M3 | 5 | 4.4 | 26 |
| 154 | 2-9 | 3000 | M3 | 10 | 7.1 | 31 |
| 155 | 2-9 | 3000 | M2 | 5 | 4.0 | 63 |
| 156 | 2-9 | 3000 | M4 | 5 | 7.4 | 29 |
| 157 | 2-9 | 3000 | M5 | 5 | 1.0 | 23 |
| 158 | 2-9 | 3000 | M7 | 5 | 3.1 | 17 |
| 159 | 2-9 | 3000 | M9 | 5 | 4.6 | 46 |
| 160 | 2-9 | 3000 | M11 | 5 | 5.8 | 38 |
| 161 | 2-47 | 3000 | M7 | 5 | 8.3 | 29 |
| 162 | 2-47 | 3000 | M8 | 5 | 5.7 | 77 |
| 163 | 2-47 | 3000 | M11 | 5 | 4.0 | 35 |
| 164 | 2-47 | 3000 | M13 | 5 | 3.7 | 65 |
| 165 | 2-48 | 3000 | M3 | 5 | 2.0 | 24 |
| 166 | 2-48 | 3000 | M11 | 5 | 6.4 | 43 |

In examples 167-177, different polar monomers were used instead of the corresponding polar monomer M3 in example 151 so as to obtain different oily polymers in examples 167-177, and the polymerization results are shown in table 5.

TABLE 5

| Example | Complex | AlEt$_2$Cl/ Ni | polar monomer | the amount of the monomer (mmol) | polymerization activity ($10^5$ g/mol · h · atm) | Polar monomer insertion rate (the number of polar group per 1000 methylene) |
|---|---|---|---|---|---|---|
| 167 | 2-9 | 500 | M3 | 2 | 5.3 | 52 |
| 168 | 2-9 | 1000 | M3 | 5 | 6.9 | 49 |
| 169 | 2-9 | 3000 | M3 | 10 | 9.1 | 98 |
| 170 | 2-9 | 3000 | M2 | 5 | 6.0 | 123 |
| 171 | 2-9 | 3000 | M4 | 5 | 8.2 | 75 |
| 172 | 2-9 | 3000 | M7 | 5 | 5.8 | 35 |
| 173 | 2-9 | 3000 | M11 | 5 | 8.5 | 117 |
| 174 | 2-47 | 3000 | M7 | 5 | 9.8 | 57 |
| 175 | 2-47 | 3000 | M11 | 5 | 5.1 | 35 |
| 176 | 2-47 | 3000 | M13 | 5 | 4.5 | 105 |
| 177 | 2-48 | 3000 | M3 | 5 | 2.8 | 34 |

Example 178

2.5 g of highly branched oily polyethylene obtained in example 104, Pd/C (50 mg), n-hexane (10 mL) were added into 50 mL egg-shaped flask. After exchanged nitrogen for three times, the reaction was carried out at room temperature, under 1 atm hydrogen atmosphere overnight. The reaction was monitored by $^1$H NMR until the reactant has been hydrogenated completely. Then the hydrogenation was stopped, the reaction mixture was filtered and the solvent was removed to obtain oily highly branched alkanes, of which bromine value was 0.31 g/100 g, methyl number per 1000 methylene was 140, and viscosity index VI was 241, the kinematic viscosity at 100° C. was 7.9 cSt.

Example 179

2.5 g of highly branched oily polyethylene obtained in example 104 and Pd/C (50 mg) were added into 50 mL egg-shaped flask. After exchanged nitrogen for three times, the reaction was carried out at room temperature, under 1 atm hydrogen atmosphere overnight. The reaction was monitored by $^1$H NMR until the reactant has been hydrogenated completely. Then the hydrogenation was stopped, the reaction mixture was filtered and the solvent was removed to obtain oily highly branched alkane, of which bromine value was 0.33 g/100 g, methyl number per 1000 methylene was 146.

Example 180

The example 178 was repeated except that the Pd/C was replaced by Pd(OH)$_2$.
Result: bromine value was 0.30 g/100 g.

Example 181

The example 178 was repeated except that the hydrogenation substrate was replaced by the oily polyethylene obtained in example 115.
Result: the bromine value of the oily highly branched alkane was 0.35 g/100 g, methyl number per 1000 methylene was 170, and viscosity index VI was 290.

Example 182

The example 178 was repeated except that the hydrogenation substrate was replaced by the oily polyethylene obtained in example 118.
Result: the bromine value of the oily highly branched alkane was 0.32 g/100 g.

Example 183

The example 104 was repeated, and hydrogen was pumped in simultaneously when the olefin polymerization catalyst contacted the ethylene. After the hydrogenation was completed, it was filtered and the solvent of filtrate was removed so as to obtain oily highly branched alkane, of which bromine value was 0.46 g/100 g, methyl number per 1000 methylene was 230, and viscosity index was 196.

Example 184

The example 104 was repeated, the olefin polymerization catalyst contacted to the ethylene for 30 min, Pd/C 50 mg was added without treatment, and then hydrogen was pumped. After the hydrogenation was completed, it was filtered and the solvent of filtrate was removed so as to obtain oily highly branched alkane, of which methyl number per 1000 methylene was 207.

Example 185

The example 104 was repeated, treatment was omitted after the olefin polymerization catalyst contacted to the ethylene for 30 min, and the atmosphere was replaced by hydrogen. The reaction was conducted under hydrogen atmosphere until the hydrogenation was completed. It was filtered and the solvent of filtrate was removed so as to obtain oily highly branched alkane, the bromine value of which was 0.33 g/100 g.

Example 186

300 mL autoclave was dried under vacuum in 120° C. oil bath overnight, and replaced by nitrogen for three times. On 50° C. oil bath, 50 mL of toluene and 1.10 mL (0.9 mol/L) of diethylaluminum chloride in toluene was added, and 5 umol of complex 2-9 was added under 0.5 atm hydrogen atmosphere, and ethylene was pumped in to carry out the polymerization reaction for 30 min, then the reaction was stopped. The reaction solution was filtered and the solvent of filtrate was removed so as to obtain 4.0 g of oily highly branched alkane, of which the bromine value was 0.45 g/100 g, and the methyl number per 1000 methylene was 235.

Example 187

The example 118 was repeated while the pressure of ethylene was changed to 10 atm.
Results: The activity was 9.3×10$^6$ g/mol·h·atm, and the methyl number per 1000 methylene of the oily polyethylene was 85.

Example 188

The example 118 was repeated while the pressure of ethylene was changed to 20 atm.
Results: The activity was 2.1×10$^7$ g/mol·h·atm, and the methyl number per 1000 methylene of the oily polyethylene was 79.

Example 189

The example 118 was repeated except that polymerization temperature was 50° C.
Results: The activity was 6.9×10$^6$ g/mol·h·atm, and the methyl number per 1000 methylene of the oily polyethylene was 103.

Example 190

The example 118 was repeated except that polymerization temperature was 70° C.
Results: The activity was 4.4×10$^6$ g/mol·h·atm, and the methyl number per 1000 methylene of the oily polyethylene was 128.

Example 191

The example 118 was repeated except that toluene was replaced by n-hexane.
Results: The activity was 5.7×10$^6$ g/mol·h·atm, and the methyl number per 1000 methylene of the oily polyethylene was 89.

Example 192

The example 118 was repeated except that toluene was replaced by dichloromethane (DCM) and the polymerization time was 4 hours.
Results: The activity was 6.6×10$^6$ g/mol·h·atm, and the methyl number per 1000 methylene of the oily polyethylene was 157.

Example 193

The example 118 was repeated except that toluene was replaced by 1, 2-dichloroethane (DCE).
Results: The activity was 4.7×10$^6$ g/mol·h·atm, and the methyl number per 1000 methylene of the oily polyethylene was 165.

Example 194

The example 118 was repeated except that toluene was replaced by dichloromethane (DCM) and the ethylene pressure was changed to 10 atm.

Results: The activity was 7.8×10⁶ g/mol·h·atm, and the methyl number per 1000 methylene of the oily polyethylene was 175.

Example 195

The example 118 was repeated except that toluene was replaced by dichloromethane (DCM) and the ethylene pressure was changed to 20 atm.
Results: The activity was 5.5×10⁷ g/mol·h·atm, and the methyl number per 1000 methylene of the oily polyethylene was 184.

Example 196

The example 118 was repeated except that toluene was replaced by 1, 2-dichloroethane (DCE) and the ethylene pressure was changed to 20 atm.
Results: The activity was 6.1×10⁷ g/mol·h·atm, and the methyl number per 1000 methylene of the oily polyethylene was 178.

Example 197

The example 118 was repeated except that toluene was replaced by dichloromethane (DCM) and the ethylene pressure was changed to 5 atm, and the complex 2-9 was replaced by complex 2-2.
Results: The activity was 9.0×10⁶ g/mol·h·atm, and the methyl number per 1000 methylene carbon of the oily polyethylene was 267.

Example 198

Figure 3:
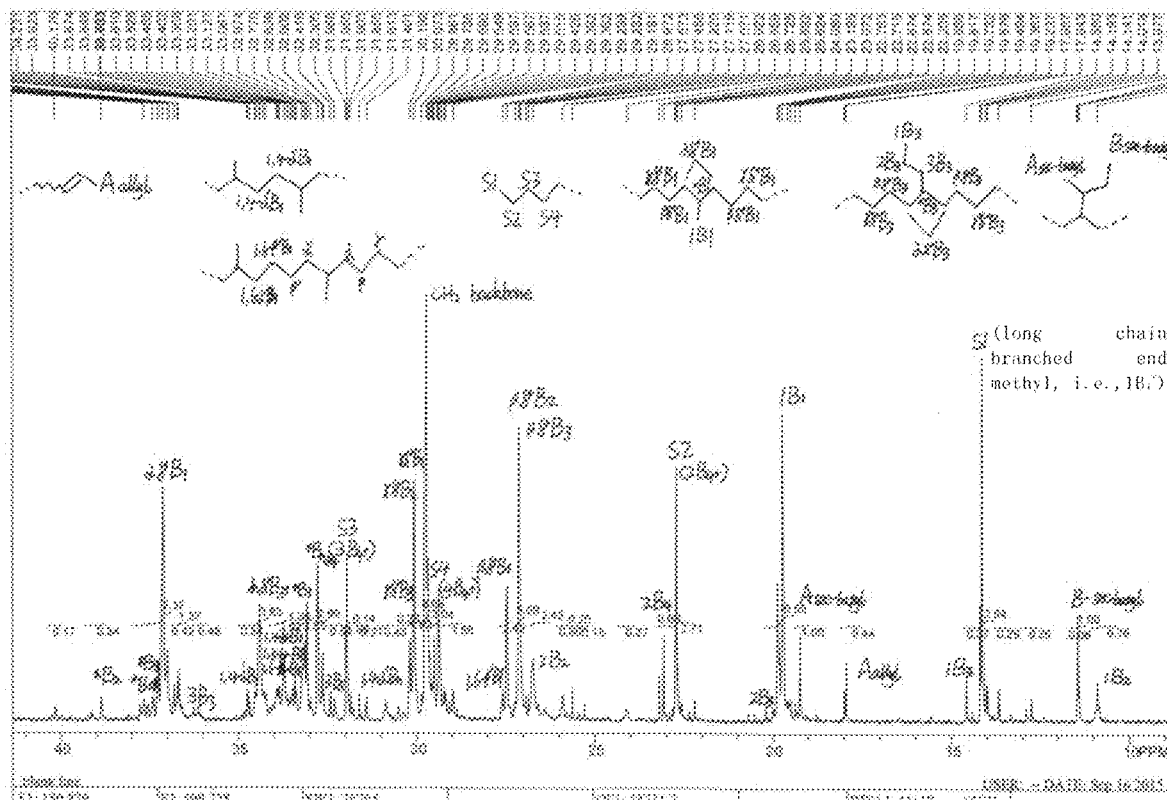
FIG. 3 shows the $^{13}C$ NMR spectrum of the polymer prepared in Example 198 of the present invention.

The example 118 was repeated except that toluene was replaced by dichloromethane (DCM) and the ethylene pressure was changed to 10 atm, and the complex 2-9 was replaced by complex 2-2.
Results: The activity was 2.3×10⁷ g/mol·h·atm, and the methyl number per 1000 methylene of the oily polyethylene was 283, the bromine value was 23.41 g/100 g, and the oxidation stability was 56 minutes. The $^{13}$C spectrum was shown in FIG. 3. The $^{13}$C spectrum has shown that the branch type of the polymer comprises methyl, ethyl, n-propyl, n-butyl, sec-butyl and other branches with more than four carbons, wherein sec-butyl number comprised in 1000 carbons was 24.

Example 199

The example 118 was repeated except that toluene was replaced by 1, 2-dichloroethane (DCE) and the ethylene pressure was changed to 5 atm, and the complex 2-9 was replaced by complex 2-2.
Results: The activity was 1.9×10⁷ g/mol·h·atm, and the methyl number per 1000 methylene of the oily polyethylene was 271.

Example 200

The example 118 was repeated except that toluene was replaced by 1, 2-dichloroethane (DCE) and the ethylene pressure was changed to 10 atm, and the complex 2-9 was replaced by complex 2-2.
Results: The activity was 4.8×10⁶ g/mol·h·atm, and the methyl number per 1000 methylene of the oily polyethylene was 246.

Example 201

Figure 4:
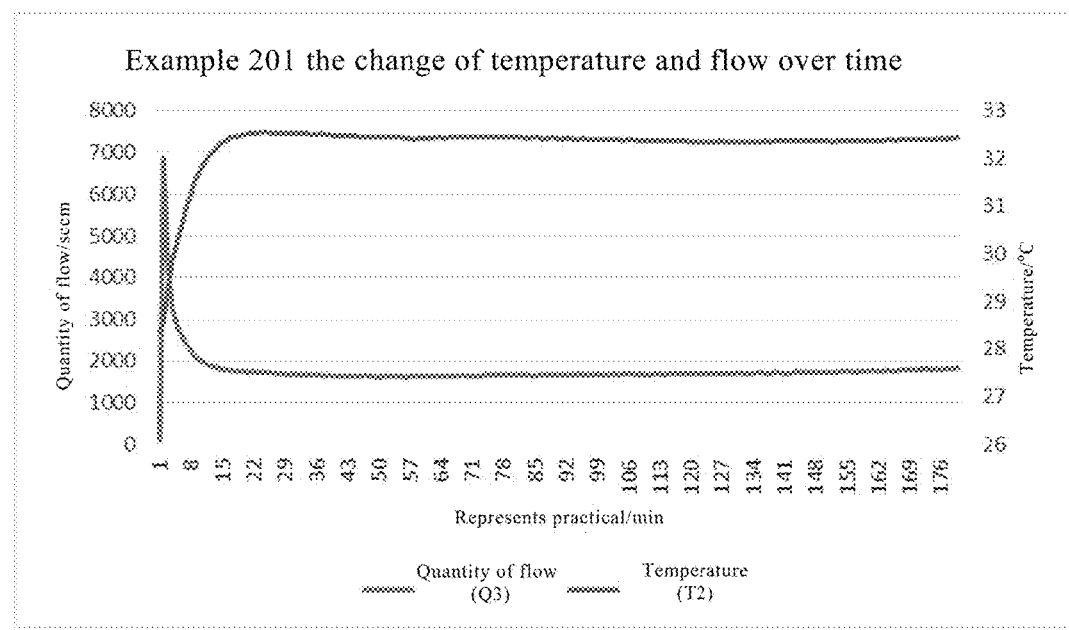
FIG. 4 shows the change of inner temperature of the polymerization system and ethylene flow versus time during the reaction of Example 201 of the present invention.
Figure 5:
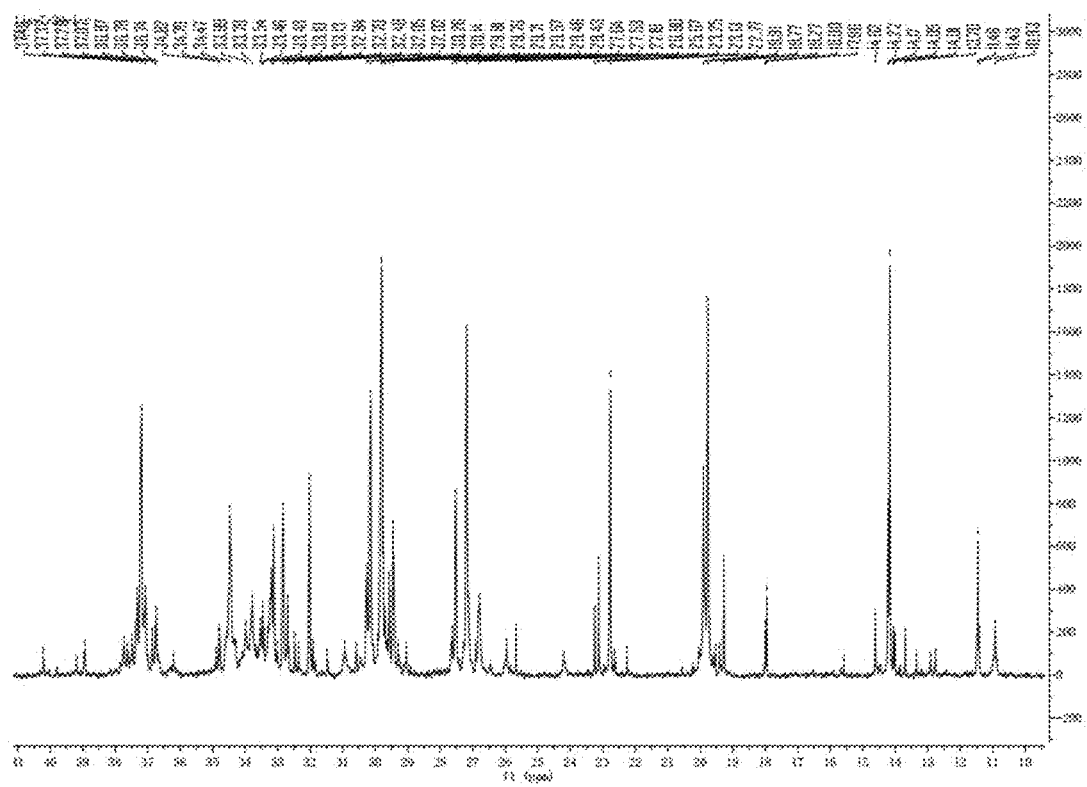
FIG. 5 shows the $^{13}C$ NMR spectrum of the polymer prepared in Example 201 of the present invention.

1 L autoclave was dried under vacuum at 120° C. for 3 hours in advance. After cooled to 30° C., dichloromethane (DCM) 400 mL was added, and cocatalyst diethylaluminium chloride 2.50 mL (2.0 mol/L) was added, stirred for 10 min, and complex 2-2 (10 umol) was added, tracked under 5 atm ethylene pressure for 2 hours, and then the ethylene stream was cut off. Oily polyethylene was obtained after removing the solvent from the reaction solution. The activity was 3.9×10⁷ g/mol·h·atm, and the methyl number per 1000 methylene of the oily polyethylene was 282. The polymer was measured by GPC: Mn=349, Mw=673, PDI=1.69.
The change of inner temperature of the kettle and ethylene flow over time during the reaction was shown in FIG. 4.
The $^{13}$C spectrum was shown in FIG. 5, it can be seen from the $^{13}$C spectrum that there are abundant types of branches in the polymer.

Example 202

The example 201 was repeated while the pressure of ethylene was changed to 10 atm.
Results: The activity was 5.3×10⁷ g/mol·h·atm, and the methyl number per 1000 methylene of the oily polyethylene was 264.

Example 203

The example 201 was repeated except that the reaction temperature was reduced to 20° C.
Results: The activity was 8.0×10⁷ g/mol·h·atm, and the methyl number per 1000 methylene of the oily polyethylene was 257.

Example 204

The example 201 was repeated except that the reaction temperature was raised to 50° C.
Results: The activity was 5.0×10⁷ g/mol·h·atm, and the methyl number per 1000 methylene of the oily polyethylene was 278.

Example 205

The example 201 was repeated except that the solution was replaced by 1, 2-dichloroethane (DCE) and the ethylene pressure was changed to 10 atm.
Results: The activity was 6.3×10⁷ g/mol·h·atm, and the methyl number per 1000 methylene of the oily polyethylene was 264.

Example 206

The example 201 was repeated except that the solution was replaced by toluene.
Results: The activity was 8.7×10⁷ g/mol·h·atm, and the methyl number per 1000 methylene of the oily polyethylene was 231.

Example 207

The example 201 was repeated except that the complex 2-2 was replaced by complex 2-4.
Results: The activity was 8.4×10⁷ g/mol·h·atm, and the methyl number per 1000 methylene of the oily polyethylene was 278.

Example 208

The example 201 was repeated except that the complex 2-2 was replaced by complex 2-5.

Results: The activity was $9.1 \times 10^7$ g/mol·h·atm, and the methyl number per 1000 methylene of the oily polyethylene was 261.

Figure 6:
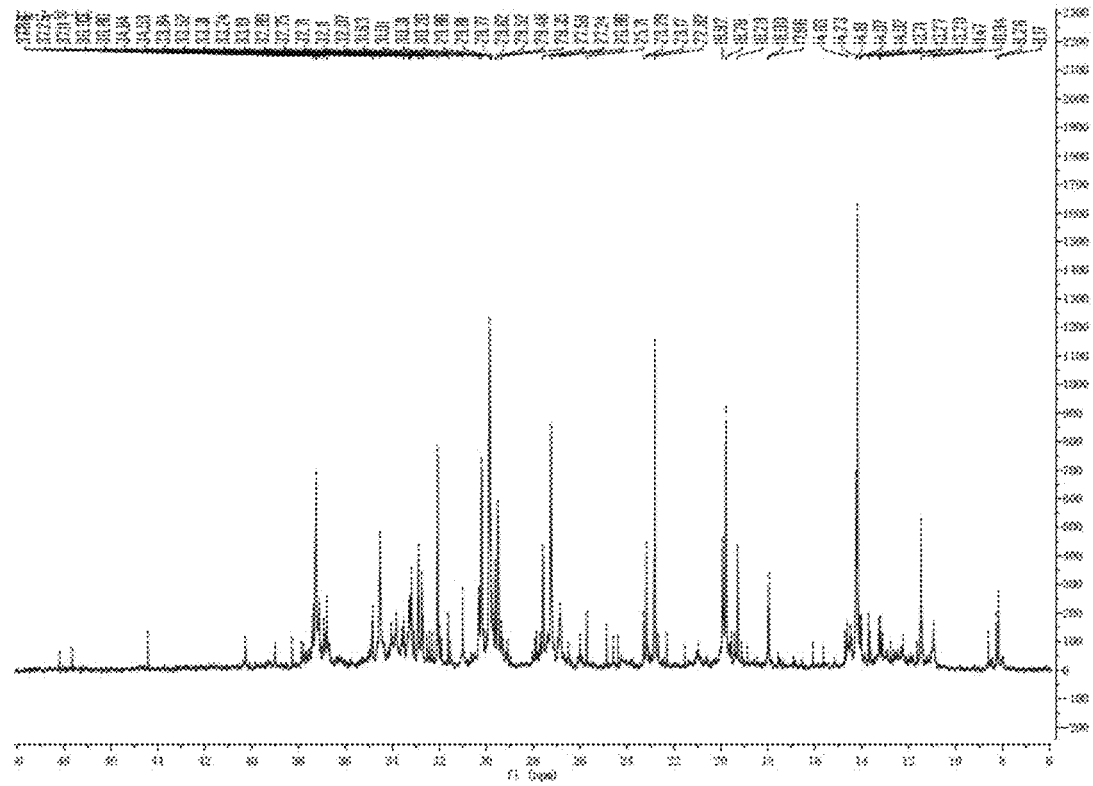
FIG. 6 shows the $^{13}C$ NMR spectrum of the polymer prepared in Example 208 of the present invention.

The $^{13}$C spectrum of the polymer is shown in FIG. 6.

Example 209

The example 208 was repeated while the pressure of ethylene was changed to 10 atm.

Results: The activity was $1.6 \times 10^8$ g/mol·h·atm, and the methyl number per 1000 methylene of the oily polyethylene was 273.

Example 210 (Comparison of Example 201)

The example 201 was repeated except that the complex 2-2 was replaced by complex 2-56.

Complex 2-56

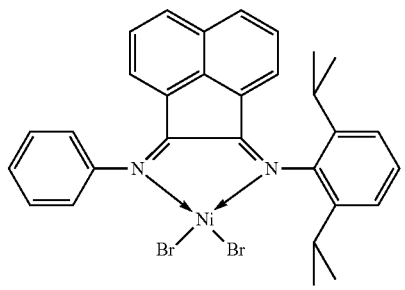

Results: The obtained polymer was a mixture of solid and liquid product, wherein the solid product was 123.70 g and the liquid product was 37.63 g.

Example 211

20 L autoclave was dried under vacuum at 120° C. for 5 hours in advance. After cooled to 30° C., dichloromethane (DCM) 400 mL was added, and cocatalyst diethylaluminium chloride 25.0 mL (2.0 mol/L) was added, stirred for 30 min, and complex 2-2 (100 umol) was added, reacted under 5 atm ethylene pressure for 3 hours, and then the ethylene stream was cut off.

Oily polyethylene was obtained after removing the solvent from the reaction solution. The activity was $3.5 \times 10^7$ g/mol·h·atm, and the methyl number per 1000 methylene of the oily polyethylene was 277.

Example 212

The example 211 was repeated while the pressure of ethylene was changed to 10 atm.

Results: The activity was $7.6 \times 10^7$ g/mol·h·atm, and the methyl number per 1000 methylene of the oily polyethylene was 239.

Example 213

The example 211 was repeated except that the reaction temperature was raised to 50° C.

Results: The activity was $4.8 \times 10^7$ g/mol·h·atm, and the methyl number per 1000 methylene of the oily polyethylene was 286.

Example 214

The example 211 was repeated except that the solution was replaced by 1, 2-dichloroethane (DCE) and the ethylene pressure was changed to 10 atm.

Results: The activity was $9.2 \times 10^7$ g/mol·h·atm, and the methyl number per 1000 methylene of the oily polyethylene was 272.

In examples 215-225, different racemic or optical raw materials were used instead of the corresponding raw material in example 1 so as to prepare ligands L1-49 to L1-59, and the results are shown in Table 6.

TABLE 6

| Example | No. | The structure of the ligand: | structural characterization (elemental analysis) |
|---|---|---|---|
| 215 | L1-49 | | Anal. Calcd. For $C_{30}H_{26}N_2O$: C, 83.69; H, 6.09; N, 6.51; O, 3.72. Found: C, 83.89; H, 6.70; N, 6.75. |
| 216 | L1-50 | | Anal. Calcd. For $C_{32}H_{30}N_2O$: C, 83.81; H, 6.59; N, 6.11; O, 3.49. Found: C, 83.96; H, 6.81; N, 6.97. |

TABLE 6-continued
| Example | No. | The structure of the ligand: | structural characterization (elemental analysis) |
|---|---|---|---|
| 217 | L1-51 | 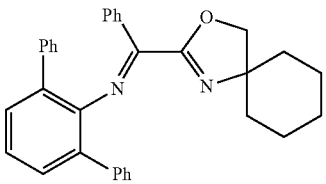 | Anal. Calcd. For $C_{33}H_{30}N_2O$: C, 84.22; H, 6.43; N, 5.95; O, 3.40. Found: C, 84.39; H, 6.50; N, 5.87. |
| 218 | L1-52 | 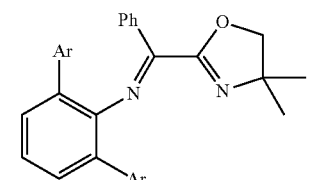<br>Ar = 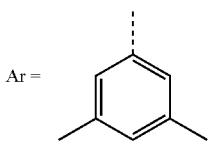 | Anal. Calcd. For $C_{34}H_{34}N_2O$: C, 83.91; H, 7.04; N, 5.76; O, 3.29. Found: C, 84.05; H, 6.97; N, 5.82. |
| 219 | L1-53 | 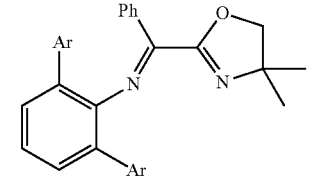<br>Ar = 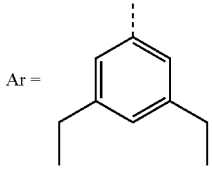 | Anal. Calcd. For $C_{38}H_{42}N_2O$: C, 84.09; H, 7.80; N, 5.16; O, 2.95. Found: C, 84.03; H, 7.59; N, 5.01. |
| 220 | L1-54 | 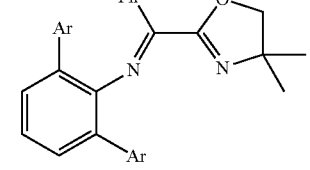<br>Ar = 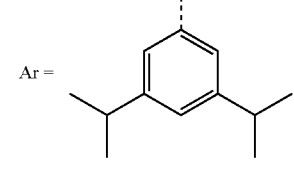 | Anal. Calcd. For $C_{42}H_{50}N_2O$: C, 84.23; H, 8.42; N, 4.68; O, 2.67. Found: C, 84.70; H, 7.64; N, 4.75. |

TABLE 6-continued
| Example | No. | The structure of the ligand: | structural characterization (elemental analysis) |
|---|---|---|---|
| 221 | L1-55 | 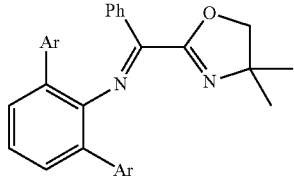 | Anal. Calcd. For $C_{30}H_{22}F_4N_2O$: C, 71.71; H, 4.41; F, 15.12; N, 5.57; O, 3.18. Found: C, 70..89; H, 4.72; N, 5.35. |
| 222 | L1-56 | 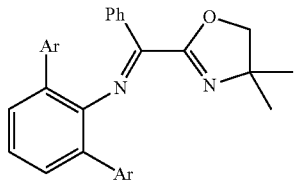 | Anal. Calcd. For $C_{30}H_{22}I_4N_2O$: C, 38.57; H, 2.37; I, 54.34; N, 3.00; O, 1.71. Found: C, 38.09; H, 2.70; N, 3.45. |
| 223 | L1-57 | 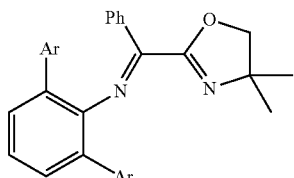 | Anal. Calcd. For $C_{34}H_{34}N_2O_5$: C, 74.16; H, 6.22; N, 5.09; O, 14.53. Found: C, 74.46; H, 6.50; N, 5.18. |
| 224 | L1-58 | 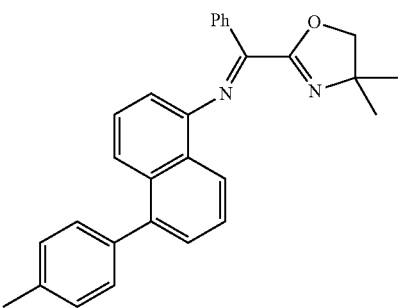 | Anal. Calcd. For $C_{29}H_{26}N_2O$: C, 83.22; H, 6.26; N, 6.69; O, 3.82. Found: C, 83.38; H, 6.53; N, 6.75. |

TABLE 6-continued

| Example | No. | The structure of the ligand: | structural characterization (elemental analysis) |
|---|---|---|---|
| 225 | L1-59 | 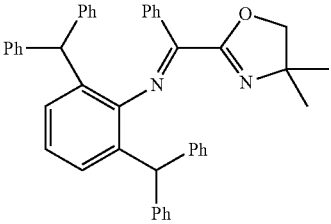 [SMILES: CC1(C)COC(/C(=N/c2c(C(c3ccccc3)c3ccccc3)cccc2C(c2ccccc2)c2ccccc2)c2ccccc2)=N1] | Anal. Calcd. For $C_{44}H_{38}N_2O$: C, 86.52; H, 6.27; N, 4.59; O, 2.62. Found: C, 86.84; H, 6.52; N, 4.76. |

In examples 226-234, different ligand or metal precursor were used instead of the corresponding ligand or metal precursor in example 49 so as to prepare complexes 2-57 to 2-64, and the results are shown in table 7.

TABLE 7

| Example | No. | Structure | elemental analysis |
|---|---|---|---|
| 226 | 2-57 | 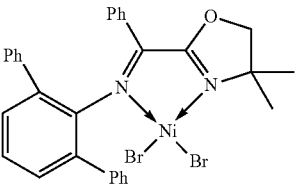 | Anal. Calcd. For $C_{30}H_{26}Br_2N_2NiO$: C, 55.52; H, 4.04; N, 4.32. Found: C, 55.17; H, 4.60; N, 4.15. |
| 227 | 2-58 | 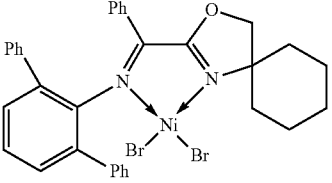 | Anal. Calcd. For $C_{33}H_{30}Br_2N_2NiO$: C, 57.52; H, 4.39; N, 4.07. Found: C, 57.26; H, 4.32; N, 4.40. |
| 22 | 2-59 | 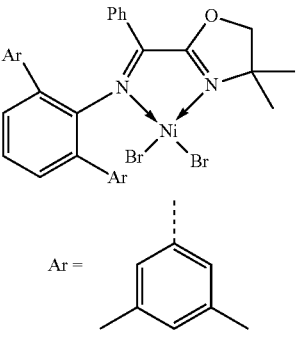 | Anal. Calcd. For $C_{34}H_{34}Br_2N_2NiO$: C, 57.91; H, 4.86; N, 3.97. Found: C, 57.63; H, 5.07; N, 4.05. |
| 229 | 2-60 | 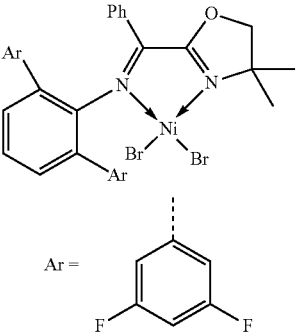 | Anal. Calcd. For $C_{30}H_{22}Br_2F_4N_2NiO$: C, 49.98; H, 3.08; N, 3.89. Found: C, 49.95; H, 3.22; N, 4.18. |

TABLE 7-continued
| Example | No. | Structure | elemental analysis |
|---|---|---|---|
| 230 | 2-61 | 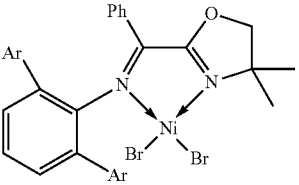 | Anal. Calcd. For $C_{30}H_{22}Br_2I_4N_2NiO$: C, 31.26; H, 1.92; N, 2.43. Found: C, 31.43; H, 1.69; N, 2.45. |
| 231 | 2-62 | 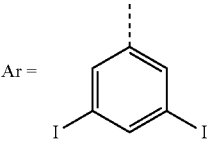 | Anal. Calcd. For $C_{34}H_{34}Br_2N_2NiO_5$: C, 53.09; H, 4.46; N, 3.64. Found: C, 53.67; H, 4.62; N, 3.58. |
| 232 | 2-63 | 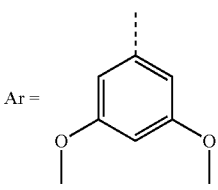 | Anal. Calcd. For $C_{29}H_{26}Br_2N_2NiO$: C, 54.68; H, 4.11; N, 4.40. Found: C, 54.23; H, 4.22; N, 4.32. |
| 234 | 2-64 | 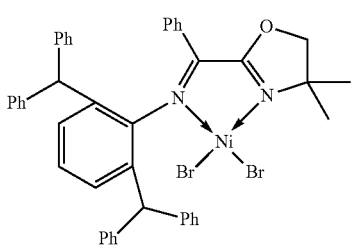 | Anal. Calcd. For $C_{44}H_{38}Br_2N_2NiO$: C, 63.73; H, 4.62; N, 3.38. Found: C, 63.52; H, 4.37; N, 3.40. |

Example 235

The example 118 was repeated except that toluene was replaced by dichloromethane (DCM) and the ethylene pressure was changed to 10 atm, and the complex 2-9 was replaced by complex 2-57.

Results: The activity was $2.3 \times 10^7$ g/mol·h·atm, and the methyl number per 1000 methylene of the oily polyethylene was 201.

Example 236

The example 118 was repeated except that toluene was replaced by dichloromethane (DCM) and the ethylene pressure was changed to 10 atm, and the complex 2-9 was replaced by complex 2-59.

Results: The activity was $2.8 \times 10^7$ g/mol·h·atm, and the methyl number per 1000 methylene of the oily polyethylene was 214.

Example 237

The example 118 was repeated except that toluene was replaced by dichloromethane (DCM) and the ethylene pressure was changed to 10 atm, and the complex 2-9 was replaced by complex 2-61.

Results: The activity was $2.0 \times 10^7$ g/mol·h·atm, and the methyl number per 1000 methylene of the oily polyethylene was 254.

Example 238

The example 118 was repeated except that toluene was replaced by dichloromethane (DCM) and the ethylene pressure was changed to 10 atm, and the complex 2-9 was replaced by complex 2-63.

Results: The activity was $3.3 \times 10^7$ g/mol·h·atm, and the methyl number per 1000 methylene of the oily polyethylene was 243.

Example 239

The example 118 was repeated except that toluene was replaced by dichloromethane (DCM) and the ethylene pressure was changed to 10 atm, and the complex 2-9 was replaced by complex 2-64.

Results: The activity was $8.1 \times 10^7$ g/mol·h·atm, and the methyl number per 1000 methylene of the oily polyethylene was 182.

Example 240

The example 201 was repeated except that the complex 2-2 was replaced by complex 2-57.

Results: The activity was $3.4 \times 10^7$ g/mol·h·atm, and the methyl number per 1000 methylene of the oily polyethylene was 212.

Example 241

The example 201 was repeated except that the complex 2-2 was replaced by complex 2-59.

Results: The activity was $3.8 \times 10^7$ g/mol·h·atm, and the methyl number per 1000 methylene of the oily polyethylene was 225.

Example 242

The example 201 was repeated except that the complex 2-2 was replaced by complex 2-61.

Results: The activity was $2.4 \times 10^7$ g/mol·h·atm, and the methyl number per 1000 methylene of the oily polyethylene was 262.

Example 243

The example 201 was repeated except that the complex 2-2 was replaced by complex 2-63.

Results: The activity was $5.4 \times 10^7$ g/mol·h·atm, and the methyl number per 1000 methylene of the oily polyethylene was 282.

Example 244

2.0 g of highly branched oily polyethylene obtained in example 198, Pd/C 150 mg, 15 mL of n-hexane and 5 mL ethyl acetate were added into a 100 mL egg-shaped flask. After recharged the nitrogen for three times, the reaction was conducted at 1 atm hydrogen atmosphere and at room temperature overnight. It was monitored by $^1$H-NMR until found that the raw material has been hydrogenated completely. Then the hydrogenation was stopped, the reaction mixture was filtered and the solvent was removed to obtain oily highly branched alkane, bromine value of which was 0.31 g/100 g, methyl number per 1000 methylene was 265, the bromine value was 0.43 g/100 g, and the oxidation stability was 107 minutes.

Example 245

2.0 g of highly branched oily polyethylene obtained in example 198, Pd/C 150 mg, 15 mL n-hexane and 5 mL ethyl acetate were added into 50 mL egg-shaped flask. After recharged nitrogen for three times, the reaction was conducted under 1 atm hydrogen atmosphere and at 40° C. for 6 hours before the hydrogenation was stopped.

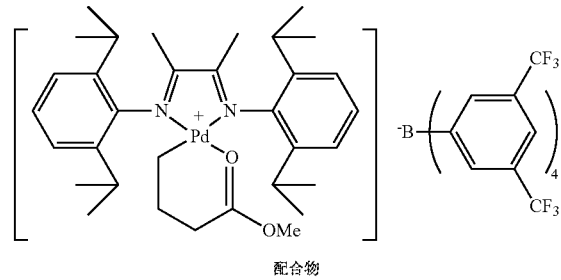

2-65

配合物

The following table lists the hydrogenation conversion rates for several oily polyethylene under the same conditions. P1 was the oily polyethylene obtained in Example 198, P2 was the oily polyethylene obtained in Example 211, P3 was the oily polyethylene prepared through polymerization by using the palladium catalysts (complex 2-65) according to the conditions disclosed in patent (Guan, WO1999047572) example 6.

| Polyethylene | Hydrogenation conversion (%) |
|---|---|
| P1 | 100 |
| P2 | 100 |
| P3 | 63 |

Figure 7:
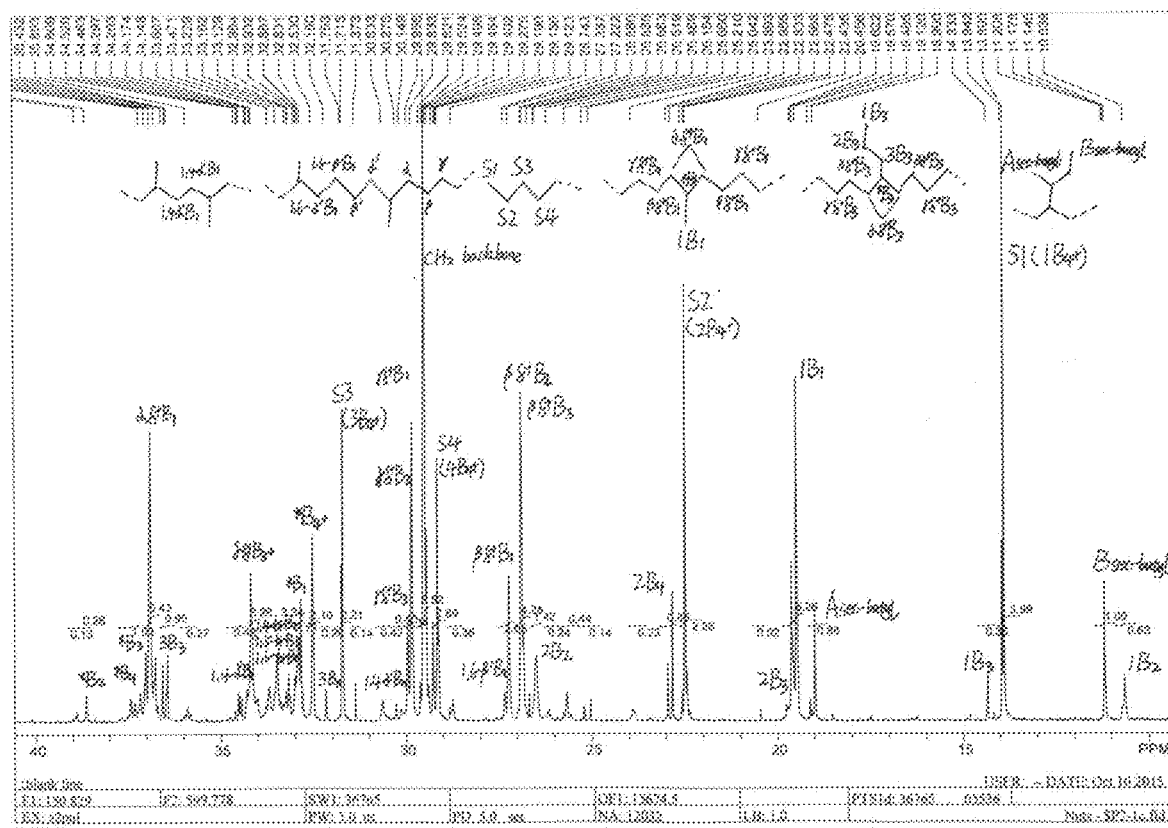
FIG. 7 shows the $^{13}C$ NMR spectrum of the polymer prepared in Example 245 of the present invention.

Under the above conditions, the hydrogenation conversion rate of P1 and P2 were 100%, while the hydrogenation conversion rate of P3 was 63%. The analysis of the branched chain type of the alkane mixture after P1 hydrogenation is shown in FIG. 7.

Example 246

Figure 8:
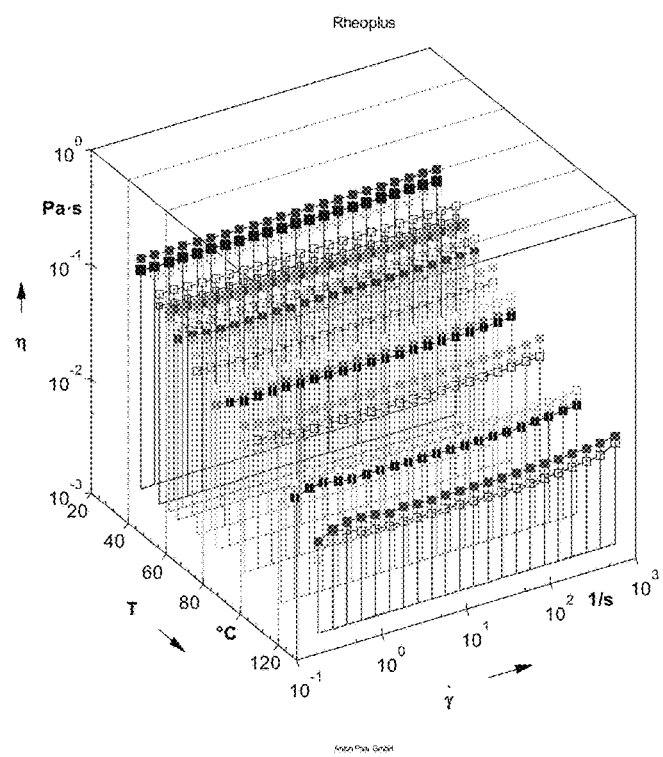
FIG. 8 shows the change of shear viscosity with shear rate at different temperatures of samples P1-hydrogenation, P2-hydrogenation and P3-hydrogenation (alkane mixture).

The rheological properties of the hydrogenated polymers in Example 244 and the hydrogenated products P1-hydrogenation and P2-hydrogenation of the oily sample in 245 were tested by Auton Parr Rotary Rheometer (MCR 302, concentric drum rotor CC27). The results were shown in FIG. 8. The results show that the viscosity of the sample does not change with the shear rate and possesses the properties of the Newtonian fluid within the range of 40-120° C., which also shows that the polymer has hyperbranched structure.

Example 247

10.0 g of highly branched oily polyethylene obtained in example 201, Pd/C 150 mg, n-hexane 100 mL and ethylacetate 30 mL were added into 250 mL egg-shaped flask. After recharged nitrogen for three times, the reaction was conducted under 1 atm hydrogen atmosphere and at room temperature overnight. The reaction was monitored by $^1$H-NMR until that the reactant has been hydrogenated completely. Then the hydrogenation was stopped, the reaction mixture was filtered and the solvent was removed to obtain oily highly branched alkanes, bromine value of which was 0.33 g/100 g, methyl number per 1000 methylene was 274, and viscosity index VI was 253, the kinematic viscosity under 100° C. was 8.4 cSt, and the surface tension was 24.6 mM/m.

Example 248

500 g of highly branched oily polyethylene obtained in example 201, Pd/C 1.5 g, n-hexane 1 L and ethyl acetate 300 mL were added into 2 L reaction flask. After recharged nitrogen for three times, the reaction was conducted at 1 atm hydrogen atmosphere and at 50° C. overnight. The reaction was monitored by $^1$H-NMR until that the raw material has been hydrogenated completely. Then the hydrogenation was stopped, the reaction mixture was filtered and the solvent was removed to obtain oily highly branched alkanes, bromine value of which was 0.38 g/100 g, methyl number per 1000 methylene was 269, and viscosity index VI was 259, the kinematic viscosity at 100° C. was 8.6 cSt, and the surface tension was 24.0 mM/m.

Figure 9:
FIG. 9 shows photo of the polymer prepared in Example 248 of the present invention.

The picture of the oily highly branched alkane is shown in FIG. 9, which is a colorless, clear oily substance.

Example 249

500 g of highly branched oily polyethylene obtained in example 201, Pd/C 1.5 g, n-hexane 1 L and ethyl acetate 300 mL were added into a 2 L autoclave. After recharged nitrogen for three times, the reaction was conducted at 20 bar pressure hydrogen atmosphere and at 50° C. for 6 hours. The reaction was monitored by $^1$H-NMR until that the raw material has been hydrogenated completely. Then the hydrogenation was stopped, the reaction mixture was filtered and the solvent was removed to obtain oily highly branched alkanes, of which bromine value was 0.40 g/100 g, methyl number per 1000 methylene was 273, and viscosity index VI was 261, the kinematic viscosity under 100° C. was 8.2 cSt, and the surface tension was 24.7 mM/m.

Example 250

500 g of highly branched oily polyethylene obtained in example 208, Pd/C 1.5 g, n-hexane 1 L and ethyl acetate 300 mL were added into 2 L autoclave. After recharged nitrogen for three times, the reaction was conducted under 20 bar pressure hydrogen atmosphere and at for 6 hours. The reaction was monitored by $^1$H-NMR until that the raw material has been hydrogenated completely. Then the hydrogenation was stopped, the reaction mixture was filtered and the solvent was removed to obtain oily highly branched alkanes, of which bromine value was 0.50 g/100 g, methyl number per 1000 methylene was 287, and viscosity index VI was 272, the kinematic viscosity at 100° C. was 4.2 cSt, and the surface tension was 22.0 mM/m.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A complex, wherein said complex is formed by a compound of formula I and a divalent or trivalent metal salt, and the complex of the structure represented by following formula II:

wherein, $Y^1$ is C1-C8 alkyl, C1-C8 haloalkyl, or unsubstituted or substituted phenyl;

$Y^2$ is $CR_4R_5$, O or S, $R_4$ and $R_5$ are independently C1-C4 alkyl or haloalkyl;

or $Y^1$ and $Y^2$, and the C—C bond attached to both of them together forms unsubstituted or substituted 5-12 member ring;

together with $Y^3$, is substituted 5-7 member monocyclic, or bicyclic or tricyclic group containing said 5-7 member monocyclic ring, wherein the 5-7 member monocyclic ring contains 1-3 N, O or S atoms, and contains at least one N;

Y³ is one or more substituents on the 5-7 member monocyclic ring, or bicyclic or tricyclic group containing said 5-7 member monocyclic ring, at least one Y³ is halogen, C1-C8 alkyl, C1-C8 haloalkyl, unsubstituted or substituted phenyl, unsubstituted or substituted benzyl, —O—R₇, —CH₂—O—R₈, —SR₉, or —CH₂—S—R₁₀, wherein R₇, R₈, R₉ and R₁₀ are independently C1-C8 alkyl, or unsubstituted or substituted phenyl;

Z is C1-C8 alkyl, C1-C8 haloalkyl, unsubstituted or substituted phenyl, or unsubstituted or substituted naphthyl, provided that Y¹ and Z, and the C=N bond attached to both of them together do not form unsubstituted or substituted 5-12 member ring;

wherein, the "substituted" in the above definitions means that the group possesses 1-5 substituents selected from the group consisting of C1-C4 alkyl, C1-C4 haloalkyl, halogen, nitro, cyano, CF₃, —O—R₁, —N(R₂)₂, —Si(R₃)₃, —CH₂—O—R₈, —SR₉, —CH₂—S—R₁₀, —CH—(R₁₀)₂, and phenyl which is unsubstituted or substituted by 1-5 substituents selected from the group consisting of C1-C4 alkyl and C1-C4 haloalkyl, wherein R₁, R₂ and R₃ are independently C1-C4 alkyl or haloalkyl; while R₈, R₉ and R₁₀ are independently C1-C8 alkyl or phenyl;

M is nickel or palladium;

X is independently halogen, C1-C4 alkyl, C2-C6 alkenyl, allyl (), ⁻OAc, ⁻OTf, or benzyl.

2. The complex of claim 1, wherein

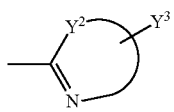

is selected from the following group:

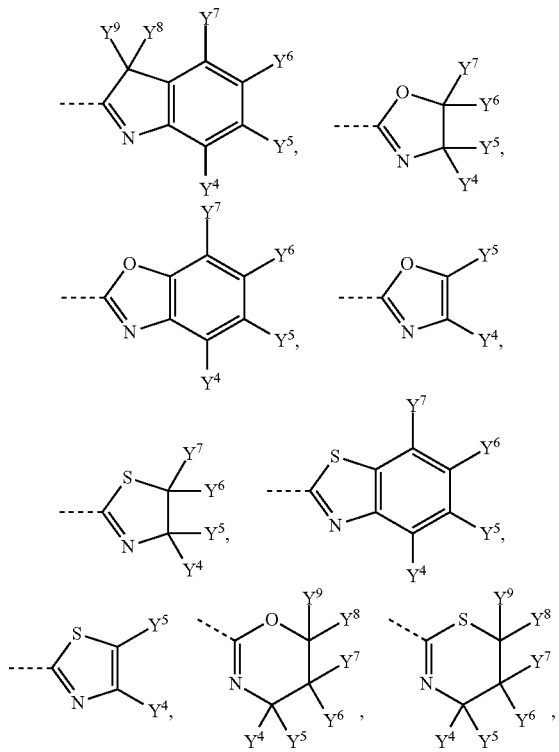

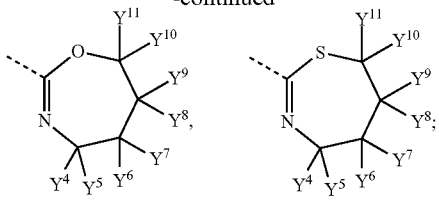

Y⁴ is halogen, C1-C8 alkyl, C1-C8 haloalkyl, unsubstituted or substituted phenyl, unsubstituted or substituted benzyl, —O—R₇, —CH₂—O—R₈, —SR₉, or —CH₂—S—R₁₀, wherein R₇, R₈, R₉ and R₁₀ are independently C1-C8 alkyl, or unsubstituted or substituted phenyl;

Y⁵, Y⁶, Y⁷, Y⁸, Y⁹, Y¹⁰ and Y¹¹ are independently H, halogen, C1-C8 alkyl, C1-C8 haloalkyl, unsubstituted or substituted phenyl, unsubstituted or substituted benzyl, —O—R₇, —CH₂—O—R₈, —SR₉ or —CH₂—S—R₁₀, wherein R₇, R₈, R₉ and R₁₀ are independently C1-C8 alkyl, or unsubstituted or substituted phenyl.

3. The complex of claim 1, wherein the compound I is of the following structure:

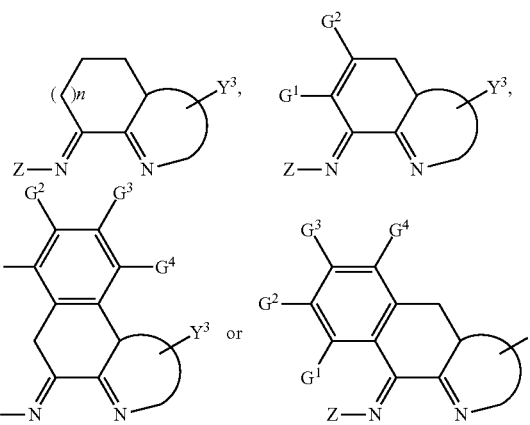

wherein, Y³ or Z are defined as in claim 1;
n is 0, 1, 2, or 3;

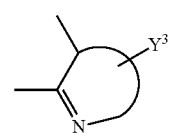

is unsubstituted or substituted 5-7 member monocyclic, or bicyclic or tricyclic group containing said 5-7 member monocyclic ring;

G¹, G², G³ and G⁴ are independently H, halogen, C1-C8 alkyl, C1-C8 haloalkyl, silicon group, unsubstituted or substituted phenyl, unsubstituted or substituted benzyl, —O—R₇, —CH₂—O—R₈, —SR₉ or —CH₂—S—R₁₀, wherein R₇, R₈, R₉ and R₁₀ are independently C1-C8 alkyl, unsubstituted or substituted phenyl; wherein the "substituted" is defined as above.

4. The complex of claim 1, wherein the bicyclic ring containing the 5- to 7-membered monocyclic ring is a spiro or fused ring, and the compound has any of the following structures:

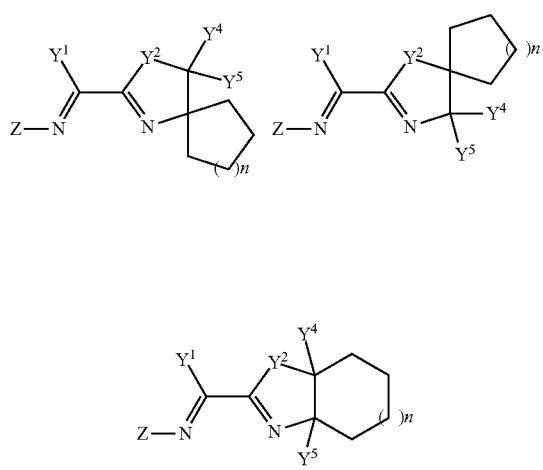

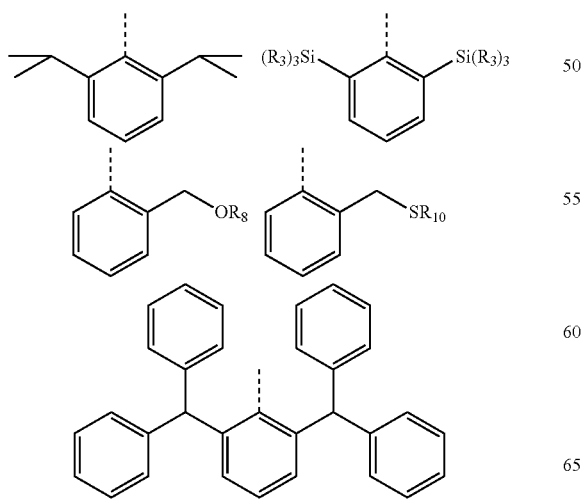

wherein each n is independently 1, 2, 3, or 4;

$Y^1$, $Y^2$ and Z are defined as in claim 1;

$Y^4$ and $Y^5$ are independently H, halogen, C1-C8 alkyl, C1-C8 haloalkyl, unsubstituted or substituted phenyl, unsubstituted or substituted benzyl, —O—$R_7$, —$CH_2$—O—$R_8$, —$SR_9$ or —$CH_2$—S—$R_{10}$, wherein $R_7$, $R_8$, $R_9$ and $R_{10}$ are independently C1-C8 alkyl, unsubstituted or substituted phenyl; provided that $Y^4$ and $Y^5$ cannot be halogen, —O—$R_7$ or —$SR_9$ simultaneously, and Z is unsubstituted or substituted phenyl, or unsubstituted or substituted naphthyl, wherein "substituted" in the above definitions means that the group possesses 1-5 substitutents selected from the following groups: C1-C4 alkyl and C1-C4 haloalkyl, halogen, nitro, cyano, $CF_3$, —O—$R_1$, —$N(R_2)_2$, —$Si(R_3)_3$, —$CH_2$—O—$R_8$, —$SR_9$, —$CH_2$—S—$R_{10}$, —CH—$(R_{10})_2$, or phenyl which is unsubstituted or substituted by 1-5 substituents selected from the following group: C1-C4 alkyl, and C1-C4 haloalkyl, wherein $R_1$, $R_2$, $R_3$ are independently C1-C4 alkyl or haloalkyl; while $R_8$, $R_9$ and $R_{10}$ are independently C1-C8 alkyl or phenyl;

the substituted phenyl group has at most one nitro or cyano group; and Z is one of the following group:

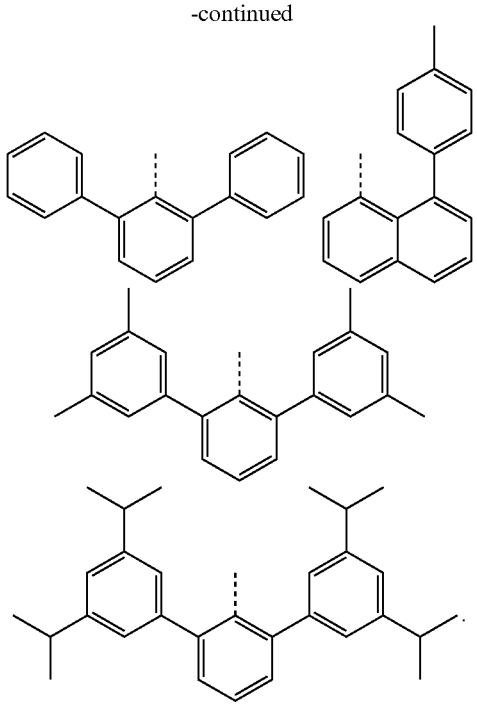

5. The complex of claim 1, wherein the $Y^1$ and $Y^2$ form unsubstituted or substituted C6-C8 ring together with the C—C bond attached with both of them.

6. A complex, wherein said complex is formed by a compound of formula I and a divalent or trivalent metal salt, and the complex of the structure represented by following formula II:

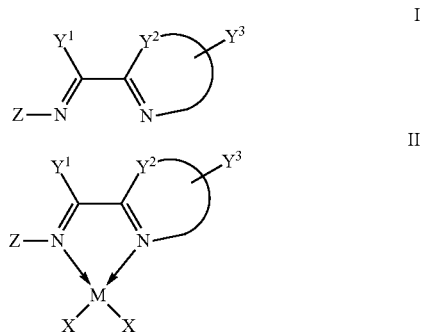

wherein, $Y^1$ is unsubstituted or substituted phenyl;

$Y^2$ is O;

or $Y^1$ and $Y^2$, and the C—C bond attached to both of them together form unsubstituted or substituted 5-12 member ring;

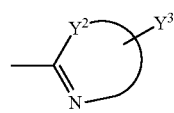

together with $Y^3$, is substituted 5-7 member monocyclic, or bicyclic or tricyclic group containing said 5-7 member monocyclic ring, wherein the 5-7 member monocyclic ring contains 1-3 N, O or S atoms, and contains at least one N;

Y³ is one or more substituents on the 5-7 member monocyclic ring, or bicyclic or tricyclic group containing said 5-7 member monocyclic ring, at least one Y³ is C1-C8 alkyl or C1-C8 haloalkyl;

Z is unsubstituted or substituted phenyl, provided that Y¹ and Z, and the C=N bond attached to both of them together do not form unsubstituted or substituted 5-12 member ring;

wherein, the "substituted" in the above definitions means that the group possesses 1-5 substituents selected from the group consisting of C1-C4 alkyl, C1-C4 haloalkyl, halogen, nitro, cyano, CF₃, —O—R₁, —N(R₂)₂, —Si (R₃)₃, —CH₂—O—R₈, —SR₉, —CH₂—S—R₁₀, —CH—(R₁₀)₂, and phenyl which is unsubstituted or substituted by 1-5 substituents selected from the group consisting of C1-C4 alkyl and C1-C4 haloalkyl, wherein R₁, R₂ and R₃ are independently C1-C4 alkyl or haloalkyl; while R₈, R₉ and R₁₀ are independently C1-C8 alkyl or phenyl;

M is iron, cobalt, nickel, palladium, or combinations thereof; and

X is independently halogen, C1-C4 alkyl, C2-C6 alkenyl, allyl (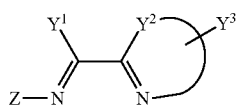), —OAc, —OTf, or benzyl.

7. A complex, wherein said complex is formed by a compound of formula I and a divalent or trivalent metal salt, and the complex of the structure represented by following formula II:

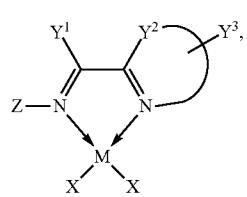

wherein the complex of formula II is selected from the group consisting of:

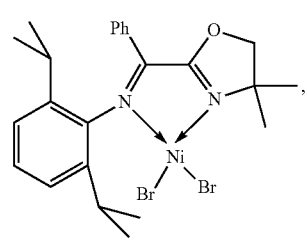

(2-2)

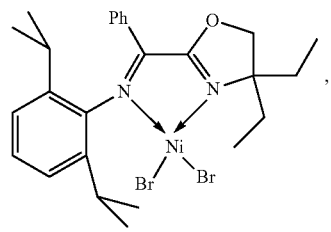

(2-3)

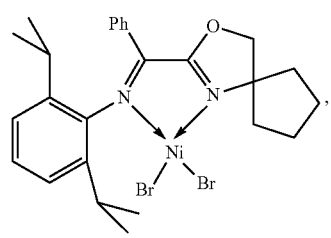

(2-4)

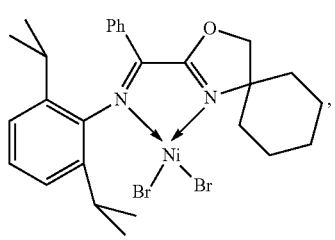

(2-5)

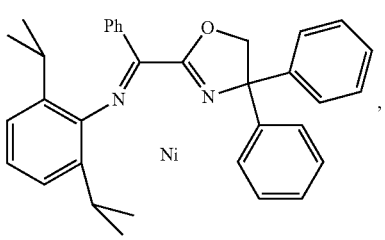

(2-6)

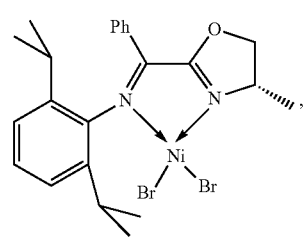

(2-7)

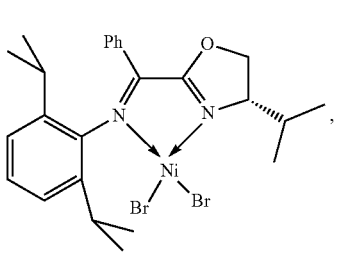

(2-8)

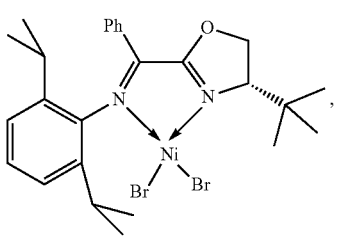

(2-9)

-continued
(2-10)
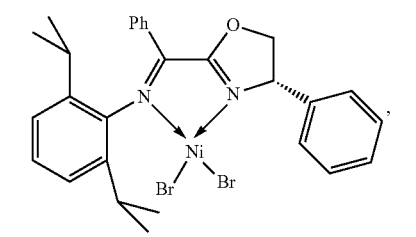
(2-11)
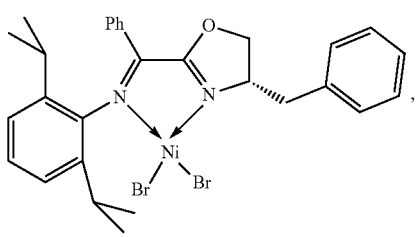
(2-12)
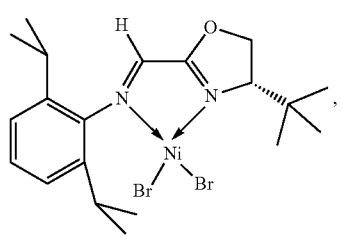
(2-13)
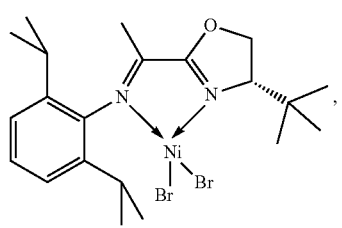
(2-14)
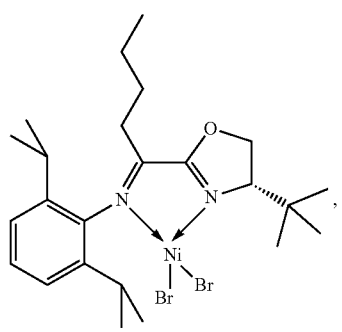
(2-15)
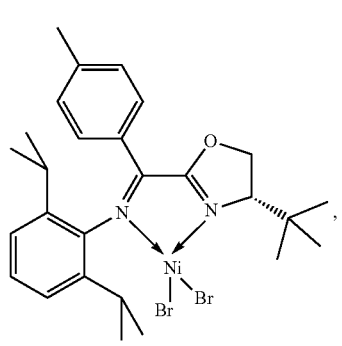
-continued
(2-16)
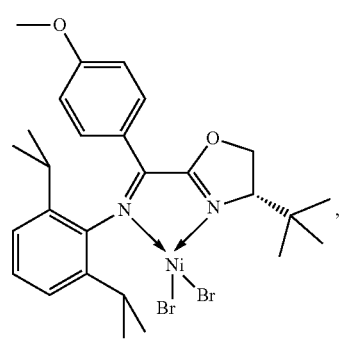
(2-17)
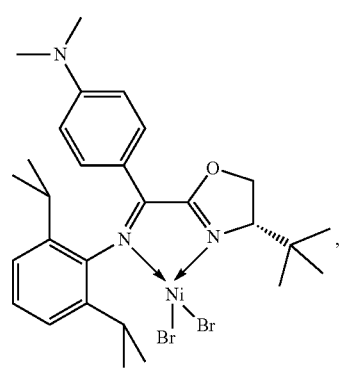
(2-18)
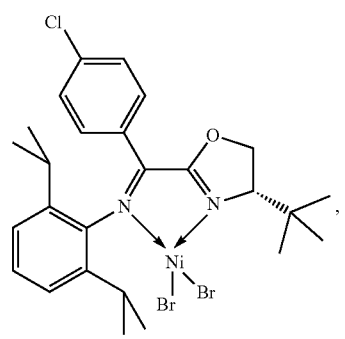
(2-19)
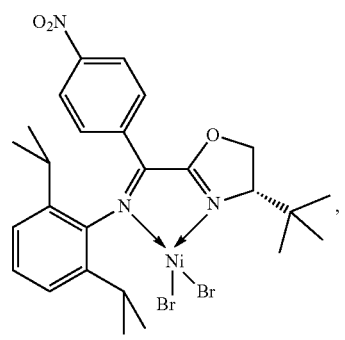

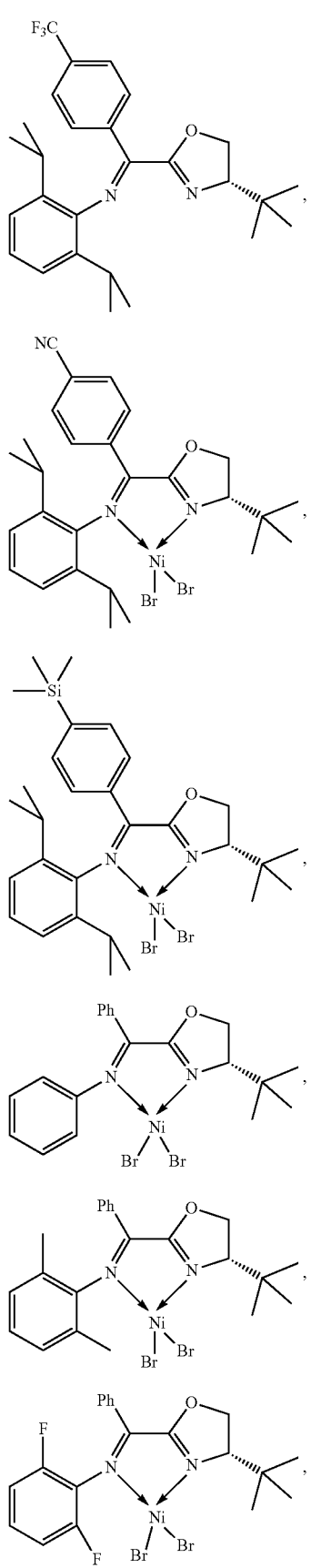
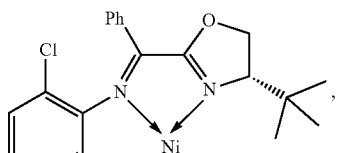
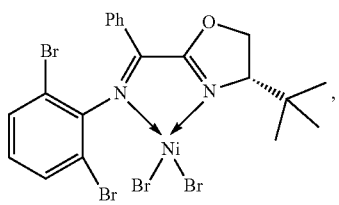
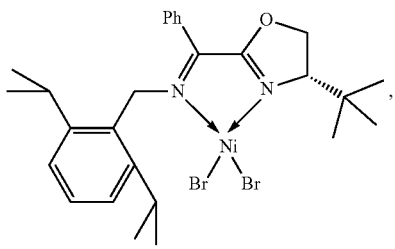
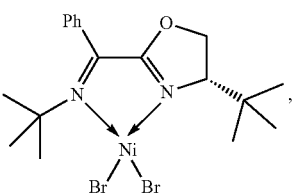
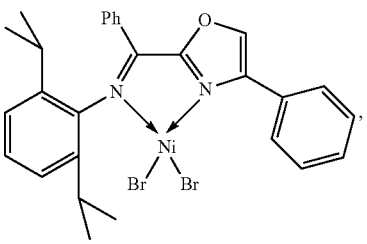
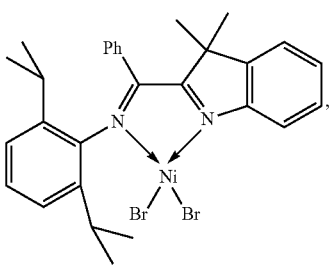
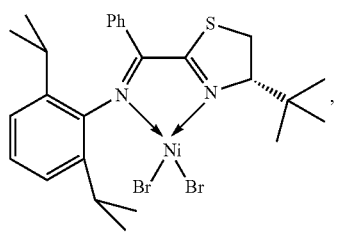

-continued
(2-37)
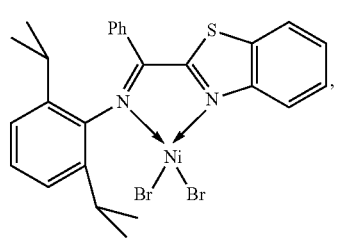
(2-38)
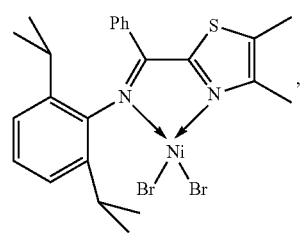
(2-40)
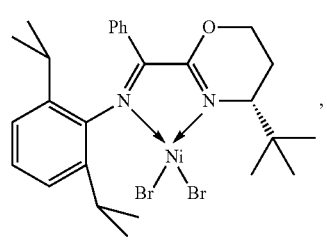
(2-41)
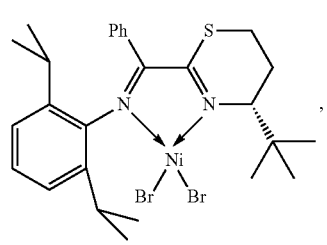
(2-43)
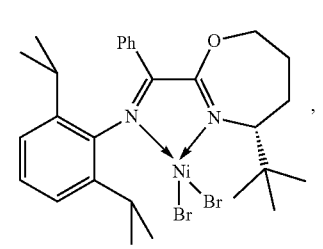
(2-44)
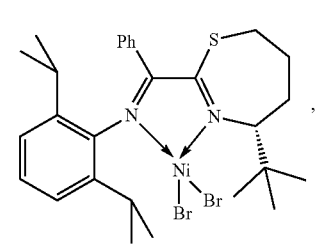
(2-47)
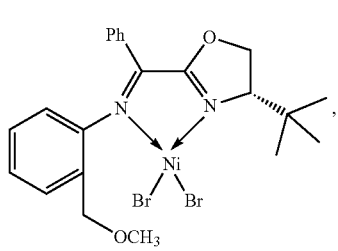
-continued
(2-48)
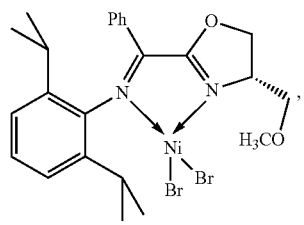
(2-49)
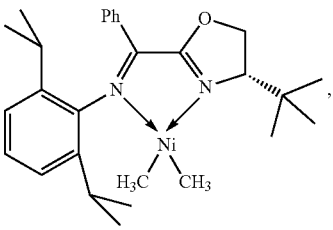
(2-50)
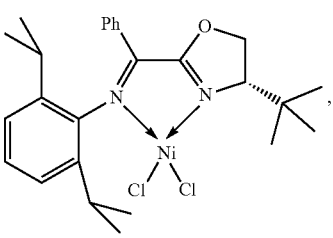
(2-51)
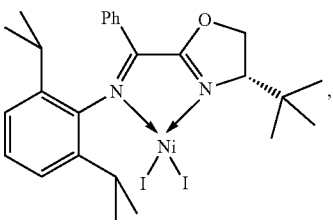
(2-52)
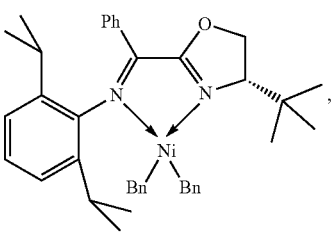
(2-53)
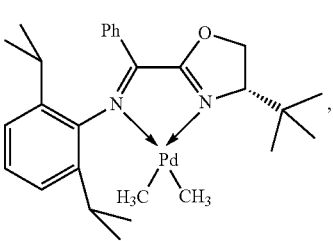
(2-54)
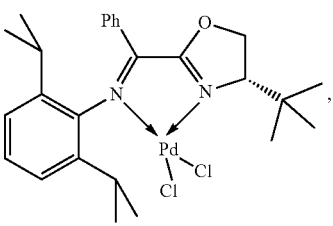

-continued (2-55) 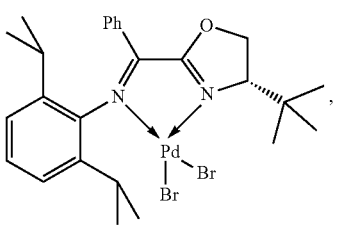

(2-57) 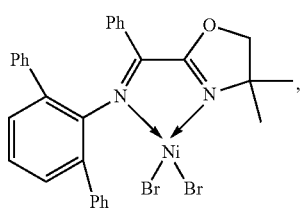

(2-58) 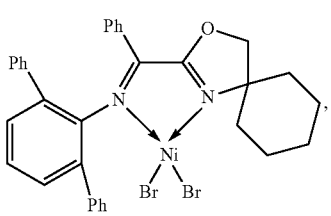

(2-59) 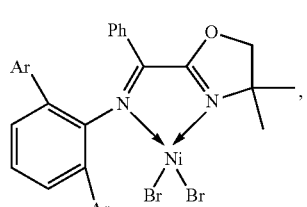

Ar = 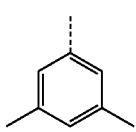

(2-60) 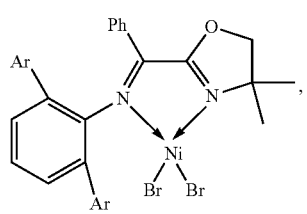

Ar = 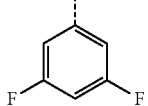

(2-61) 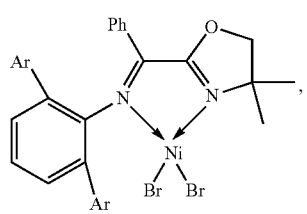

-continued (2-55) Ar = 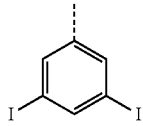

(2-62) 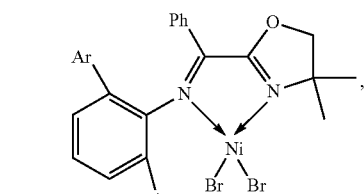

Ar = 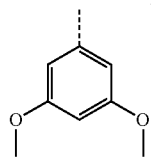

(2-63) 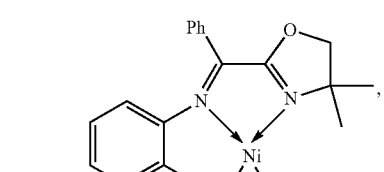, and (2-64) 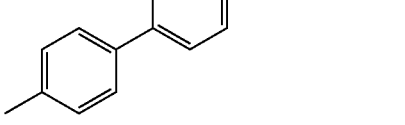

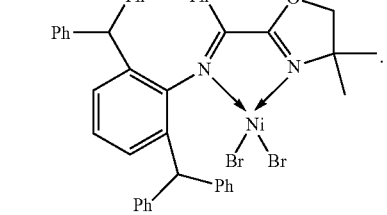
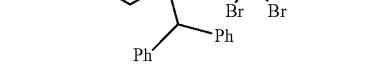

8. A method for preparing the complex of claim 1, the method comprising the following steps:
in an inert solvent, treating the compound I with a divalent or trivalent metal salt to provide the complex of claim 1 wherein the divalent or trivalent metal salt is selected from the group consisting of $NiCl_2$, $NiBr_2$, $NiI_2$, $(DME)NiBr_2$, $PdCl_2$, $PdBr_2$, $Pd(OTf)_2$, $Pd(OAc)_2$, $(COD)PdMeCl$, and combinations thereof.

9. A method for preparing an oily polyolefin, the method comprising the following steps:
(a) catalyzing olefins polymerization by the complex according to claim 1, in the presence of alkylaluminum compound as cocatalyst to form an oily polyolefin; wherein the olefin is ethylene, propylene or C4-C20 α-olefins, inner olefins, dienes, or the mixtures thereof.

10. The method of claim 9, wherein further comprises the following steps:
(b) hydrogenating the oily polyolefin obtained in step (a) to obtain a hydrogenated oily alkane mixture.

* * * * *